(12) United States Patent
Culbert

(10) Patent No.: US 9,028,533 B2
(45) Date of Patent: *May 12, 2015

(54) METHOD AND APPARATUS FOR SPINAL STABILIZATION

(75) Inventor: Brad S. Culbert, Rancho Santa Margarit, CA (US)

(73) Assignee: Interventional Spine, Inc., Irvine, CA (US)

( * ) Notice: Subject to any disclaimer, the term of this patent is extended or adjusted under 35 U.S.C. 154(b) by 806 days.

This patent is subject to a terminal disclaimer.

(21) Appl. No.: 13/177,378

(22) Filed: Jul. 6, 2011

(65) Prior Publication Data

US 2011/0264147 A1    Oct. 27, 2011

Related U.S. Application Data

(63) Continuation of application No. 12/134,886, filed on Jun. 6, 2008, now Pat. No. 7,998,176.

(60) Provisional application No. 60/942,998, filed on Jun. 8, 2007.

(51) Int. Cl.
| | |
|---|---|
| *A61B 17/88* | (2006.01) |
| *A61B 17/70* | (2006.01) |
| *A61B 17/16* | (2006.01) |
| *A61B 17/86* | (2006.01) |

(52) U.S. Cl.
CPC ......... *A61B 17/7064* (2013.01); *A61B 17/1664* (2013.01); *A61B 17/1671* (2013.01); *A61B 17/1682* (2013.01); *A61B 17/1686* (2013.01); *A61B 17/862* (2013.01); *A61B 17/863* (2013.01); *A61B 17/864* (2013.01); *A61B 17/8883* (2013.01); *A61B 17/8891* (2013.01)

(58) Field of Classification Search
CPC .......... A61B 17/1671; A61B 17/8891; A61B 17/863; A61B 17/7064; A61B 17/1664; A61B 17/1682; A61B 17/1686; A61B 17/862; A61B 17/864; A61B 17/8883
USPC ....... 606/246–248, 86 A, 301, 279, 264, 328; 128/898
See application file for complete search history.

(56) References Cited

U.S. PATENT DOCUMENTS

| | | | | |
|---|---|---|---|---|
| 5,569,248 | A * | 10/1996 | Mathews | 606/264 |
| 6,610,091 | B1 * | 8/2003 | Reiley | 623/17.11 |
| 6,669,729 | B2 * | 12/2003 | Chin | 623/17.11 |
| 7,699,878 | B2 * | 4/2010 | Pavlov et al. | 606/279 |
| 7,998,176 | B2 * | 8/2011 | Culbert | 606/279 |

* cited by examiner

*Primary Examiner* — Pedro Philogene
(74) *Attorney, Agent, or Firm* — Knobbe, Martens, Olson & Bear, LLP

(57) ABSTRACT

A method and apparatus of limiting at least one degree of movement between a superior vertebral body, an inferior vertebral body, and an intermediate vertebral body that is disposed between the superior and inferior vertebral bodies of a patient. The method can comprise: advancing a distal end of a stabilization device into a pedicle of the intermediate vertebral body; positioning a proximal portion of the stabilization device such that the proximal portion limits at least one degree of movement between the superior vertebral body and the intermediate vertebral body by contacting a surface of the superior vertebral body; and advancing a distal end of a fixation device into a facet of the intermediate vertebral body and into a facet or pedicle of the inferior vertebral body for stabilizing the intermediate vertebral body and the inferior vertebral body.

6 Claims, 43 Drawing Sheets

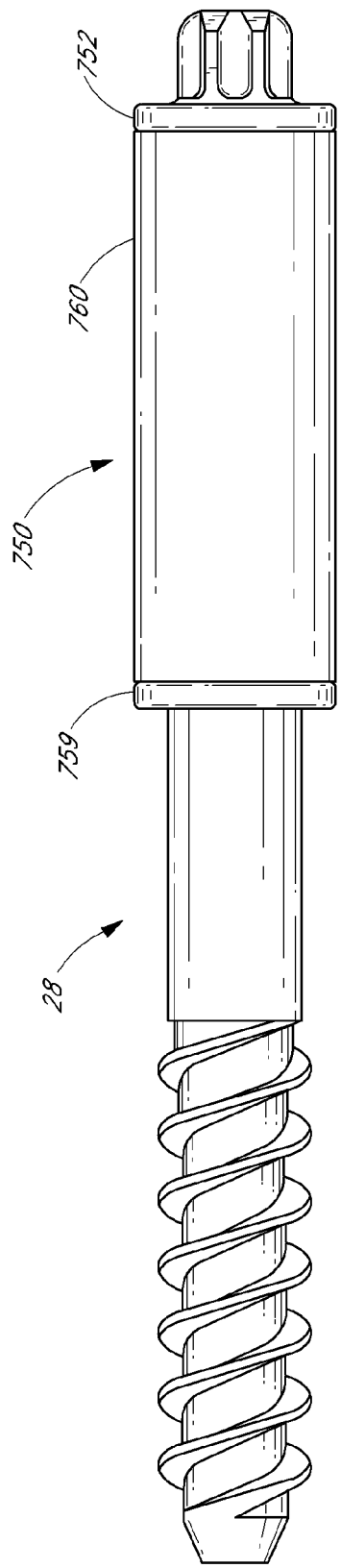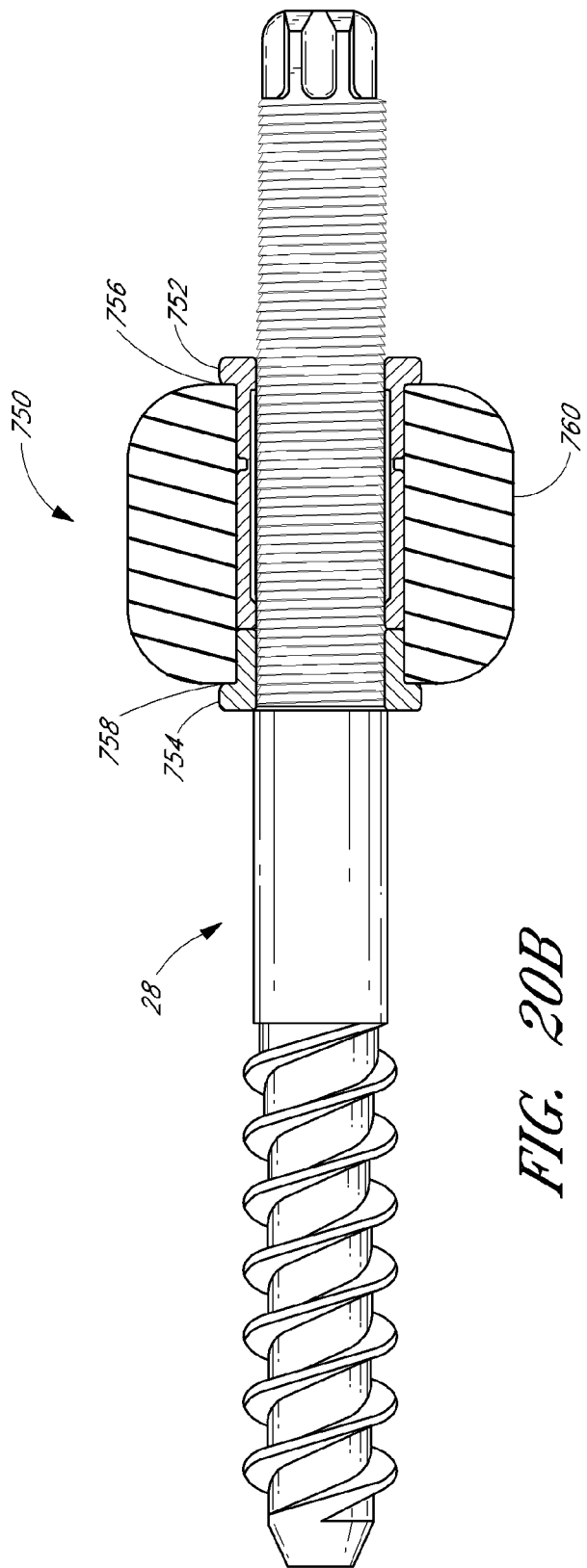
FIG. 20A
FIG. 20B

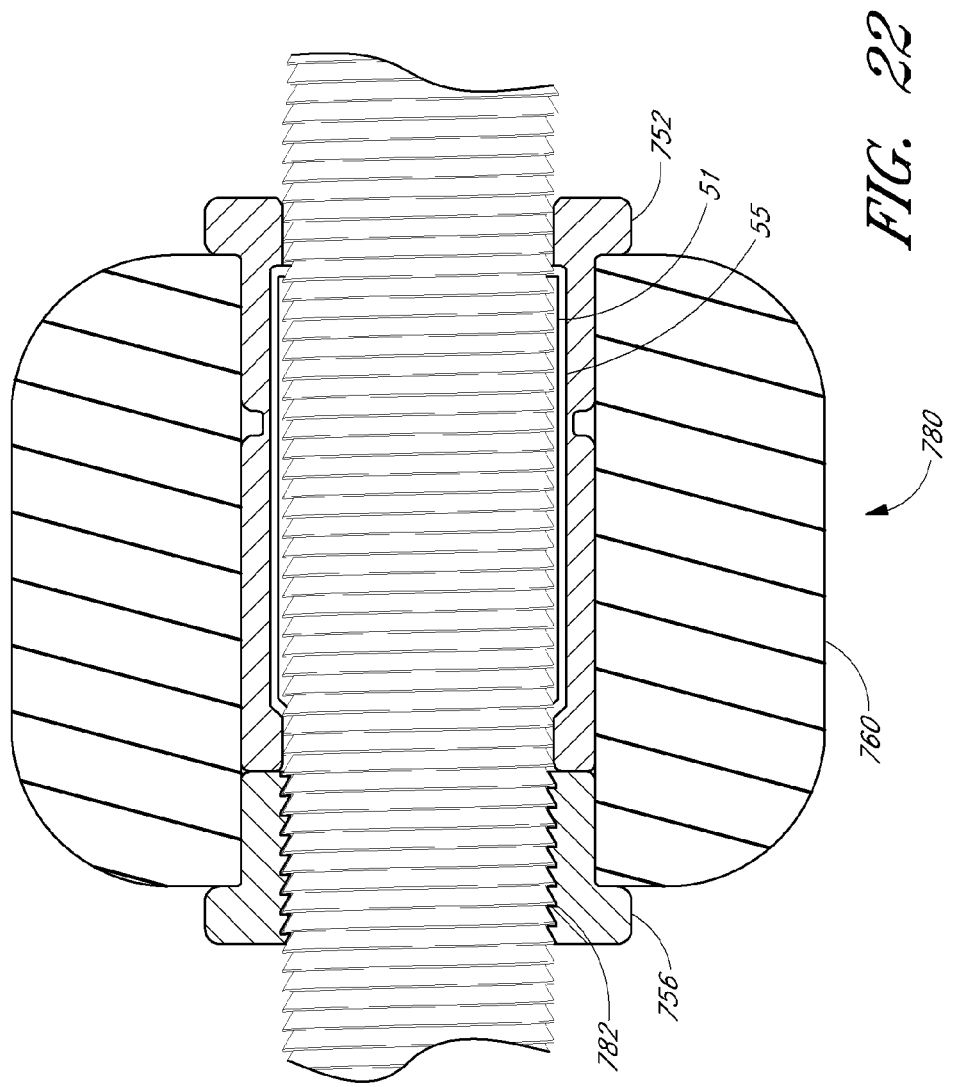

METHOD AND APPARATUS FOR SPINAL STABILIZATION

CROSS-REFERENCE TO RELATED APPLICATIONS

The present application is a continuation of U.S. patent application Ser. No. 12/134,886, filed Jun. 6, 2008, which claims priority under 35 U.S.C. §119(e) to U.S. Provisional Patent Application No. 60/942,998, filed Jun. 8, 2007, the disclosures of these applications are incorporated by reference herein in their entireties.

BACKGROUND

1. Field of the Inventions

The present inventions relate to medical devices and, more particularly, to methods and apparatuses for dynamic spinal stabilization.

2. Description of the Related Art

The human spine is a flexible weight bearing column formed from a plurality of bones called vertebrae. There are thirty three vertebrae, which can be grouped into one of five regions (cervical, thoracic, lumbar, sacral, and coccygeal). Moving down the spine, there are generally seven cervical vertebra, twelve thoracic vertebra, five lumbar vertebra, five sacral vertebra, and four coccygeal vertebra. The vertebra of the cervical, thoracic, and lumbar regions of the spine are typically separate throughout the life of an individual. In contrast, the vertebra of the sacral and coccygeal regions in an adult are fused to form two bones, the five sacral vertebra which form the sacrum and the four coccygeal vertebra which form the coccyx.

In general, each vertebra contains an anterior, solid segment or body and a posterior segment or arch. The arch is generally formed of two pedicles and two laminae, supporting seven processes—four articular, two transverse, and one spinous. There are exceptions to these general characteristics of a vertebra. For example, the first cervical vertebra (atlas vertebra) has neither a body nor spinous process. In addition, the second cervical vertebra (axis vertebra) has an odontoid process, which is a strong, prominent process, shaped like a tooth, rising perpendicularly from the upper surface of the body of the axis vertebra. Further details regarding the construction of the spine may be found in such common references as Gray's Anatomy, Crown Publishers, Inc., 1977, pp. 33-54, which is herein incorporated by reference.

The human vertebrae and associated connective elements are subjected to a variety of diseases and conditions which cause pain and disability. Among these diseases and conditions are spondylosis, spondylolisthesis, vertebral instability, spinal stenosis and degenerated, herniated, or degenerated and herniated intervertebral discs. Additionally, the vertebrae and associated connective elements are subject to injuries, including fractures and torn ligaments and surgical manipulations, including laminectomies.

The pain and disability related to the diseases and conditions often result from the displacement of all or part of a vertebra from the remainder of the vertebral column. Over the past two decades, a variety of methods have been developed to restore the displaced vertebra to their normal position and to fix them within the vertebral column. Spinal fusion is one such method. In spinal fusion, one or more of the vertebra of the spine are united together ("fused") so that motion no longer occurs between them. The vertebra may be united with various types of fixation systems. These fixation systems may include a variety of longitudinal elements such as rods or plates that span two or more vertebrae and are affixed to the vertebrae by various fixation elements such as wires, staples, and screws (often inserted through the pedicles of the vertebrae). These systems may be affixed to either the posterior or the anterior side of the spine. In other applications, one or more bone screws may be inserted through adjacent vertebrae to provide stabilization.

Although spinal fusion is a highly documented and proven form of treatment in many patients, there is currently a great interest in surgical techniques that provide stabilization of the spine while allowing for some degree of movement. In this manner, the natural motion of the spine can be preserved, especially for those patients with mild or moderate disc conditions. In certain types of these techniques, flexible materials are used as fixation rods to stabilize the spine while permitting a limited degree of movement.

SUMMARY

Notwithstanding the variety of efforts in the prior art described above, these techniques are associated with a variety of disadvantages. In particular, these techniques typically involve an open surgical procedure, which results higher cost, lengthy in-patient hospital stays and the pain associated with open procedures.

Therefore, there remains a need for improved techniques and systems for stabilizing the spine. For example, the devices can be implantable through a minimally invasive procedure.

Accordingly, one embodiment of the present inventions comprises a method of limiting at least one degree of movement between a superior vertebral body, an intermediate vertebral body, and an inferior vertebral body of a patient. In accordance with an embodiment of the method, a distal end of a stabilization device can be advanced into a pedicle of the intermediate vertebral body. A proximal portion of the stabilization device can be positioned such that the proximal portion limits at least one degree of movement between a superior vertebral body and the intermediate vertebral body by contacting a surface of the superior vertebral body. Further, the method can further comprise advancing a distal end of a fixation device into a facet of the intermediate vertebral body and into a facet of the inferior vertebral body for stabilizing the intermediate vertebral body and the inferior vertebral body.

Some implementations of the embodiment of the method described above can be modified such that the step of positioning a proximal portion of the stabilization device can comprise advancing a proximal anchor distally over an elongated body of the stabilization device. Further, the step of advancing a proximal anchor distally over an elongated body of the stabilization device can comprise proximally retracting the elongated body with respect to the proximal anchor. Additionally, the step of advancing a proximal anchor distally over an elongated body of the stabilization device can comprise applying a distal force to the proximal anchor.

In other implementations, the method can further comprise maintaining the patient in a face down position during the step of advancing a distal end of a stabilization device into the pedicle of the intermediate vertebral body. The step of advancing a distal end of a stabilization device into a pedicle of the intermediate vertebral body can comprise advancing the distal end of the stabilization device through the pars of the intermediate vertebral body. The steps of advancing a distal end of a stabilization device into a pedicle of the intermediate vertebral body and positioning a proximal portion of the stabilization device can be accomplished through a minimally invasive surgical approach.

Further, the step of advancing a distal end of a stabilization device into a pedicle of the intermediate vertebral body can comprise rotating the distal end of the stabilization device. Furthermore, advancing a distal end of a stabilization device into a pedicle of the intermediate vertebral body can further comprise advancing the stabilization device over a guidewire. In addition, advancing a distal end of a stabilization device into a pedicle of the intermediate vertebral body can further comprise advancing the stabilization device through an expanded tissue tract.

Another embodiment comprises a method of limiting at least one degree of movement between a superior vertebral body and an intermediate vertebral body of a patient. According to such an embodiment, a distal end of a first stabilization device can be advanced into a pedicle of the intermediate vertebral body. A proximal portion of the first stabilization device can be positioned such that the proximal portion abuts against a surface of an intermediate articular process of the superior adjacent vertebral body to limit at least one degree of movement between a superior vertebral body and an intermediate vertebral body. A distal end of a second stabilization device can be advanced into a pedicle of the intermediate vertebral body such that it is positioned with bilateral symmetry with respect to the first stabilization device. A proximal portion of the second stabilization device can be positioned such that the proximal portion abuts, with bilateral symmetry with respect to the first stabilization device, against a surface of a second intermediate articular process of the superior adjacent vertebral body to limit at least one degree of movement between the superior vertebral body and the intermediate vertebral body. Further, the method can also comprise advancing a distal end of a fixation device into a facet of the intermediate vertebral body and into a facet of the inferior vertebral body for stabilizing the intermediate vertebral body and the inferior vertebral body.

In some implementations of the method, the first and second stabilization devices can be used to limit extension and/or flexion between the superior vertebral body and the intermediate vertebral body. Further, the first and second stabilization devices can be used to limit lateral movement between the superior vertebral body and the intermediate vertebral body.

In accordance with yet another embodiment, a kit is provided for dynamic spinal stabilization. The kit can comprise one or more spinal stabilization devices and one or more orthopedic fixation devices. Each spinal stabilization device can comprise an elongate body, a distal anchor, a retention structure, a proximal anchor, and at least one complementary retention structure. The elongate body can have a proximal end and a distal end. The distal anchor can be disposed on the distal end of the elongate body. The retention structure can be disposed on the body, proximal to the distal anchor. The proximal anchor can be moveably carried by the body, and the proximal anchor can have an outer surface, and at least a portion of the outer surface can be elastic. The at least one complementary retention structure can be disposed on the proximal anchor and can be configured for permitting proximal movement of the body with respect to the proximal anchor but resisting distal movement of the body with respect the proximal anchor.

The orthopedic fixation device can comprise an elongate body, a distal anchor, a retention structure, a proximal anchor, at least one complementary retention structure, and a washer. The elongate body can have a proximal end and a distal end. The distal anchor can be disposed on the distal end. The retention structure can be disposed on the elongate body, proximal to the anchor. The proximal anchor can be moveably carried by the elongate body, and the proximal anchor can comprise a tubular sleeve and a radially outward extending head. The at least one complementary retention structure can be disposed on the proximal anchor and can be configured for permitting proximal movement of the elongate body with respect to the proximal anchor but resisting distal movement of the elongate body with respect the proximal anchor. The washer can be angularly moveable with respect to the longitudinal axis of the tubular sleeve. The washer can have an aperture that is elongated with respect to a first axis such that the washer permits greater angular movement with respect to the longitudinal axis of the tubular sleeve in a plane containing the first axis.

In some embodiments, the kit can be configured such that the distal anchor of each stabilization device comprises a helical flange. The retention structure on the body and the at least one complementary retention structure on the proximal anchor of each stabilization device can also comprise a series of ridges and grooves. For example, the at least one complementary retention structure on the proximal anchor of each stabilization device can comprise an annular ring positioned within a recess formed between the proximal anchor and the elongate pin.

Further, the proximal anchor of each stabilization device can also include a distally facing surface. The distally facing surface can include at least one bone engagement feature. The aperture of each orthopedic fixation device can circumscribe a channel having a width in a first direction and a height in a second direction that is perpendicular to the first direction. The width can be smaller than the maximum diameter of the head and the height can be greater than the width. In addition, the distal anchor of each orthopedic fixation device can comprise a helical flange. In some implementations, the distal anchor of each orthopedic fixation device can be moveable from an axial orientation for distal insertion through a bore to an incline orientation to resist axial movement through the bore.

In other embodiments, the retention structures of the elongate body and the proximal anchor of each orthopedic fixation device can permit proximal movement of the elongate body with respect to the proximal anchor without rotation. The washer of each orthopedic fixation device can include a bottom wall, a side wall and a lip for retaining the head of the proximal anchor within the washer. The elongated body of each orthopedic fixation device can comprise a first portion and a second portion that are detachably coupled together at a junction. The first portion of each orthopedic fixation device can include an anti-rotation structure and the proximal anchor of each orthopedic fixation device includes a complementary anti-rotation structure to prevent rotation between the first portion and the proximal anchor.

In yet another embodiment, a kit is provided for dynamic spinal stabilization, and can comprise one or more spinal stabilization devices and one or more orthopedic fixation devices. The spinal stabilization device can be used for limiting at least one degree of movement between a superior vertebral body and an inferior vertebral body of a patient, and can comprise an elongate body, a distal anchor, a retention structure, a proximal anchor, and at least one complementary retention structure. The elongate body can have a proximal end and a distal end. The distal anchor can be disposed on the distal end of the elongate body. The retention structure can be disposed on the body, proximal to the distal anchor. The proximal anchor can be moveably carried by the body and can include at least one flat surface configured to abut against a surface of an inferior articular process of the superior adjacent vertebral body when the stabilization device is inserted into the inferior adjacent vertebral body. Finally, the at least one complementary retention structure can be disposed on the proximal anchor and can be configured for permitting proximal movement of the body with respect to the proximal anchor but resisting distal movement of the body with respect the proximal anchor.

In such an embodiment, the orthopedic fixation device can comprise an elongate pin, at least one distal anchor, a proximal anchor, and an anti-rotational structure. The elongate pin can have a proximal end, a distal end, and a first retention structure. The at least one distal anchor can be carried by the elongate pin. The proximal anchor can be axially moveable with respect to the elongate pin and can comprise a split ring positioned within an annular recess formed within the proximal anchor. The split ring can have at least one gap formed between two ends and can be moveable between a first position and a second position. The second position can be located closer to the longitudinal axis of the elongate pin as compared to the first portion so as to engage the first retention structure and prevent proximal movement of the proximal anchor with respect to the elongated pin while the first position allows distal movement of the proximal anchor with respect to the pin. The anti-rotational structure can prevent rotation of the split ring about the longitudinal axis of the elongate pin.

Some embodiments of the kit can be configured such that the elongate pin of each orthopedic fixation device includes at least one anti-rotational feature configured to engage a complementary anti-rotational feature of the proximal anchor. In such an embodiment, the anti-rotational structure of each orthopedic fixation device can position the gap of the split ring such that it is positioned over the anti-rotational feature of the elongate pin. Further, the anti-rotational feature of the elongate pin of each orthopedic fixation device can comprise at least one flat side. The anti-rotational feature of each orthopedic fixation device can also comprise includes a pair of tabs that extend inwardly from the tubular body toward the longitudinal axis of the tubular body and positioned between the gap of the split ring.

In additional embodiments of the kit, the distal anchor of each orthopedic fixation device can comprise a helical flange. Further, the distal anchor of each orthopedic fixation device can be moveable from an axial orientation for distal insertion through a bore to an incline orientation to resist axial movement through the bore. The elongate pin of each orthopedic fixation device can also comprise a first portion and a second portion that are detachably coupled together at a junction. Further, the first portion of each orthopedic fixation device can include an anti-rotation structure and the proximal anchor of each orthopedic fixation device can include a complementary anti-rotation structure to prevent rotation between the first portion and the proximal anchor.

BRIEF DESCRIPTION OF THE DRAWINGS

The above-mentioned and other features of the inventions disclosed herein are described below with reference to the drawings of the preferred embodiments. The illustrated embodiments are intended to illustrate, but not to limit the inventions. The drawings contain the following figures:

FIG. 20A is a side view of a modified embodiment of a stabilization device in an un-expanded configuration.

FIG. 20B is a cross-sectional side view of the stabilization device shown in FIG. 20A in an expanded configuration.

FIG. 22 is a cross-sectional side view of yet another modified embodiment of a stabilization device in an expanded configuration.

FIG. 28 is a side elevational view of the portion of the vertebra shown in

FIG. 27 having an exemplary embodiment of a stabilization device implanted therein.

DETAILED DESCRIPTION OF THE PREFERRED EMBODIMENTS

Although embodiments of the present inventions will be disclosed primarily in the context of a spinal stabilization procedure, the methods and structures disclosed herein are intended for application in any of a variety medical applications, as will be apparent to those of skill in the art in view of the disclosure herein. For example, certain features and aspects of bone stabilization device and techniques described herein may be applicable to proximal fractures of the femur and a wide variety of fractures and osteotomies, the hand, such as interphalangeal and metacarpophalangeal arthrodesis, transverse phalangeal and metacarpal fracture fixation, spiral phalangeal and metacarpal fracture fixation, oblique phalangeal and metacarpal fracture fixation, intercondylar phalangeal and metacarpal fracture fixation, phalangeal and metacarpal osteotomy fixation as well as others known in the art. See e.g., U.S. Pat. No. 6,511,481, which is hereby incorporated by reference herein. A wide variety of phalangeal and metatarsal osteotomies and fractures of the foot may also be stabilized using the bone fixation devices described herein. These include, among others, distal metaphyseal osteotomies such as those described by Austin and Reverdin-Laird, base wedge osteotomies, oblique diaphyseal, digital arthrodesis as well as a wide variety of others that will be known to those of skill in the art. Fractures of the fibular and tibial malleoli, pilon fractures and other fractures of the bones of the leg may be fixated and stabilized with these bone fixation devices with or without the use of plates, both absorbable or non-absorbing types, and with alternate embodiments of the current inventions. The stabilization devices may also be used to attach tissue or structure to the bone, such as in ligament reattachment and other soft tissue attachment procedures. Plates and washers, with or without tissue spikes for soft tissue attachment, and other implants may also be attached to bone, using either resorbable or nonresorbable fixation devices depending upon the implant and procedure. The stabilization devices may also be used to attach sutures to the bone, such as in any of a variety of tissue suspension procedures. The bone stabilization device described herein may be used with or without plate(s) or washer(s), all of which can be either permanent, absorbable, or combinations.

Figure 1A:
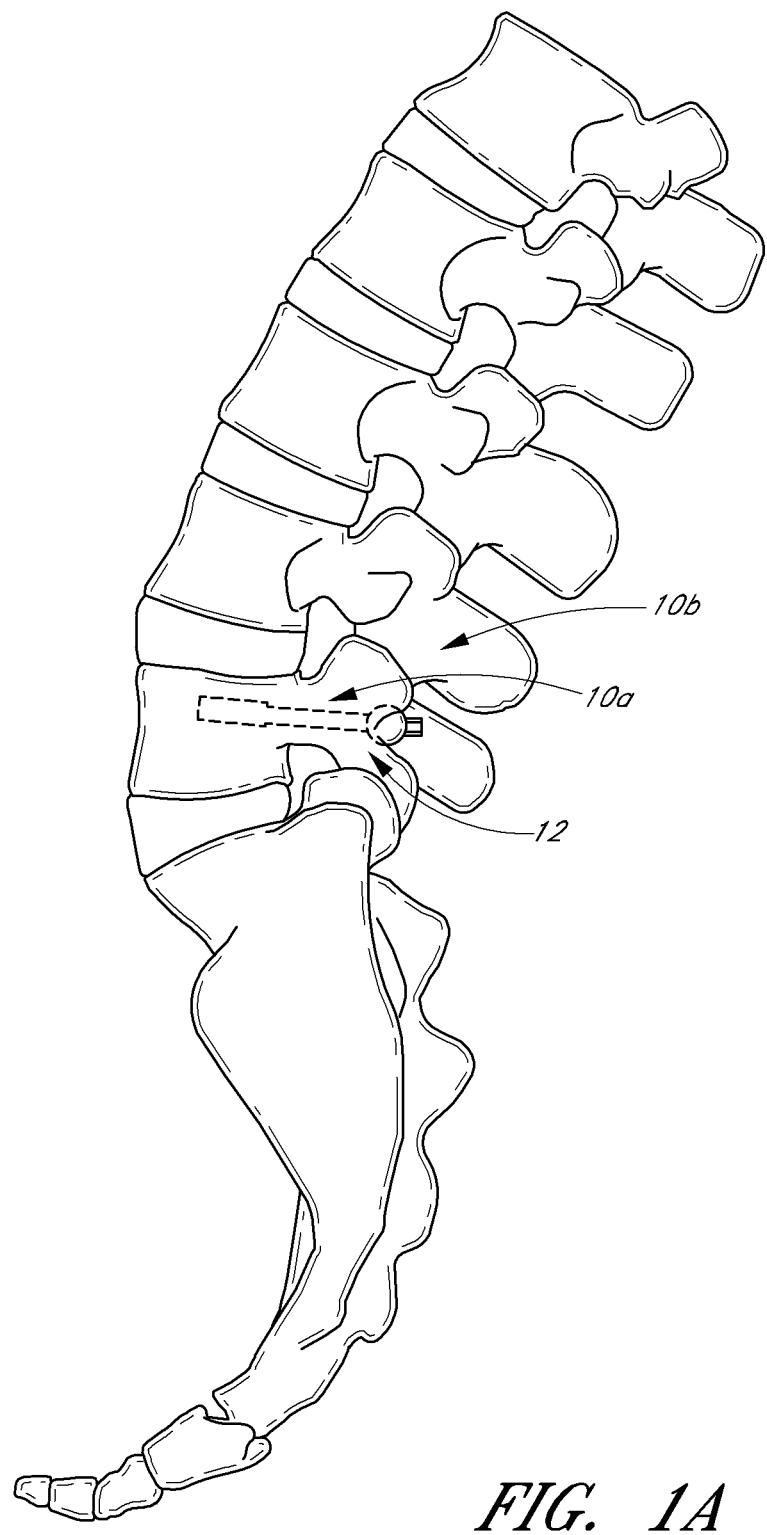
FIG. 1A a side elevational view of a portion of a vertebra in which a stabilization device implanted therein, according to an embodiment of the present inventions.
Figure 1B:
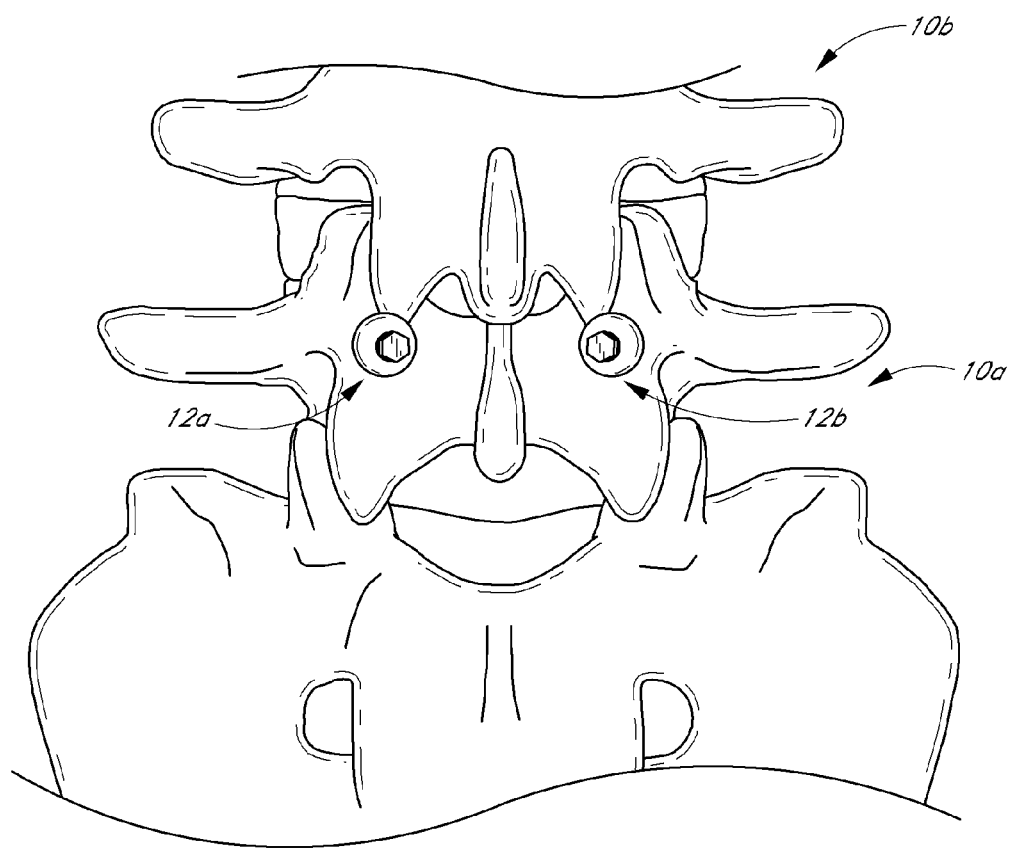
FIG. 1B is a posterior view of a portion of a vertebra having two devices similar to that of FIG. 1A implanted substantially bilaterally therein, according to another embodiment.

FIGS. 1A and 1B are side and rear elevational views of a dynamic stabilization device 12 positioned within a body structure 10a of a spine. FIGS. 1D and 1E are side and rear elevational views of two pair of bone stabilization devices, such as the dynamic stabilization device 12 and a fixation device 800, positioned within body structures 10a, 10b of the spine. As will be explained in detail below, the dynamic stabilization device 12 and the fixation device 800 may be used in a variety of techniques to stabilize the spine. It should also be understood that the dynamic stabilization device 12 and the fixation device 800 may refer to more than one dynamic stabilization device 12 (such as a pair of dynamic stabilization devices 12a, 12b) and more than one fixation device 800 (such as a pair of fixation devices 800a, 800b).

As discussed further herein, in some embodiments, the dynamic stabilization device(s) 12 can include an outer surface of a proximal anchor that has a smooth or spherical shape. As will be explained below, the outer surface of the proximal anchor can be configured to abut against the inferior facet of the superior adjacent vertebrae. In this manner, motion between the adjacent vertebrae may be limited and/or constrained. When combined with the fixation device(s) 800, the devices (12, 800) can be implanted to result in beneficial dynamic stabilization of a desired portion of the spine.

In one embodiment, the dynamic stabilization device 12 can be attached (e.g., inserted or screwed into) and/or coupled to a respective body structures and limit motion of another respective body structure. In the another embodiment, the dynamic stabilization device 12 can limit extension in the spine by being attached and/or coupled to a respective inferior body structure and limiting motion of an adjacent respective superior body structure. As described herein, the superior and inferior body structures can refer to adjacent structures along the spine. When discussing the superior body structure, it will be presumed that when the dynamic stabilization device 12 and the fixation device 800 shown in FIGS. 1D and 1E are both used, the devices 12 can be inserted into an intermediate body structure immediately below the superior body structure.

Further, the fixation device 800 can be inserted into the intermediate and the inferior body structures to secure said body structures together and to promote fusion between the body structures. Thus, the three body structures may be described as superior, intermediate, and inferior when the dynamic stabilization device 12 and the fixation device 800 are discussed together, or as simply superior and inferior when the dynamic stabilization device 12 and the fixation device 800 are being discussed individually. "Body structure" as used herein is the anterior solid segment and the posterior segment of any vertebrae of the five regions (cervical, thoracic, lumbar, sacral, and coccygeal) of the spine. In some embodiments, the dynamic stabilization device 12 can limit motion by contacting, abutting against and/or wedging against the adjacent body structure and/or a device coupled to the adjacent body structure. The fixation device 800 can be positioned below (or above in other embodiments) the stabilization device 12 and can be used to promote spinal fusion below the spinal level at which motion is limited by the dynamic stabilization device. In such an embodiment, the dynamic stabilization device can provide adjacent level support as an adjunct to fusion therapy. In one embodiment, the fusion therapy involves the fixation device 800, which will be described in detail below.

With reference to the illustrated embodiment of FIGS. 1A and 1B, the distal end of the dynamic bone stabilization device 12 is inserted into the pedicle of the inferior vertebrae, preferably through the pars (i.e., the region between the lamina and the superior articular processes). The proximal end of the device 12 extends above the pars such that it limits motion of a superior adjacent vertebra 10b with respect to the inferior adjacent vertebrae 10b. In one embodiment, the proximal end of the device limits motion by abutting and/or wedging against a surface of the superior adjacent vertebrae as the superior adjacent vertebrae moves relative to the inferior adjacent vertebrae. In this manner, at least one degree of motion between the inferior and superior vertebrae may be limited. For example, the spine generally has six (6) degrees of motion which include flexion, extension, left and right lateral bending and axial rotation or torsion. In the illustrated embodiment, extension of the spine is limited. Embodiments in which the devices are inserted with bilateral symmetry can be used to limit left and right lateral bending.

In the illustrated embodiment, motion of the spine is limited when the proximal end of the device contacts, abuts, and/or wedges against the inferior articular process of the superior adjacent vertebra 10b. In this application, it should be appreciated that one or more intermediate member(s) (e.g., plates, platforms, coatings, cement, and/or adhesives) can be can be coupled to the superior adjacent vertebra 10b or other portions of the spine that the device contacts, abuts, and/or wedges against. Thus, in this application, when reference is made to the device contacting, abutting and/or wedging against a portion of the spine it should be appreciated that this includes embodiments in which the device contacts, abuts and/or wedges against one or more intermediate members that are coupled to the spine unless otherwise noted.

As explained below, the bone stabilization devices 12 may be used after laminectomy, discectomy, artificial disc replacement, microdiscectomy, laminotomy and other applications for providing temporary or permanent stability in the spinal column. For example, lateral or central spinal stenosis may be treated with the bone fixation devices 12 and techniques described below. In such procedures, the bone fixation devices 12 and techniques may be used alone or in combination with laminectomy, discectomy, artificial disc replacement, and/or other applications for relieving pain and/or providing stability.

An embodiment of the stabilization device 12 will now be described in detail with initial reference to FIGS. 2-4. The stabilization device 12 comprises a body 28 that extends between a proximal end 30 and a distal end 32. The length, diameter and construction materials of the body 28 can be varied, depending upon the intended clinical application. In embodiments optimized for spinal stabilization in an adult human population, the body 28 will generally be within the range of from about 20-90 mm in length and within the range of from about 3.0-8.5 mm in maximum diameter. The length of the helical anchor, discussed below, may be about 8-80 millimeters. Of course, it is understood that these dimensions are illustrative and that they may be varied as required for a particular patient or procedure.

In one embodiment, the body 28 comprises titanium. However, as will be described in more detail below, other metals, or bioabsorbable or nonabsorbable polymeric materials may be utilized, depending upon the dimensions and desired structural integrity of the finished stabilization device 12.

The distal end 32 of the body 28 is provided with a cancellous bone anchor and/or distal cortical bone anchor 34. Generally, for spinal stabilization, the distal bone anchor 34 is adapted to be rotationally inserted into a portion (e.g., the pars or pedicle) of a first vertebra. In the illustrated embodiment, the distal anchor 34 comprises a helical locking structure 72 for engaging cancellous and/or distal cortical bone. In the illustrated embodiment, the locking structure 72 comprises a flange that is wrapped around a central core 73, which in the illustrated embodiment is generally cylindrical in shape. The flange 72 extends through at least one and generally from about two to about 50 or more full revolutions depending upon the axial length of the distal anchor 34 and intended application. The flange will generally complete from about 2 to about 60 revolutions. The helical flange 72 is preferably provided with a pitch and an axial spacing to optimize the retention force within cancellous bone. While the helical locking structure 72 is generally preferred for the distal anchor, it should be appreciated that the distal anchor could comprise other structures configured to secure the device in the cancellous bone anchor and/or distal cortical bone, such as, for example, various combinations and sub-combinations of hooks, prongs, expandable flanges, etc. See also e.g., U.S. Pat. No. 6,648,890, the entirety of which is hereby incorporated by reference herein.

Figure 3A:
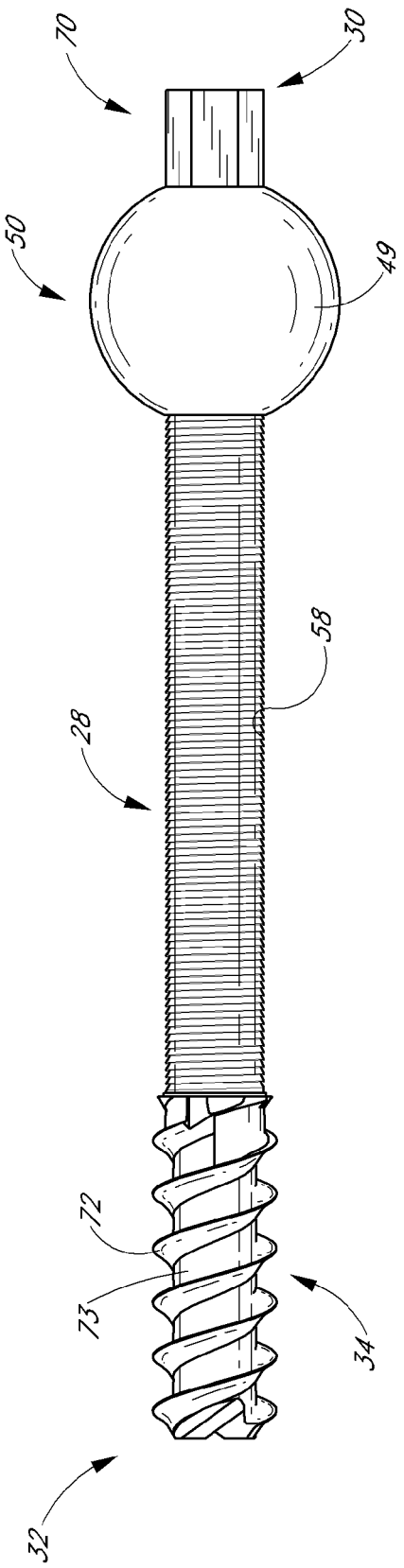
FIG. 3A is a side view of the stabilization device shown in FIG. 2.
Figure 3B:
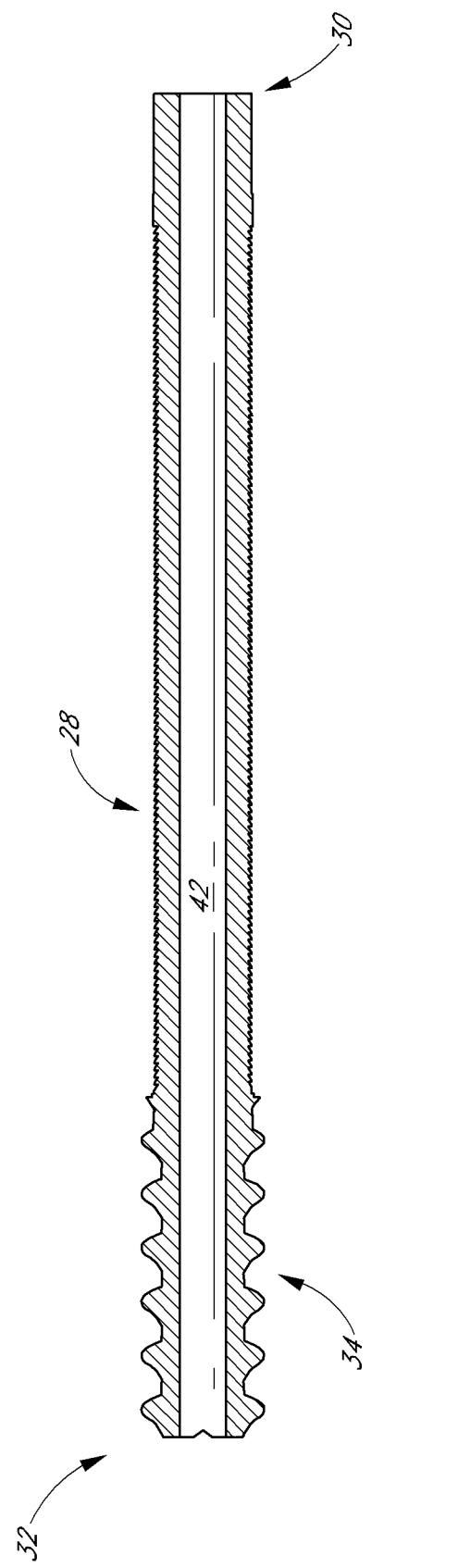
FIG. 3B is a cross-sectional view of a body portion of the stabilization device of FIG. 2.

The helical flange 72 of the illustrated embodiment has a generally triangular cross-sectional shape (see FIG. 3B). However, it should be appreciated that the helical flange 72 can have any of a variety of cross sectional shapes, such as rectangular, oval or other as deemed desirable for a particular application through routine experimentation in view of the disclosure herein. For example, in one modified embodiment, the flange 72 has a triangular cross-sectional shape with a blunted or square apex. One particularly advantageous cross-sectional shape of the flange are the blunted or square type shapes. Such shapes can reduce cutting into the bone as the proximal end of the device is activated against causing a windshield wiper effect that can loosen the device 12. The outer edge of the helical flange 72 defines an outer boundary. The ratio of the diameter of the outer boundary to the diameter of the central core 73 can be optimized with respect to the desired retention force within the cancellous bone and giving due consideration to the structural integrity and strength of the distal anchor 34. Another aspect of the distal anchor 34 that can be optimized is the shape of the outer boundary and the central core 73, which in the illustrated embodiment are generally cylindrical.

The distal end 32 and/or the outer edges of the helical flange 72 may be atraumatic (e.g., blunt or soft). This inhibits the tendency of the stabilization device 12 to migrate anatomically distally and potentially out of the vertebrae after implantation. Distal migration is also inhibited by the dimensions and presence of a proximal anchor 50, which will be described below. In the spinal column, distal migration is particularly disadvantageous because the distal anchor 34 may harm the tissue, nerves, blood vessels and/or spinal cord which lie within and/or surround the spine. Such features also reduce the tendency of the distal anchor to cut into the bone during the "window-wiper effect" that is caused by cyclic loading of the device as will be described. In other embodiments, the distal end 32 and/or the outer edges of the helical flange 72 may be sharp and/or configured such that the distal anchor 34 is self tapping and/or self drilling.

A variety of other embodiments for the distal anchor 32 can also be used. For example, the various distal anchors described in U.S. Pat. No. 6,908,465, issued Jun. 21, 2005 can be incorporated into the stabilization device 12 described herein. The entire contents of this application are hereby expressly incorporated by reference. In particular, the distal anchor 32 may comprise a single helical thread surrounding a lumen, much as in a conventional corkscrew. Alternatively, a double helical thread may be utilized, with the distal end of the first thread rotationally offset from the distal end of the second thread. The use of a double helical thread can enable a greater axial travel for a given degree of rotation and greater retention force than a corresponding single helical thread. Specific distal anchor designs can be optimized for the intended use, taking into account desired performance characteristics, the integrity of the distal bone, and whether the distal anchor is intended to engage exclusively cancellous bone or will also engage cortical bone. In still other embodiments, the distal anchor 34 may be formed without a helical flange. For example, various embodiments of levers, prongs, hooks and/or radially expandable devices may also be used. See e.g., U.S. Pat. No. 6,648,890, which is hereby expressly incorporated by reference in its entirety.

As shown in FIG. 3B, the body 28 is cannulated forming a central lumen 42 to accommodate installation over a placement wire as is understood in the art. The cross section of the illustrated central lumen is circular but in other embodiments may be non circular, e.g., hexagonal, to accommodate a corresponding male tool for installation or removal of the body 28 as explained below. In other embodiments, the body 28 may be partially or wholly solid.

Figure 2:
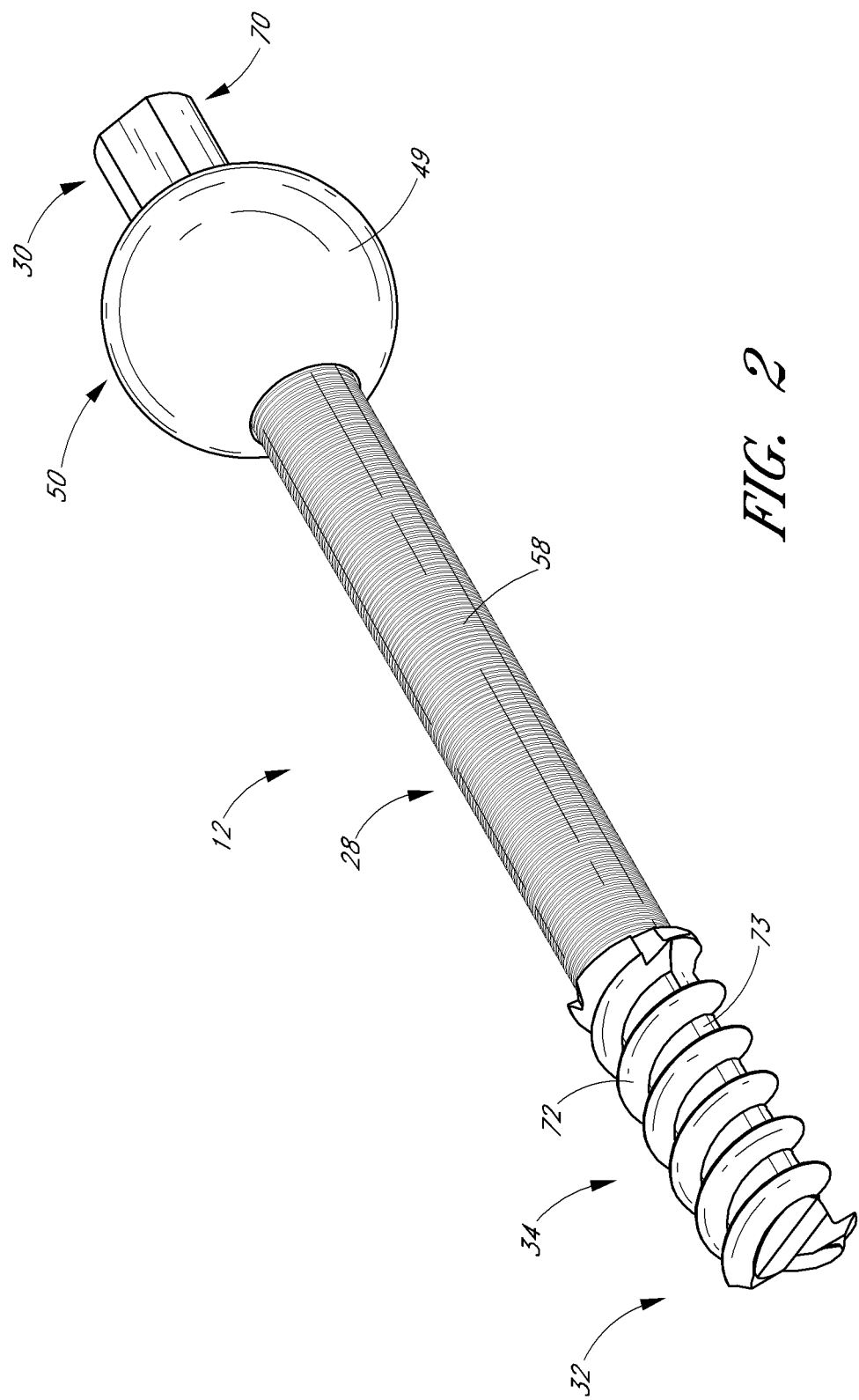
FIG. 2 is a side perspective view of the stabilization device of FIGS. 1A and 1B, according to an embodiment.
Figure 4:
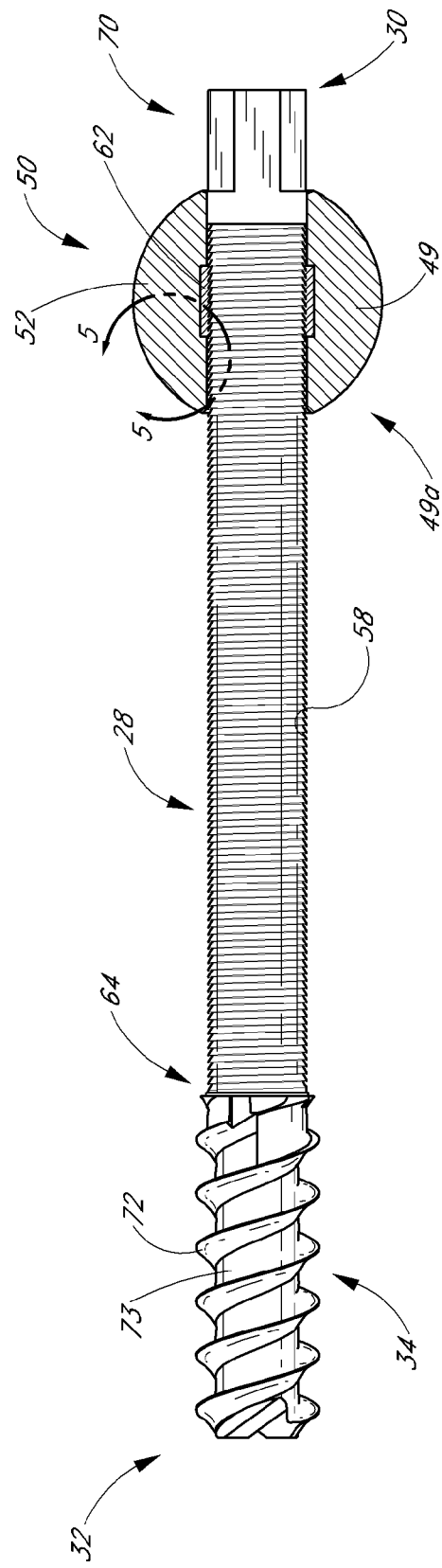
FIG. 4 is a partial cross-sectional view of a proximal portion of the stabilization device shown in FIG. 2.

With continued reference to FIGS. 2-4, the proximal end 30 of the body 28 is provided with a rotational coupling 70, for allowing the body 28 to be rotated. Rotation of the rotational coupling 70 can be utilized to rotationally drive the distal anchor 32 into the bone. In such embodiments, any of a variety of rotation devices may be utilized, such as electric drills or hand tools, which allow the clinician to manually rotate the proximal end 30 of the body 28. Thus, the rotational coupling 70 may have any of a variety of cross sectional configurations, such as one or more curved faces, flats, or splines. In the illustrated embodiment, the rotational coupling 70 is a male element in the form of a hexagonal projection. However, in other embodiments, the rotational coupling 70 may be in the form of a female component, machined, milled or attached to the proximal end 30 of the body 28. For example, in one such embodiment, the rotational coupling 70 comprises an axial recess with a polygonal cross section, such as a hexagonal cross section. As explained above, the axial recess may be provided as part of the central lumen 42.

The proximal end 30 of the fixation device is also provided with a proximal anchor 50. The proximal anchor 50 comprises a housing 52, which forms a lumen 53 (see FIG. 5) configured such that the body 28 may extend, at least partially, through the proximal anchor 50. The proximal anchor 50 is axially distally moveable along the body 28 such that the proximal anchor 50 can be properly placed with respect to the inferior vertebra and superior vertebra. As will be explained below, complimentary locking structures such as threads, levers, split rings, and/or ratchet like structures between the proximal anchor 50 and the body 28 resist proximal movement of the anchor 50 with respect to the body 28 under normal use conditions. The proximal anchor 50 preferably can be axially advanced along the body 28 with and/or without rotation as will be apparent from the disclosure herein.

Figure 5:
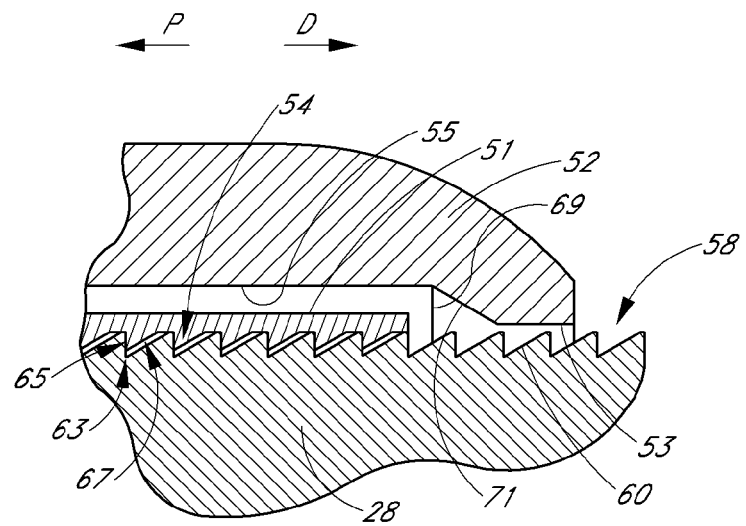
FIG. 5 is an enlarged view of a portion of the stabilization device shown in FIG. 4 taken along section 5-5.
Figure 6:
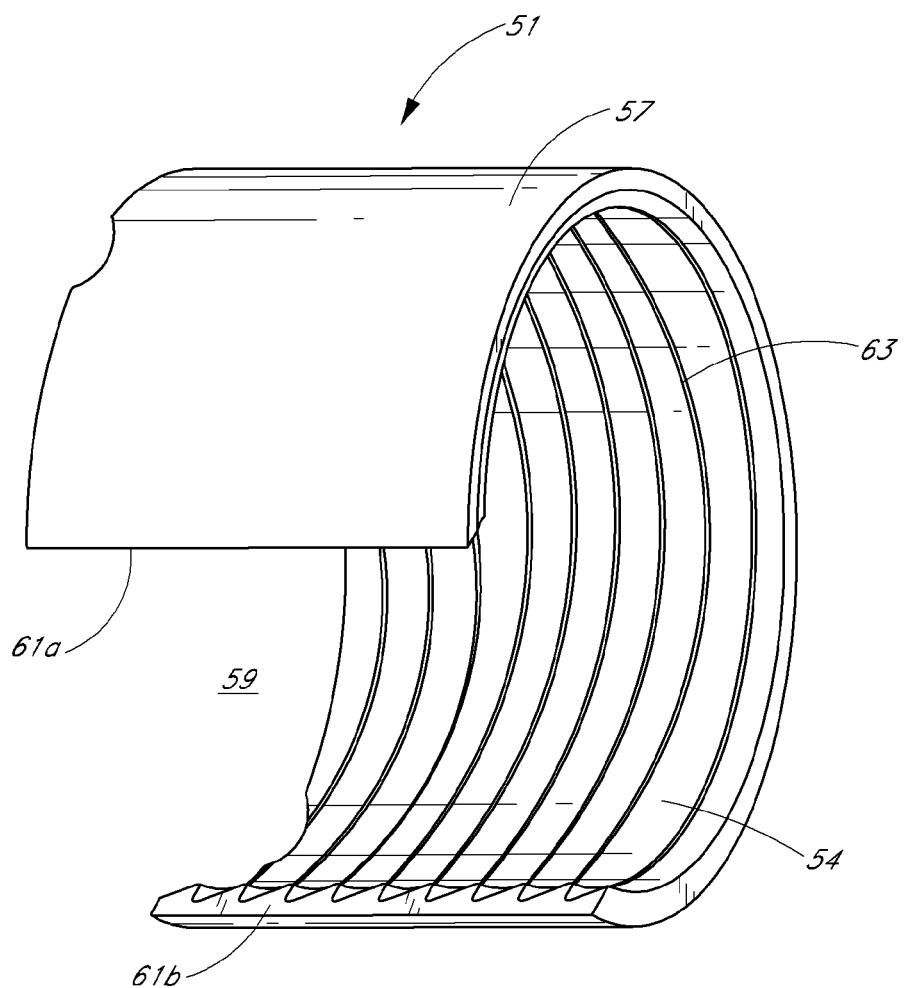
FIG. 6 is a side perspective view of a locking ring of the stabilization device shown in FIG. 3A.

With particular reference to FIGS. 4-6, in the illustrated embodiment, the complementary structure of the proximal anchor 50 is formed by an annular ring 51, which is positioned within an annular recess 55 formed along the lumen 53. As will be explained below, the ring 51 comprises surface structures 54 which interact with complimentary surface structures 58 on the body 28. In the illustrated embodiment, the complimentary surface structures 58 comprise a series of annular ridges or grooves 60 formed on the surface of the body 28. The surface structures 54 and complementary surface structures 58 permit distal axial travel of the proximal anchor 50 with respect to the body 28, but resist proximal travel of the proximal anchor 50 with respect to the body 28 as explained below.

As shown in FIG. 6, the annular ring 51 is split (i.e., has a least one gap) and is interposed between the body 28 and the recess 55 of the proximal anchor 50 (see FIG. 5). In the illustrated embodiment, the ring 51 comprises a tubular housing 57 (see FIG. 6), which defines a gap or space 59. In one embodiment, the gap 59 is defined by a pair of edges 61a, 61b, that are generally straight and parallel to each other. Although not illustrated, it should be appreciated that in modified embodiments, the ring 51 can be formed without a gap. When the ring 51 is positioned along the body 28, the ring 51 preferably surrounds a substantial portion of the body 28. The ring 51 can be configured so that the ring 51 can flex or move radially outwardly in response to an axial force so that the ring 51 can be moved relative to the body 28, as described below.

In the illustrated embodiment, the tubular housing 57 includes at least one and in the illustrated embodiment ten teeth or flanges 63, which are configured to engage the complementary surface structures 58 on the body 28 in a ratchet-like motion. In the illustrated embodiment (see FIG. 5), the teeth or flanges include a first surface 65 that lies generally perpendicular to the longitudinal axis of the anchor and generally faces the proximal direction (i.e., the direction labeled "P" in FIG. 5) and a second surface 67 that is inclined with respect to the longitudinal axis of the anchor and that faces distal direction (i.e., the direction labeled "D" in FIG. 5). It should be noted that the proximal and directions in FIG. 5 are reversed with respect to FIG. 4.

With continued reference to FIG. 5, the recess 55 is sized and dimensioned such that as the proximal anchor 50 is advanced distally over the body, the second surface 67 of the annular ring 51 can slide along and over the complementary retention structures 58 of the body 28. That is, the recess 55 provides a space for the annular ring to move radially away from the body 28 as the proximal anchor 50 is advanced distally.

A distal portion 69 of the recess 55 is sized and dimensioned such that after the proximal anchor 50 is appropriately advanced, proximal motion of the proximal anchor 50 is resisted as the annular ring 51 becomes wedged between the body 28 and an angled engagement surface 71 of the distal portion 69. In this manner, proximal movement of the proximal anchor 50 under normal use conditions may be prevented. In modified embodiments, the annular ring 51 can be sized and dimensioned such that the ring 51 is biased inwardly to engage the retention structures 58 on the body 28. The bias of the annular ring 51 can result in a more effective engagement between the complementary retention structures 58 of the body and the retention structures 54 of the ring 51.

In certain embodiments, it is advantageous for the outer surface 49 of the proximal anchor 50 to rotate with respect to the body 28. This arrangement advantageously reduces the tendency of the body 28 to rotate and/or move within the superior articular process of the inferior vertebrae 10*a* as the outer surface 49 contacts, abuts or wedges against the inferior articular process of the superior vertebrae 10*b*. In the illustrated embodiment, rotation of the outer surface 49 is provided by configuring the lumen 53 and annular recess 55 such that the anchor 50 can rotate about the body 28 and ring 51. Preferably, as the anchor 50 rotates the axial position of the anchor 50 with respect to the body 28 remains fixed. That is, the annular ring 51 resists proximal travel of the proximal anchor 50 with respect to the body 28 while the anchor 50 is permitted to rotate about the body 28 and ring 51. Of course those of skill in the art will recognize other configurations and mechanisms (e.g., bearings, rollers, slip rings, etc.) for providing rotation of the outer surface 49 with respect to the body 28. In a modified embodiment, the proximal anchor 50 can be configured such that it does not rotate with respect to the body 28. In such an embodiment, a key or one or more anti-rotational features (e.g., splines, grooves, flat sides, etc.) can be provided between the proximal anchor 50, the ring 51 and/or the body 51 to limit or prevent rotation of the proximal anchor 50 with respect to the body 28.

As mentioned above, it is contemplated that various other retention structures 54 and complementary retention structures 58 may be used between the body 28 and the proximal anchor 50 to permit distal axial travel of the proximal anchor 50 with respect to the body 28, but resist proximal travel of the proximal anchor 50 with respect to the body 28. Examples of such structures can be found in U.S. Pat. No. 6,685,706, entitled "PROXIMAL ANCHORS FOR BONE FIXATION SYSTEM." The entire contents of U.S. Pat. No. 6,685,706 are hereby expressly incorporated by reference herein. In such embodiments, the structures 54 and complementary retention structures 58 can be configured to allow the proximal anchor to be advanced with or without rotation with respect to the body 28.

As mentioned above, the complimentary surface structures 58 on the body 28 comprise threads, and/or a series of annular ridges or grooves 60. These retention structures 58 are spaced axially apart along the body 28, between a proximal limit 62 and a distal limit 64. See FIG. 4. The axial distance between proximal limit 62 and distal limit 64 is related to the desired axial working range of the proximal anchor 50, and thus the range of functional sizes of the stabilization device 12. Thus, the stabilization device 12 of the example embodiment can provide accurate placement between the distal anchor 34 and the proximal anchor 50 throughout a range of motion following the placement of the distal anchor in a vertebra. That is, the distal anchor 34 may be positioned within the cancellous and/or distal cortical bone of a vertebra, and the proximal anchor may be distally advanced with respect to the distal anchor throughout a range to provide accurate placement of the proximal anchor 50 with respect to the vertebra without needing to relocate the distal anchor 34 and without needing to initially locate the distal anchor 34 in a precise position with respect to the proximal side of the bone or another vertebra. The arrangement also allows the compression between the distal anchor 34 and the proximal anchor 50 to be adjusted. Providing a working range throughout which positioning of the proximal anchor 50 is independent from setting the distal anchor 34 allows a single device to be useful for a wide variety of different anatomies, as well as eliminates or reduces the need for accurate device measurement. In addition, this arrangement allows the clinician to adjust the compression force during the procedure without adjusting the position of the distal anchor. In this manner, the clinician may focus on positioning the distal anchor sufficiently within the vertebra to avoid or reduce the potential for distal migration out of the vertebra, which may damage the particularly delicate tissue, blood vessels, nerves and/or spinal cord surrounding or within the spinal column. In addition or alternative, the above described arrangement allows the clinician to adjust the positioning of the proximal anchor 50 with respect to the inferior articular process of the superior adjacent vertebrae. In this manner, the clinician may adjust the position of the proximal anchor 50 without adjusting the position of the distal anchor such that the anchor 50 is configured to wedge or abut against inferior articular process of the superior adjacent vertebrae. In a modified embodiment, the position of the proximal anchor 50 with respect to the surrounding vertebra can be adjusted by rotating the device 12 and advancing the distal anchor and the proximal anchor carried by the body.

In the embodiment of FIGS. 4-6, the proximal anchor 50 can be distally advanced over the body 28 without rotating the proximal anchor 50 with respect to the body 28. In one embodiment, the ring 51 and the proximal anchor 50 are rotationally linked by, for example, providing inter-engaging structures (e.g., tabs, ridges and the like). In such an embodiment, the proximal anchor 50 can be advanced without rotating the proximal anchor 50 and be removed and/or the position adjusted in a proximal or distal direction by rotating the proximal anchor with respect to the body 28. This can allow the surgeon to remove an proximal anchor and use a different sized or configured proximal anchor 50 if the first proximal anchor is determined to be inadequate. In such an embodiment, the proximal anchor 50 is preferably provided with one or more engagement structures (e.g., slots, hexes, recesses, protrusions, etc.) configured to engage a rotational and/or gripping device (e.g., slots, hexes, recesses, protrusions, etc.). Thus, in some embodiments, the proximal anchor 50 can be pulled and/or rotated such that the anchor 50 is removed from the body.

In many applications, the working range is at least about 10% of the overall length of the device, and may be as much as 20% or 50% or more of the overall device length. In the context of a spinal application, working ranges of up to about 10 mm or more may be provided, since estimates within that range can normally be readily accomplished within the clinical setting. The embodiments disclosed herein can be scaled to have a greater or a lesser working range, as will be apparent to those of skill in the art in view of the disclosure herein.

In embodiments optimized for spinal stabilization in an adult human population, the anchor 50 will have a diameter within the range of from about 1 to $\frac{1}{16}$ of an inch in another embodiment the proximal anchor proximal anchor 50 within the range from about 0.5 to $\frac{1}{8}$ of an inch in another embodiment.

With reference back to FIGS. 2-4, in the illustrated embodiment, the outer surface 49 of the proximal anchor 50 has a smooth or spherical shape. As will be explained below, the outer surface 49 of the proximal anchor 50 is configured to abut against the inferior facet of the superior adjacent vertebrae. In this manner, motion between the adjacent vertebrae may be limited and/or constrained.

Figure 7A:
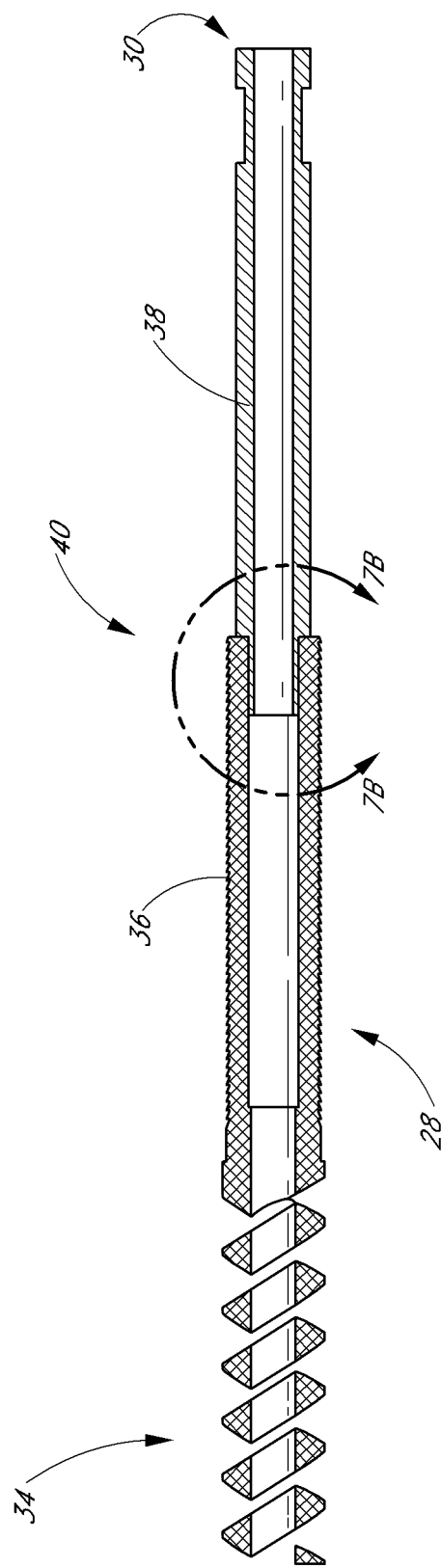
FIG. 7A is a side view of a body portion of the stabilization device shown in FIG. 2, according to another embodiment.

FIG. 7A illustrates an embodiment in which the body 28 comprises a first portion 36 and a second portion 38 that are coupled together at a junction 40. In the illustrated embodiment, the first portion 36 carries the distal anchor 34 (shown without a central core) while the second portion 38 forms the proximal end 30 of the body 28. As will be explained in more detail below, in certain embodiments, the second portion 38 may be used to pull the body 28 and therefore will sometimes be referred to as a "pull-pin." The first and second portions 36, 38 are preferably detachably coupled to each other at the junction 40. In the illustrated embodiment, the first and second portions 36, 38 are detachably coupled to each other via interlocking threads.

Figure 7B:
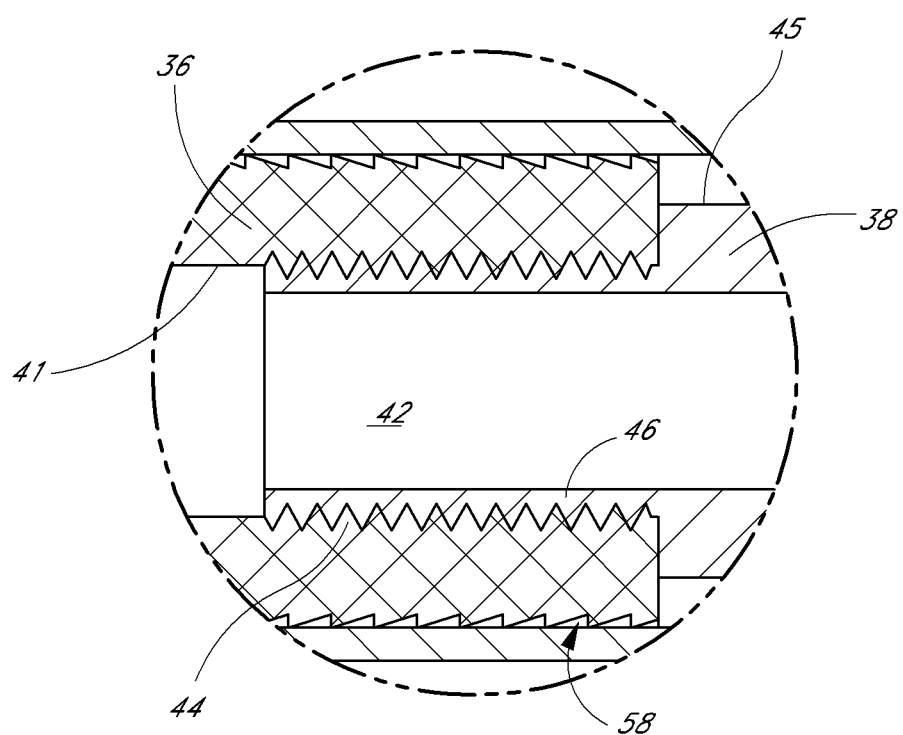
FIG. 7B is an enlarged view of a portion of the stabilization device shown in FIG. 7A taken along section 7B-7B.

Specifically, as best seen in FIG. 7B, the body 28 includes an inner surface 41, which defines a central lumen 42 that preferably extends from the proximal end 30 to the distal end 32 throughout the body 28. At the proximal end of the first portion 36, the inner surface 41 includes a first threaded portion 44. The first threaded portion 44 is configured to mate with a second threaded portion 46, which is located on the outer surface 45 of the second portion 38. The interlocking annular threads of the first and second threaded portions 44, 46 allow the first and second portions 36, 38 to be detachably coupled to each other. In one modified embodiment, the orientation of the first and second threaded portions 44, 46 can be reversed. That is, the first threaded portion 44 can be located on the outer surface of the first portion 36 and the second threaded portion 46 can be located on the inner surface 41 at the distal end of the second portion 38. Any of a variety of other releasable complementary engagement structures may also be used, to allow removal of second portion 38 following implantation, as is discussed below.

In a modified arrangement, the second portion 38 can comprise any of a variety of tensioning elements for permitting proximal tension to be placed on the distal anchor 34 while the proximal anchor is advanced distally. For example, any of a variety of tubes or wires can be removably attached to the first portion 36 and extend proximally to the proximal handpiece. In one such arrangement, the first portion 36 can include a releasable connector in the form of a latching element, such as an eye or hook. The second portion 38 can include a complementary releasable connector (e.g., a complementary hook) for engaging the first portion 36. In this manner, the second portion 38 can be detachably coupled to the first portion 36 such proximal traction can be applied to the first portion 36 through the second portion as will be explained below. Alternatively, the second portion 48 may be provided with an eye or hook, or transverse bar, around which or through which a suture or wire may be advanced, both ends of which are retained at the proximal end of the device. Following proximal tension on the tensioning element during the compression and/or positioning step, one end of the suture or wire is released, and the other end may be pulled free of the device. Alternate releasable proximal tensioning structures may be devised by those of skill in the art in view of the disclosure herein.

In a final position, the distal end of the proximal anchor 50 preferably extends distally past the junction 40 between the first portion 36 and the second portion 38. As explained above, the proximal anchor 50 is provided with one or more surface structures 54 for cooperating with complementary surface structures 58 on the first portion 36 of the body 28.

In this embodiment, the stabilization device 12 may include an antirotation lock (not shown) between the first portion 36 of the body 28 and the proximal collar 50. For example, the first portion 36 may include one or more of flat sides (not shown), which interact with corresponding flat structures in the proximal collar 50. As such, rotation of the proximal collar 50 is transmitted to the first portion 36 and distal anchor 34 of the body 28. Of course, those of skill in the art will recognize various other types of splines or other interfit structures can be used to prevent relative rotation of the proximal anchor and the first portion 36 of the body 28. To rotate the proximal anchor 50, the housing 52 may be provided with a gripping structure (not shown) to permit an insertion tool to rotate the flange proximal anchor 50. Any of a variety of gripping structures may be provided, such as one or more slots, recesses, protrusions, flats, bores or the like. In one embodiment, the proximal end of the proximal anchor 50 is provided with a polygonal, and, in particular, a pentagonal or hexagonal recess or protrusion.

Methods implanting stabilization devices described above as part of a spinal stabilization procedure will now be described. Although certain aspects and features of the methods and instruments described herein can be utilized in an open surgical procedure, the disclosed methods and instruments are optimized in the context of a percutaneous or minimally invasive approach in which the procedure is done through one or more percutaneous small openings. Thus, the method steps which follow and those disclosed are intended for use in a trans-tissue approach. However, to simplify the illustrations, the soft tissue adjacent the treatment site have not been illustrated in the drawings.

In one embodiment of use, a patient with a spinal instability is identified. The patient is preferably positioned face down on an operating table, placing the spinal column into a normal or flexed position. A trocar optionally may then be inserted through a tissue tract and advanced towards a first vertebra. In another embodiment, biopsy needle (e.g., Jamshidi™) device can be used. A guidewire may then be advanced through the trocar (or directly through the tissue, for example, in an open surgical procedure) and into the first vertebra. With reference to FIG. 1D, the guide wire 110 is preferably inserted into the pedicle of the vertebrae preferably through the pars (i.e. the region of the lamina between the superior and inferior articular processes).

With reference to FIG. 1E, a suitable expandable access sheath or dilator 112 can then be inserted over the guidewire and expanded (FIG. 1F) to enlarge the tissue tract and provide an access lumen for performing the methods described below in a minimally invasive manner. In a modified embodiment, a suitable tissue expander (e.g., a balloon expanded catheter or a series of radially enlarged sheaths) can be inserted over the guidewire and expanded to enlarge the tissue tract. A surgical sheath can then be advanced over the expanded tissue expander. The tissue expander can then be removed such that the surgical sheath provides an enlarged access lumen. Any of a variety of expandable access sheaths or tissue expanders can be used, such as, for example, a balloon expanded catheter, a series of radially enlarged sheaths inserted over each other, and/or the dilation introducer described in U.S. patent application Ser. No. 11/038,784, filed Jan. 19, 2005 (Publication No. 2005/0256525), the entirety of which is hereby incorporated by reference herein.

A drill with a rotatable tip may be advanced over the guidewire and through the sheath. The drill may be used to drill an opening in the vertebrae. The opening may be configured for (i) for insertion of the body 28 of the bone stabilization device 12, (ii) tapering and/or (iii) providing a counter sink for the proximal anchor 50. In other embodiments, the step of drilling may be omitted. In such embodiments, the distal anchor 34 is preferably self-tapping and self drilling. In embodiments, in which an opening is formed, a wire or other instrument may be inserted into the opening and used to measure the desired length of the body 28 of the device 12.

The body 28 of the fixation device may be advanced over the guidewire and through the sheath until it engages the vertebrae. The body 28 may be coupled to a suitable insertion tool prior to the step of engaging the fixation device 12 with the vertebrae. The insertion tool may be configured to engage the coupling 70 on the proximal end of the body 28 such that insertion tool may be used to rotate the body 28. In such an embodiment, the fixation device 12 is preferably configured such that it can also be advanced over the guidewire.

The insertion tool may be used to rotate the body 28 thereby driving the distal anchor 34 to the desired depth within the pedicle of the vertebra. The proximal anchor 50 may be carried by the fixation device prior to advancing the body 28 into the vertebra, or may be attached and/or coupled to the body 28 following placement (partially or fully) of the body 28 within the vertebrae. In another embodiment, the anchor 50 may be pre-attached and/or coupled to the body 28.

In one embodiment, the clinician will have access to an array of devices 12, having, for example, different diameters, axial lengths, configurations and/or shapes. The clinician will assess the position of the body 28 with respect to the superior vertebrae and choose the device 12 from the array, which best fits the patient anatomy to achieve the desired clinical result. In another embodiment, the clinician will have access to an array of devices 12, having, for example, bodies 28 of different diameters, axial lengths. The clinician will also have an array of proximal anchors 50, having, for example, different configurations and/or shapes. The clinician will choose the appropriate body 28 and then assess the position of the body 28 with respect to the superior vertebrae and choose the proximal anchor 50 from the array, which best fits the patient anatomy to achieve the desired clinical result. In such an embodiment, the proximal anchor 50 is advantageously coupled to body 28 after the body 28 is partially or fully inserted into the vertebrae.

Once the distal anchor 34 is in the desired location, the proximal anchor 50 is preferably advanced over the body 28 until it reaches its desired position. This may be accomplished by pushing on the proximal anchor 50 or by applying a distal force to the proximal anchor 50. In another embodiment, the proximal anchor 50 is advanced by applying a proximal retraction force to the proximal end 30 of body 28, such as by conventional hemostats, pliers or a calibrated loading device, while distal force is applied to the proximal anchor 50. In this manner, the proximal anchor 50 is advanced distally with respect to the body 28 until the proximal anchor 50 is in its proper position (e.g., positioned snugly against the outer surface of the vertebra). Appropriate tensioning of the stabilization device 12 can be accomplished by tactile feedback or through the use of a calibration device for applying a predetermined load on the stabilization device 12. As explained above, one advantage of the structure of the illustrated embodiments is the ability to adjust the compression and/or the position of the proximal anchor 50 independently of the setting of the distal anchor 34 within the vertebra. For example, the positioning of the distal anchor 34 within the vertebra can be decoupled from the positioning of the proximal anchor 50 with respect to the superior vertebra.

In one embodiment, the proximal anchor 50 is pushed over the body 28 by tapping the device with a slap hammer or similar device that can be used over a guidewire. In this manner, the distal end of the device 12 is advantageously minimally disturbed, which prevents (or minimizes) the threads in the bore from being stripped.

Following appropriate tensioning of the proximal anchor 50, the proximal portion of the body 28 extending proximally from the proximal anchor 50 can be removed. In one embodiment, this may involve cutting the proximal end of the body 28. For example, the proximal end of the body may be separated by a cutting instrument or by cauterizing. Cauterizing may fuse the proximal anchor 50 to the distal end 32 of the body 28 thereby adding to the retention force between the proximal anchor 50 and the body 28. Such fusion between the proximal anchor and the body may be particularly advantageous if the pin and the proximal anchor are made from a polymeric or plastic material. In this manner, as the material of the proximal anchor and/or the pin is absorbed or degrades, the fusion caused by the cauterizing continues to provide retention force between the proximal anchor and the body. In another embodiment, the body comprises a first and a second portion 36, 38 as described above. In such an embodiment, the second portion 38 may detached from the first portion 36 and removed. In the illustrated embodiment, this involves rotating the second portion 38 with respect to the first portion via the coupling 70. In still other embodiments, the proximal end of the body 28 may remain attached to the body 28.

The access site may be closed and dressed in accordance with conventional wound closure techniques and the steps described above may be repeated on the other side of the vertebrae for substantial bilateral symmetry as shown in FIGS. 1A and 1B. The bone stabilization devices 12 may be used alone or in combination with other surgical procedures such as laminectomy, discectomy, artificial disc replacement, and/or other applications for relieving pain and/or providing stability.

As will be described in detail below, the dynamic stabilization device 12 can provide adjacent level support as an adjunct to fusion therapy. In one embodiment, the fusion therapy involves the fixation device 800, which will be described in detail below. The fixation device 800 can be positioned below (or above in other embodiments) the stabilization device 12 and can be used to promote spinal fusion below the spinal level at which motion is limited by the dynamic stabilization device. In other embodiments, fusion can be promoted using other devices.

As will be explained below, the superior body structure (e.g., the superior vertebrae 10b) can be conformed to the device by providing a complementary surface or interface. In one embodiment, the superior vertebrae can be modified using a separate drill or reamer that is also used to form the countersink 200 described above. In other embodiments, the drill that is used to form an opening in the inferior body can be provided with a countersink portion that is also used to modify the shape of the superior vertebrae 10b. In still other embodiments, the shape of the superior vertebrae 10b can be modified using files, burrs and other bone cutting or resurfacing devices to form a complementary surface or interface for the proximal anchor 50.

Figure 8:
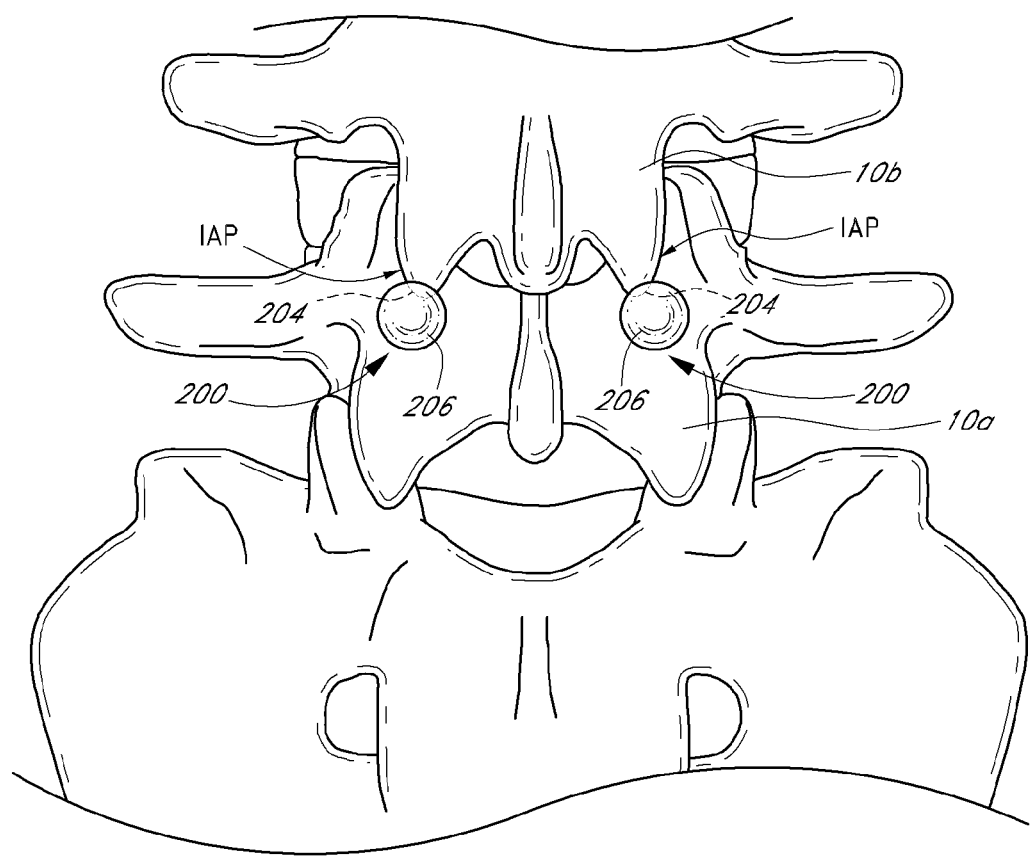
FIG. 8 is a posterior view of a portion of a vertebra having portions thereof removed to receive a fixation device, according to another embodiment.

As mentioned above, a countersink can be provided for the proximal anchor 50. With reference to FIG. 8, a pair of counter sinks 200 is shown formed in or near the pars of the inferior vertebrae 10a. Each counter sink 200 is preferably configured to generally correspond to a distal facing portion 49a (see FIG. 4 or FIG. 10A) of the proximal anchor 50. In this manner, the proximal anchor 50, in a final position, may be seated at least partially within the inferior vertebrae 10a. In the illustrated embodiment, the countersink 200 has a generally spherical configuration that corresponds generally to the spherical shape of the distal portion 49a of the proximal anchor 50 of the illustrated embodiment. In modified embodiments, the countersink 200 can have a modified shape (e.g., generally cylindrical, conical, rectangular, etc.) and/or generally configured to correspond to the distal portion of a proximal anchor 50 with a different shape than the proximal anchor illustrated in FIGS. 2-4.

The countersink 200 advantageously disperses the forces received by the proximal anchor 50 by the superior vertebrae 10b and transmits said forces to the inferior vertebrae 10a. As will be explained in more detail below, the countersink 200 can be formed by a separate drilling instrument or by providing a counter sink portion on a surgical drill used to from a opening in the body 10b.

In addition or in the alternative to creating the countersink 200, the shape of the inferior articular process IAP (which can include the facet in certain embodiments) of the superior vertebrae 10b may be modified in order to also disperse the forces generated by the proximal anchor 50 contacting, abutting and/or wedging against the superior vertebrae 10b. For example, as shown in FIG. 8, a portion 204 of the inferior articular process IAP of the superior vertebrae 10b that generally faces the proximal anchor 50 can be removed with the goal of dispersing and/or reducing the forces applied to the proximal anchor 50. In the illustrated embodiment, the inferior articular process is provided with a generally rounded recess 206 that corresponds generally to the rounded outer surface 49 of the proximal anchor 50. In modified embodiments, the inferior articular process IAP can be formed into other shapes in light of the general goal to reduce and/or disperse the forces applied to the proximal anchor 50. For example, in certain embodiments, the inferior articular process IAP may be formed into a generally flat, blunt or curved shape. In other embodiments, the inferior articular process IAP may be configured to abut and/or wedge more efficiently with a proximal anchor 50 of a different shape (e.g., square, oval, etc.). In general, the countersink 200 and surface 206 provide for an increased contact surface between the superior vertebra and the proximal anchor 50 and the inferior vertebra and the proximal anchor 50. This contact area reduces stress risers in the device and the associated contact areas of the vertebrae. In addition, the windshield wiper affect is reduced as the forces transmitted to the proximal anchor 50 from the superior vertebrae are transmitted through the area formed by the countersink 200.

Figure 9A:
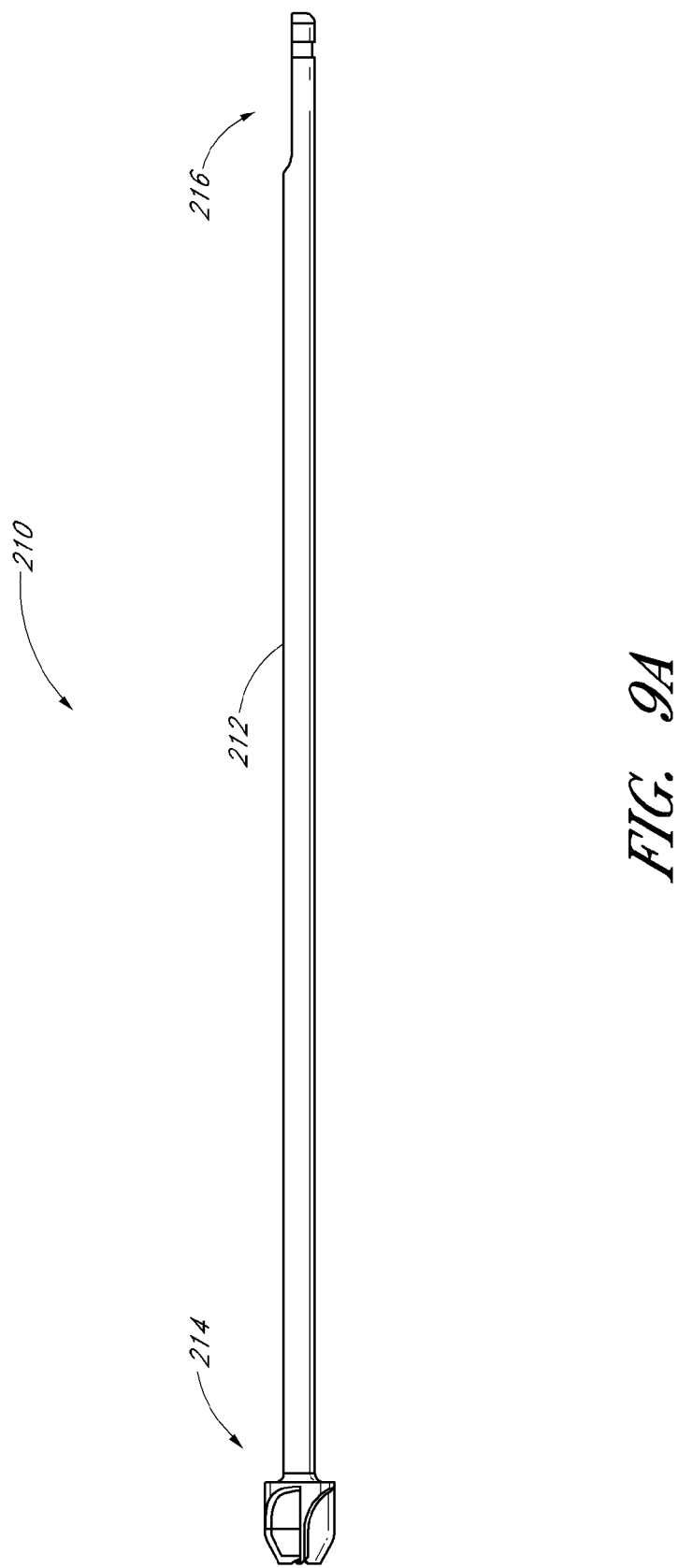
FIG. 9A is a side view of a device configured to remove portions of a vertebra, according to an embodiment.
Figure 9B:
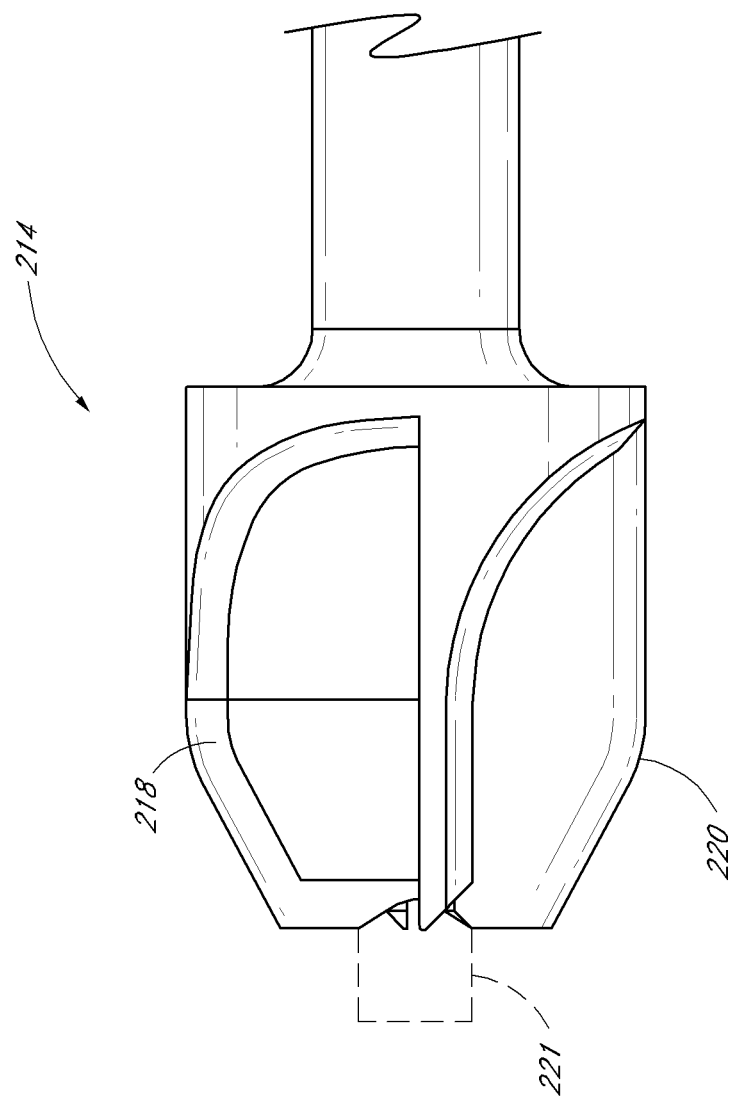
FIG. 9B is an enlarged side view of the distal end of the device shown in FIG. 9A.

FIGS. 9A and 9B illustrate an exemplary embodiment of a device 210 that can be used to form the countersink 200 and/or the recess 206 described above. As shown, the device comprises a body 212 having a distal end 214, a proximal end 216 and a guidewire lumen (not shown) extending therethrough. The proximal end 216 is configured to engage any of a variety of standard driving tools as is known in the art. The distal end 214 is provided with an outer surface 220 that generally corresponds to the outer surface 49 of the proximal anchor 50. The outer surface 220 is also provided with one or more removal or cutting features 218 (e.g., flutes, sharp edges, etc.) so as to remove or cut bone as the device 210 is rotated. A pin 221 (shown in dashed lines in FIG. 9B) can be provided at the end of the device 210. The pin 221 can be inserted into the hole formed in the vertebrae and helps to center and support the device 221 at it cuts the countersink 200 and/or recess 206 into the bone.

In use, the device 210 is advanced over a guidewire that is inserted into the inferior vertebrae 10b. As the device 210 is advanced and rotated, the device 210 encounters the inferior process IAP (see FIG. 8) of the superior vertebrae 10b and portions thereof are removed. Further advancement of the device 210, forms the countersink 200 in the superior articular process of the inferior vertebrae 10a and removes additional portions of the superior vertebrae 10b. Accordingly, in this embodiment, the device 210 can be used to form both the countersink 200 and to change the shape of the inferior articular process IAP of the superior vertebrae 10b.

Figure 9C:
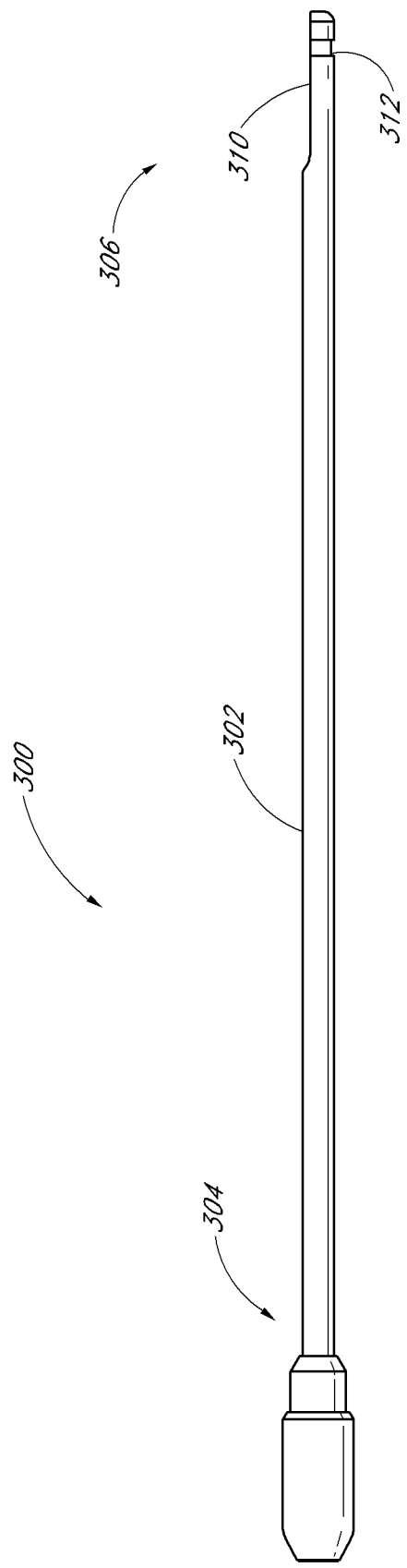
FIG. 9C is a side view of a tool configured to insert a body of a stabilization device, according to an embodiment.
Figure 9D:
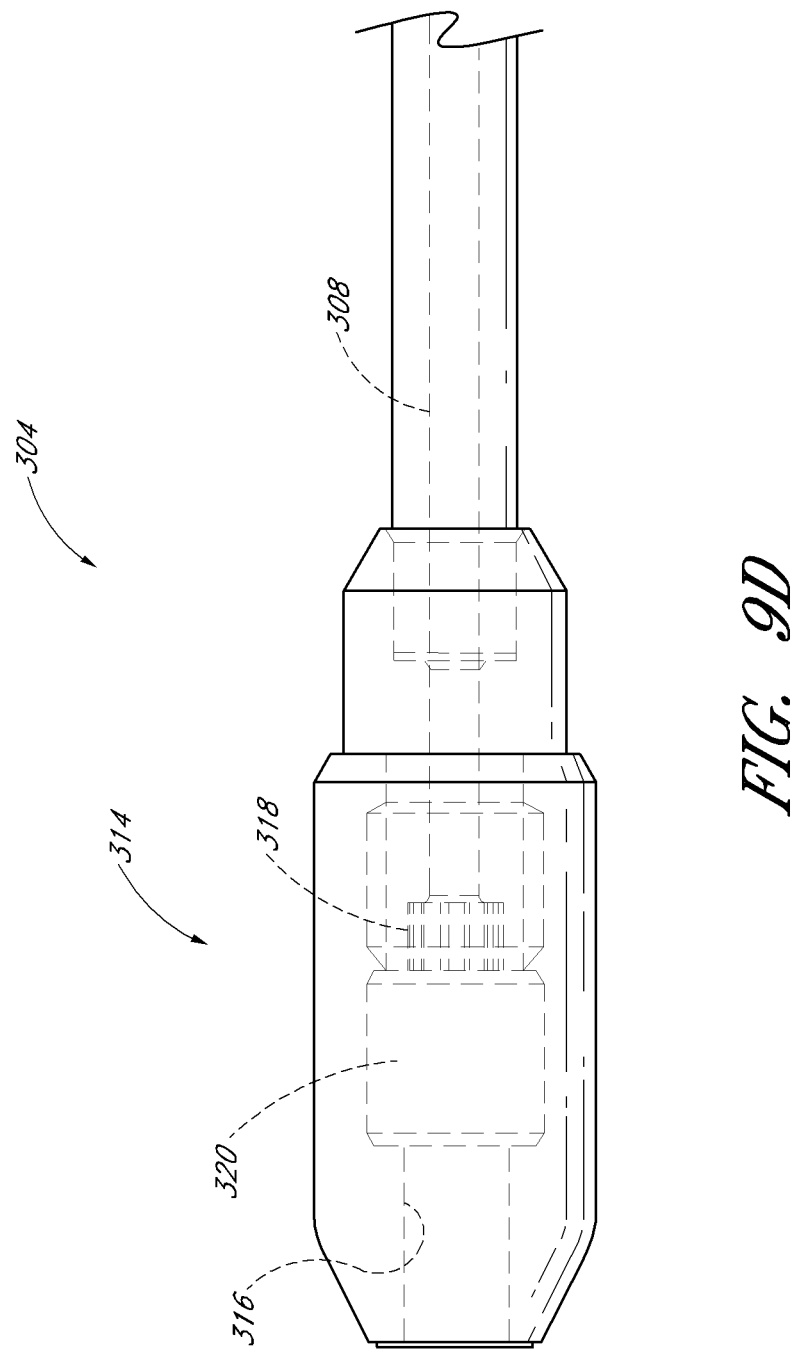
FIG. 9D is an enlarged side view of the tool shown in FIG. 9C.
Figure 9E:
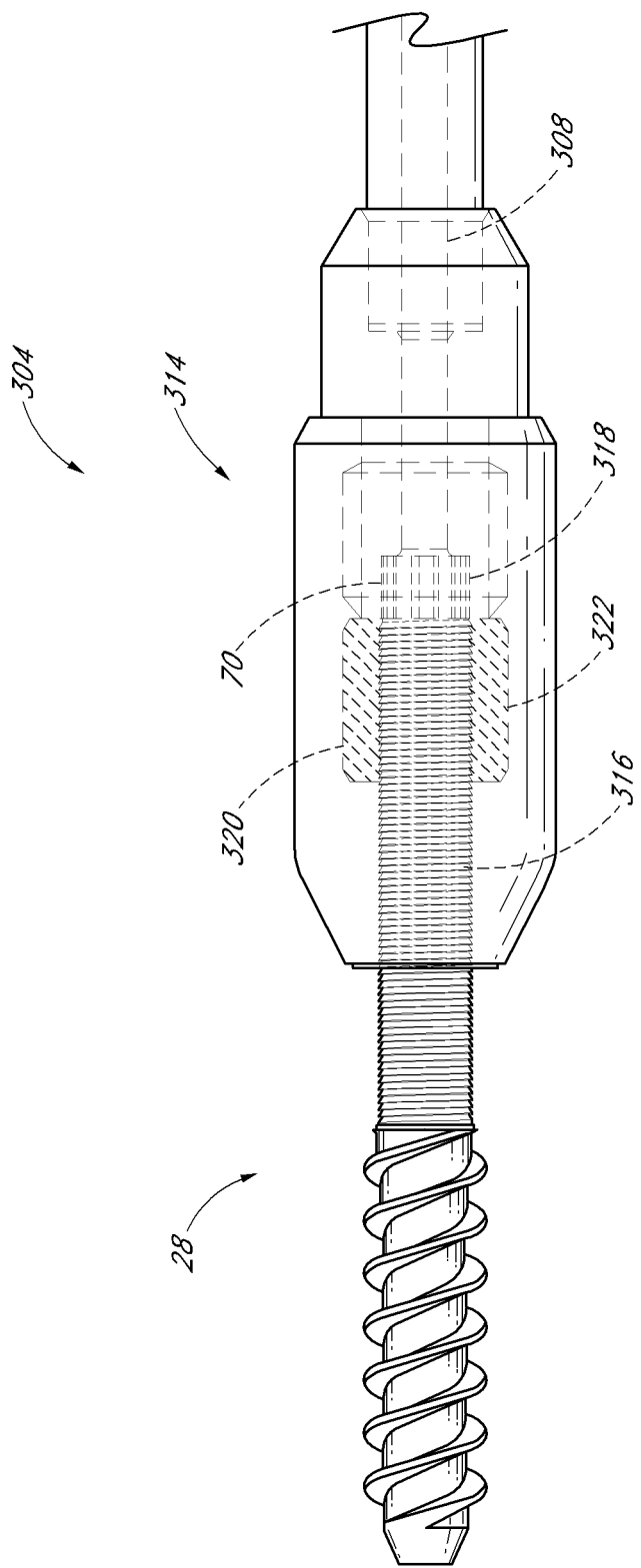
FIG. 9E is an enlarged side view of the tool shown in FIG. 9C with a body of a stabilization device inserted therein.

FIGS. 9C-E illustrate an insertion tool 300 that may be used to rotate and insert the body 28 as described above. As shown, the tool 300 generally comprises an elongated shaft 302 having a distal end 304, a proximal end 306 and a guidewire lumen 308 extending there through. In the illustrated embodiment, the proximal end 304 includes a flat edge 310 and engagement feature 312 for engaging a driving tool (e.g., a drill). In modified embodiments, the proximal end 306 can include a handle such that the tool 300 can be rotated manually.

The distal end 304 of the tool 306 is provided with a distal sleeve portion 314, which has an outer shape that preferably corresponds substantially to the outer surface shape of the proximal anchor used in the procedure. Within the distal sleeve portion 314 is a lumen 316, which communicates with the guidewire lumen 308 and is configured to receive the proximal end of the body 28. The lumen 316 includes a rotational region 318 configured to engage the coupling 70 on the proximal end of the body 28. Distal to the rotational region 318 is a recess 320 in which an elastic or resilient member 322 (e.g., a silicon sleeve) can be placed. As shown in FIG. 9E, when the proximal end of the body 28 is inserted into the lumen 316, the rotational region 318 engages the coupling 70 and the elastic or reslilent member 322 grips the body 28 to hold the body 28 in place within the tool 300.

As described above, the insertion tool 300 may be used to rotate the body 28 thereby driving the distal anchor 34 to the desired depth within the pedicle of the vertebrae. The surgeon can stop rotating the body 28 before the distal end of the tool 300 contacts the bone. In embodiments, in which a countersink is formed, the tool 300 can be rotated until the distal end sits within the countersink at which point further rotation of the tool 300 will not cause the distal anchor to advance further as further advancement of the body 28 causes it to be released from the tool 300. In this manner, over advancement of the distal anchor 32 into the vertebrae can be prevented or limited.

It should be appreciated that not all of the steps described above are critical to procedure. Accordingly, some of the described steps may be omitted or performed in an order different from that disclosed. Further, additional steps may be contemplated by those skilled in the art in view of the disclosure herein, without departing from the scope of the present inventions.

With reference to FIGS. 1A and 1B, the proximal anchors 50 of the devices 12 extend above the pars such that they abut against the inferior facet of the superior adjacent vertebrae. In this manner, the proximal anchor 50 forms a wedge between the vertebra limiting compression and/or extension of the spine as the facet of the superior adjacent vertebrae abuts against the proximal anchor 50. In this manner, extension is limited while other motion is not. For example, flexion, lateral movement and/or torsion between the superior and inferior vertebra is not limited or constrained at least to the degree of the extension. In this manner, the natural motion of the spine can be preserved, especially for those patients with mild or moderate disc conditions. Preferably, the devices are implantable through a minimally invasive procedure and, more preferably, through the use of small percutaneous openings as described above. In this manner, the high cost, lengthy inpatient hospital stays and the pain associated with open procedures can be avoided and/or reduced. In one embodiment, the devices 12 may be removed and/or proximal anchors 50 may be removed in a subsequent procedure if the patient's condition improves. Once implanted, it should be appreciated that, depending upon the clinical situation, the proximal anchor 50 may be positioned such that it contacts surfaces of the adjacent vertebrae all of the time, most of the time or only when movement between the adjacent vertebrae exceeds a limit.

In some instances, the practitioner may decide to use a more aggressive spinal fixation or fusion procedure after an initial period of using the stabilization device 12. In one particular embodiment, the bone stabilization device 12 or a portion thereof may be used as part of the spinal fixation or fusion procedure. In one such application, the proximal anchor 50 can be removed from the body 28. The body 28 can remain in the spine and used to support a portion of a spinal fixation device. For example, the body 28 may be used to support a fixation rod that is coupled to a device implanted in a superior or inferior vertebrae. Examples of such fusion systems can be found in U.S. patent application Ser. No. 10/623,193, filed Jul. 18, 2003 (U.S. Patent Publication No. 2004/0127906), the entirety of which is hereby incorporated by reference herein. Such a device is also described below.

As mentioned above, in certain embodiments described above, it may be advantageous to allow the proximal anchor to rotate with respect to the body 28 thereby preventing the proximal anchor 50 from causing the distal anchor 34 from backing out of the pedicle. In another embodiment, engagement features (as described below) may be added to the proximal anchor 50 to prevent rotation of the proximal anchor 50.

Figure 1C:
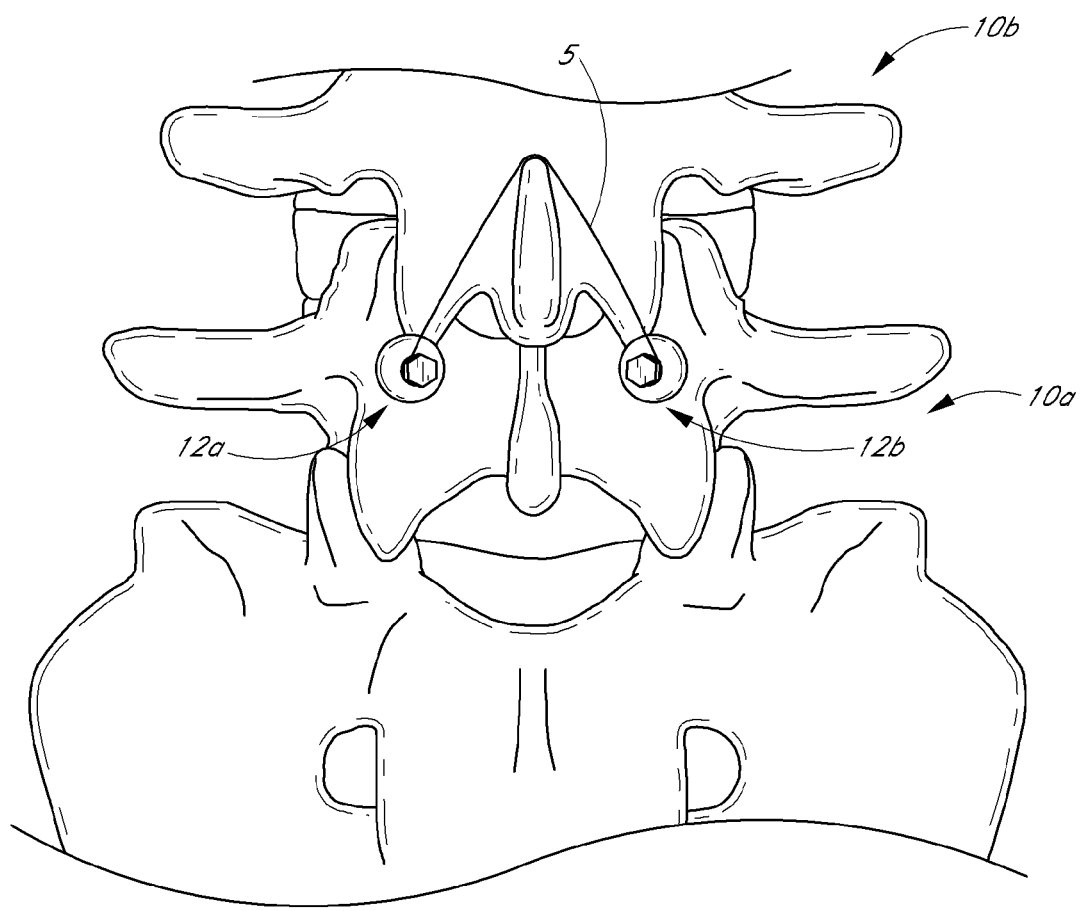
FIG. 1C is a posterior view of a portion of a vertebra having two devices similar to that of FIG. 1A implanted substantially bilaterally therein and a member extending between the two devices, according to yet another embodiment.
Figure 1D:
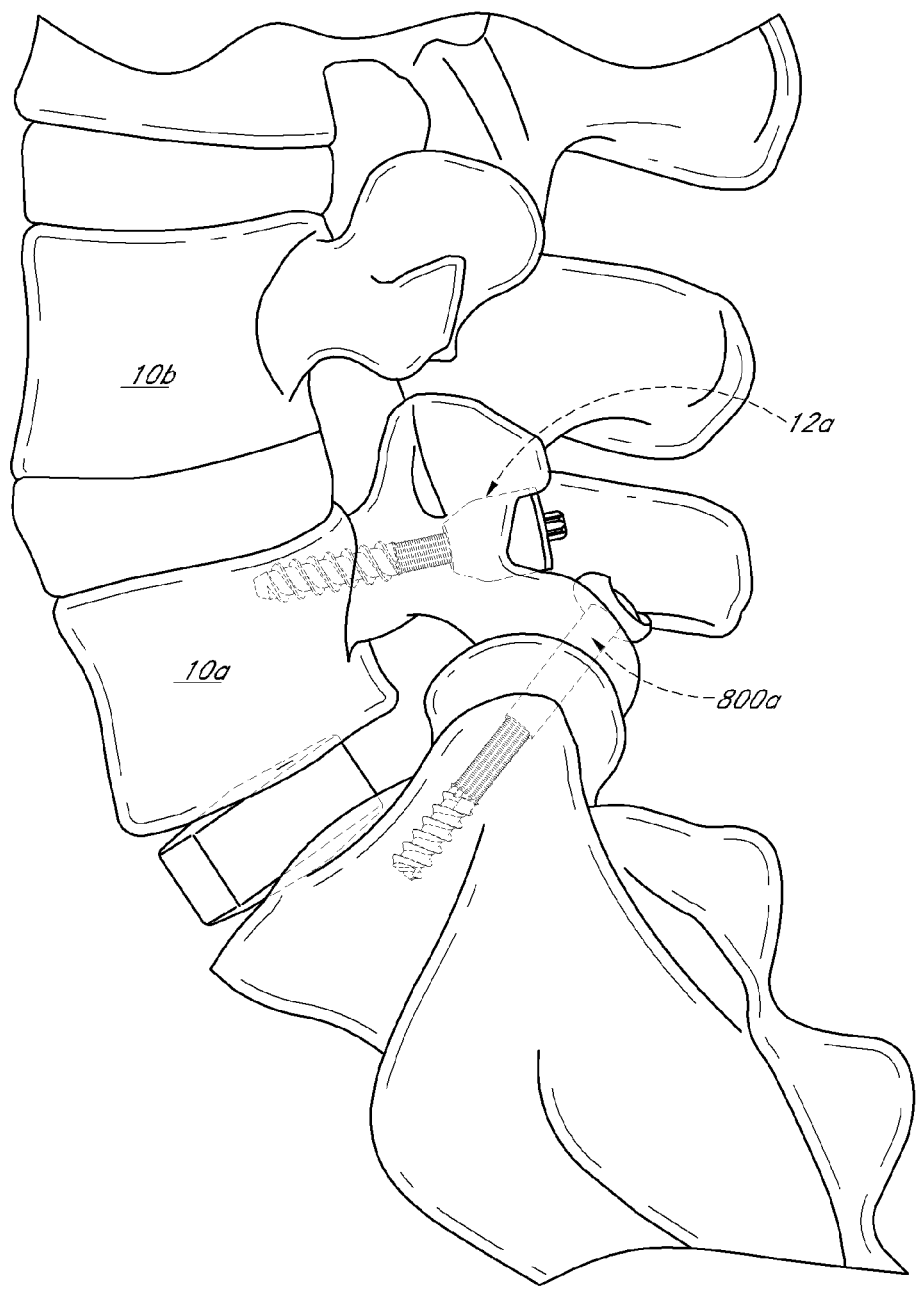
FIG. 1D is a side elevational view of a portion of a vertebra stabilization devices implanted therein, according to another embodiment.
Figure 1E:
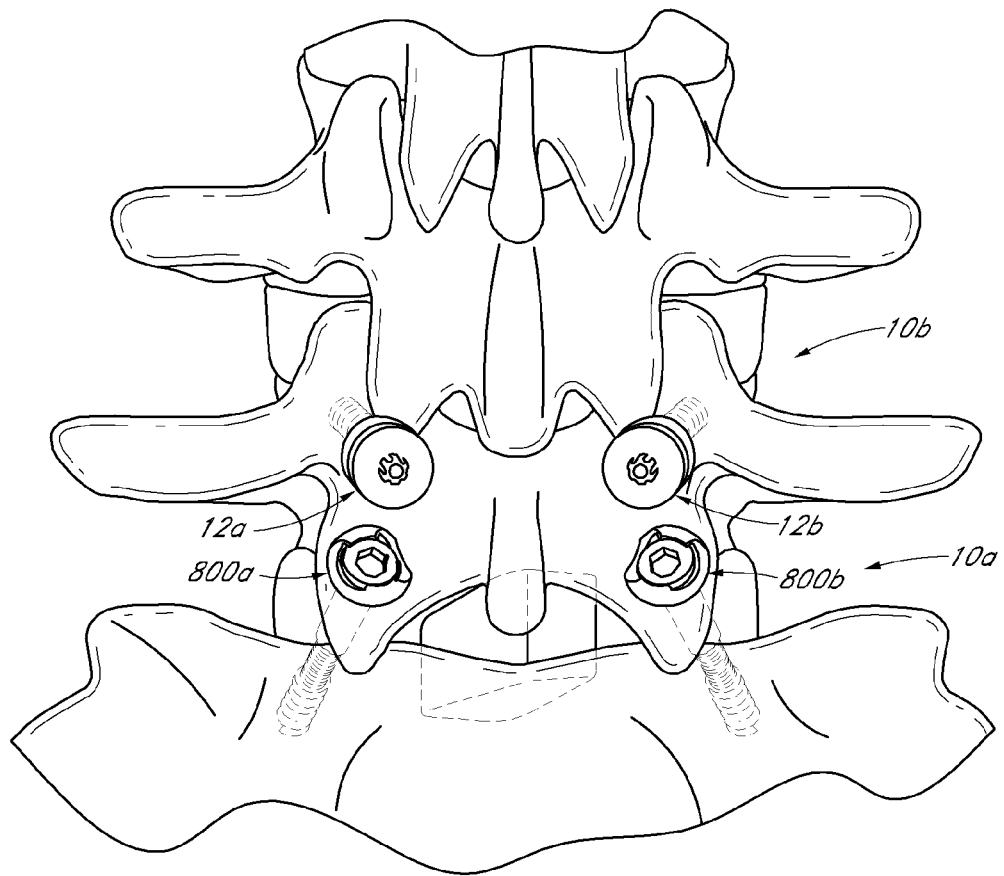
FIG. 1E is a posterior view of a portion of a vertebra having four stabilization devices similar to that of FIG. 1D implanted substantially bilaterally therein, according to another embodiment.

FIG. 1C illustrates a modified embodiment in which the first and second fixation devices 12a, 12b are coupled together by a member 5 that extends generally around or above the spinous process of the superior vertebra 10b. In this manner, the member 5 can be used to limit flexion of the spinal column. The member may comprise any of a variety of suitable structural members. In one embodiment, the member comprises a suture or wire that is tied to the proximal end of the bodies 28 or the proximal anchor. In certain embodiments, various hooks or eyelets can be provided on the body or proximal anchor to facilitate coupling the member to the devices 12a, 12b.

The fixation devices 12 described herein may be made from conventional non-absorbable, biocompatible materials including stainless steel, titanium, alloys thereof, polymers, composites and the like and equivalents thereof. In one embodiment, the distal anchor comprises a metal helix, while the body and the proximal anchor comprise a bioabsorbable material. Alternatively, the distal anchor comprises a bioabsorbable material, and the body and proximal anchor comprise either a bioabsorbable material or a non-absorbable material.

In one embodiment, the proximal anchor 50 is formed, at least in part, from an elastic and/or resilient material. In this manner, the shock and forces that are generated as the proximal anchor abuts or wedges against the inferior articular process of the superior adjacent vertebrae can be reduced or dissipated. In one such embodiment, the proximal anchor 50 is formed in part by a polycarbonate urethane or a hydrogel. In such embodiments, the elastic material may be positioned on the outer surfaces of the proximal anchor or the portions of the outer surfaces that abut against the surfaces of the inferior articular process of the superior adjacent vertebrae. In one embodiment, such an anchor has a modulus of elasticity that is lower than that of metal (e.g., titanium). In another embodiment, the modulus of elasticity can be substantially close to that of bone. In yet another embodiment, the modulus of elasticity can be less than that of bone. In this manner, the stress risers generated during cyclic loading can be reduced to thereby reduce the tendency of the inferior articular process and the inferior vertebrae to crack during cyclic loading.

Figure 10A:
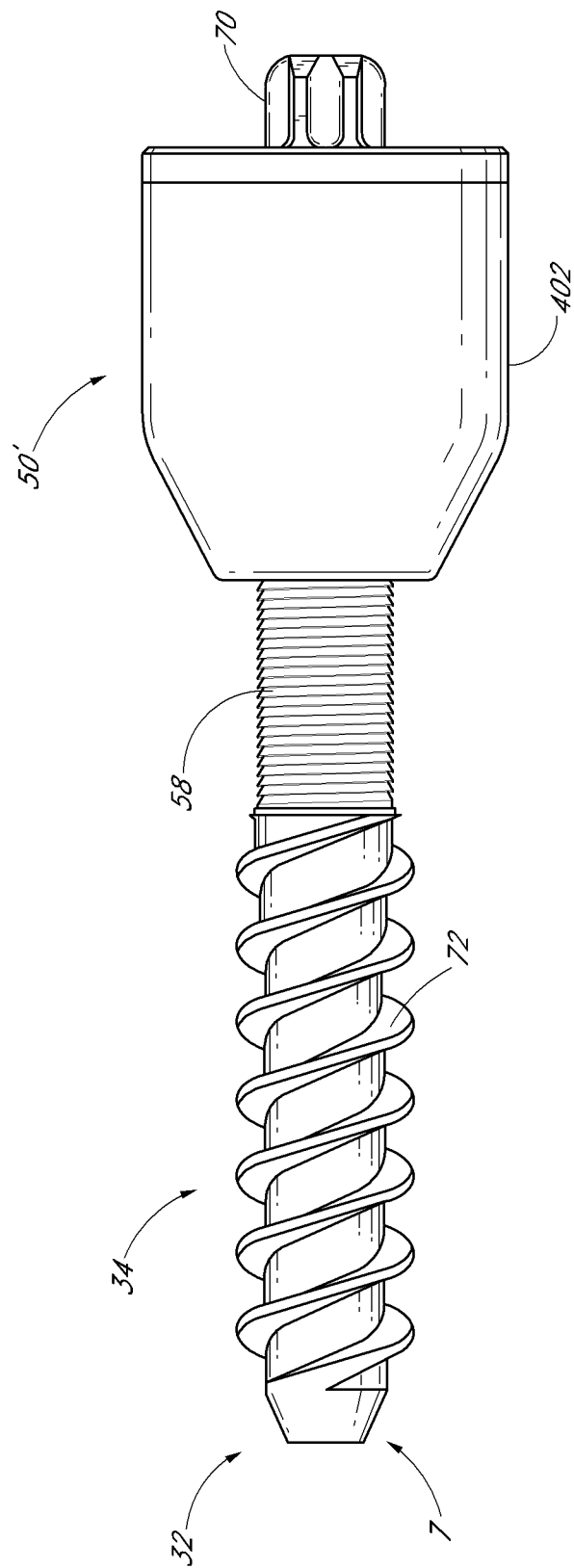
FIG. 10A is a side view of yet another embodiment of a stabilization device.
Figure 10B:
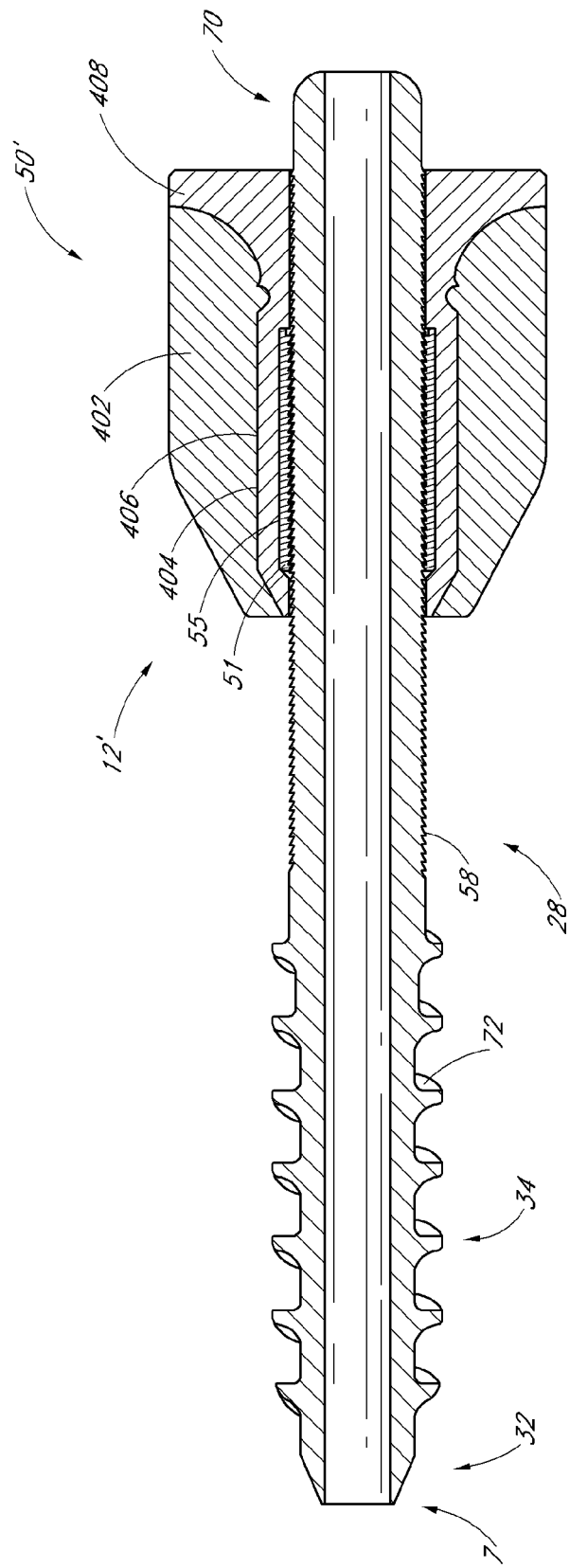
FIG. 10B is a cross-sectional side view of the stabilization device shown in FIG. 10A.
Figure 11B:
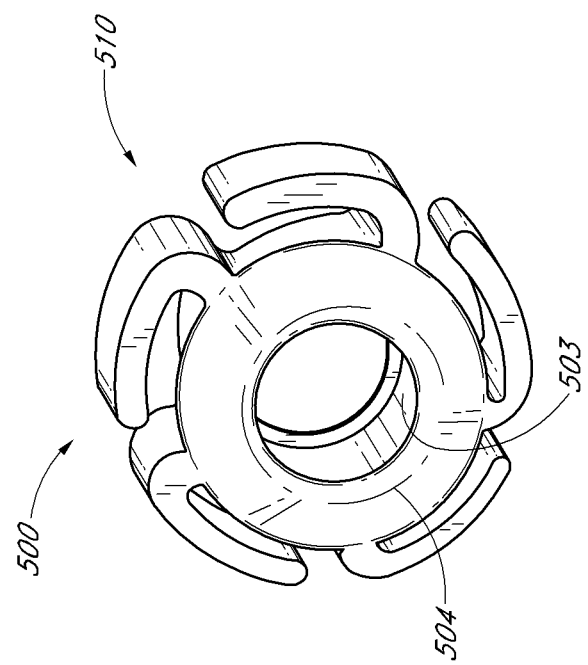
FIGS. 11A and 11B are perspective rear and front views of another embodiment of a proximal anchor.
Figure 11A:
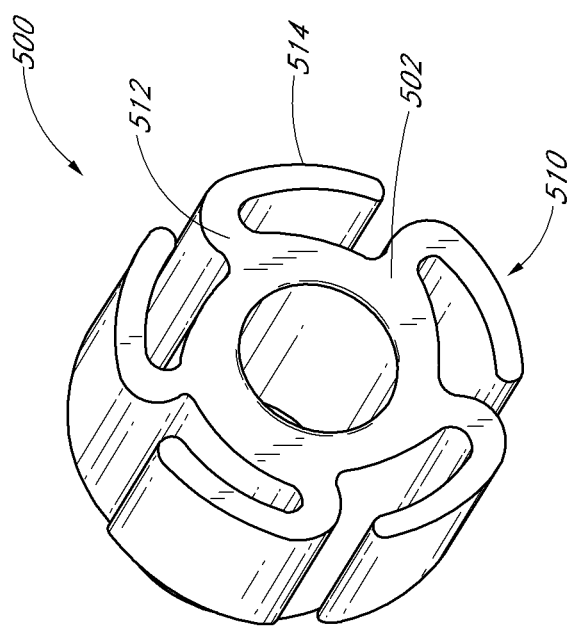
Figure 12B:
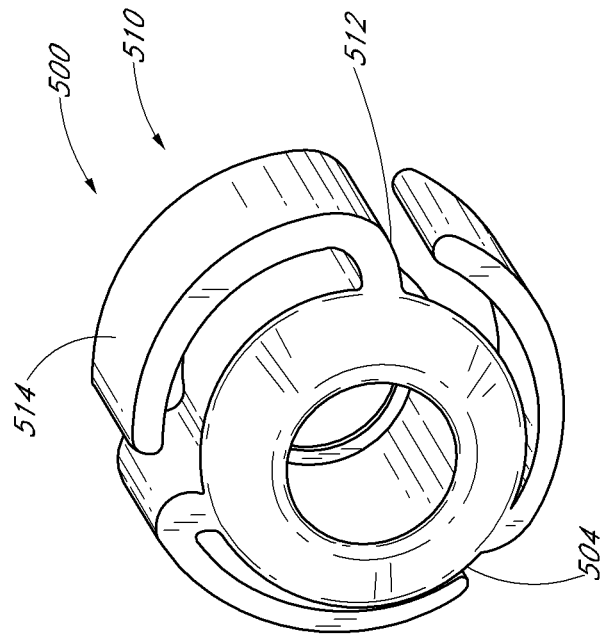
FIGS. 12A and 12B are perspective rear and front views of another embodiment of a proximal anchor.
Figure 12A:
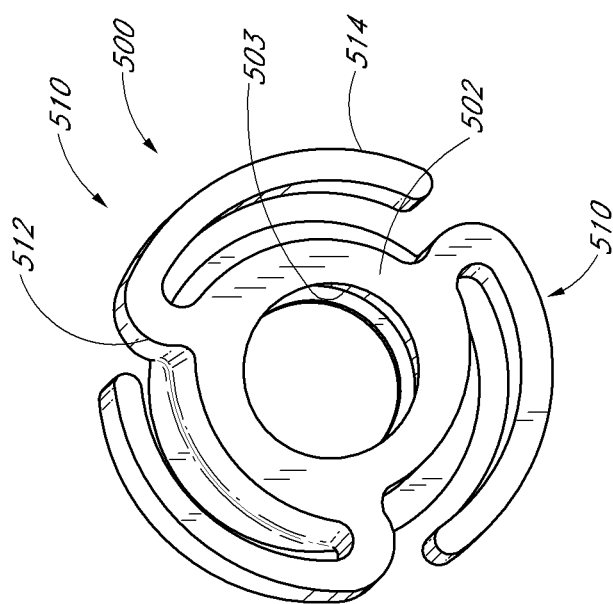
Figure 13B:
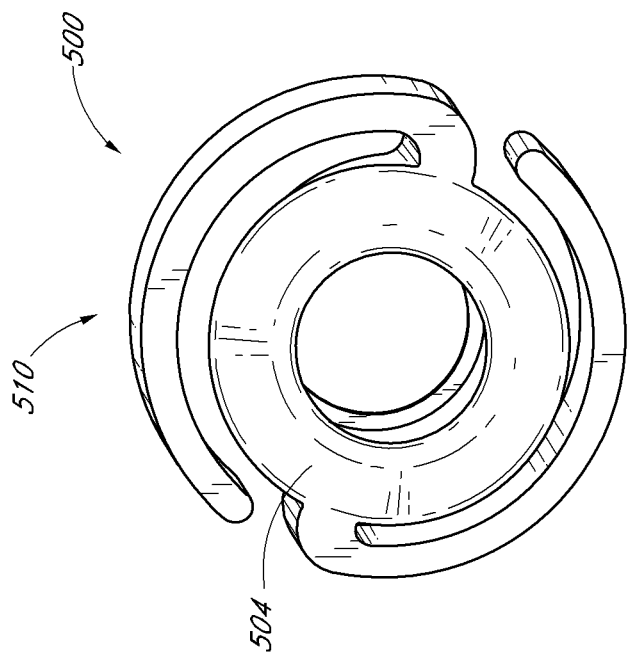
FIGS. 13A and 13B are perspective rear and front views of another embodiment of a proximal anchor.
Figure 13A:
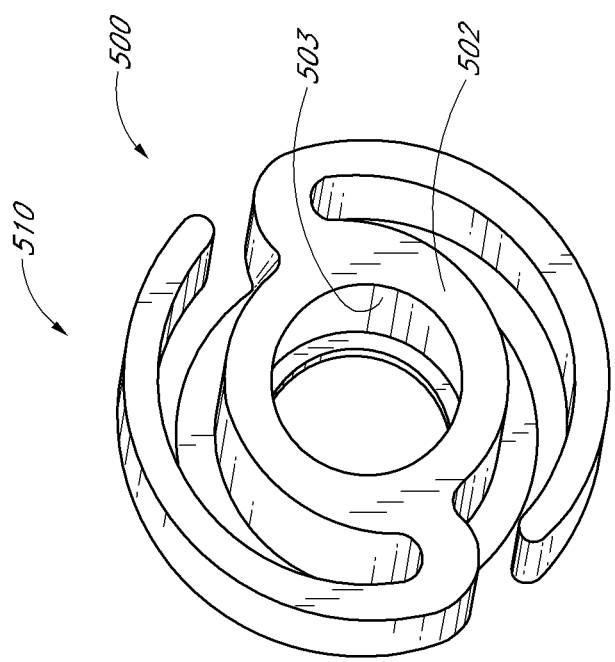

For example, FIGS. 10A and 10B illustrate an embodiment of device 12' with a proximal anchor 50' that comprises an outer housing or shell 402. The shell 402 may be formed or a resilient material such as, for example, a biocompatible polymer. The proximal anchor 50' also comprises an inner member 404 that comprises a tubular housing 406 and a proximal flange 408. The inner member 402 is preferably formed of a harder more rugged material as compared to the shell 402, such as, for example, titanium or another metallic material. The shell 402 is fitted or formed over the tubular housing 406. When deployed, the shell 402 is held in place between the flange 408 and the surface of the vertebrae in which the body 402 is placed. In modified embodiments, the shell 402 may be coupled to the inner member 404 in a variety of other manners, such as, adhesives, fasteners, interlocking surfaces structures and the like. In the illustrated embodiment, the inner member 404 includes a locking ring 51 positioned within a recess 55 as described above. Of course, in modified embodiments, other retention structures 54 and complementary retention structures 58 may be used between the body 28 and the proximal anchor 50' to permit distal axial travel of the proximal anchor 50' with respect to the body 28, but resist proximal travel of the proximal anchor 50' with respect to the body 28.

In the illustrated embodiment of FIGS. 10A and 10B, the distal anchor 34 is provided with atraumatic or blunt tip 7. In addition, the flange 72 of the distal anchor 34 includes a square or blunt edges. These features reduce the tendency of the distal anchor to cut into the bone during the windshield-wiper effect that may be caused by cyclic loading of the device as described above.

In another embodiment, the proximal anchor 50 is provided with a mechanically resilient structure. Thus, as with the previous embodiment, the shock and forces that are generated as the proximal anchor abuts or wedges against the inferior articular process of the superior adjacent vertebrae can be reduced or dissipated. In one such embodiment, the proximal anchor 50 is provided with mechanical springs, lever arms and/or the like. In such embodiments, as the mechanically resilient structure is compressed or extended the shock and forces are reduced or dissipated.

For example, FIGS. 11A-13B illustrate embodiments of a proximal anchor 500, which comprises a tubular housing 502, which includes a recess 503 for receiving a locking ring 51 as described above. The distal end 504 of the housing 502 forms a generally rounded, semi-spherical face that can be inserted into a corresponding counter sink 200 (see FIG. 8) as describe above. Extending from the housings 502 are a plurality of lever arms or deflectable flanges 510. Each arm 510 generally comprises a generally radially extending portion 512 and a generally circumferential extending portion 514. In the illustrated embodiments, two (FIGS. 13A-B), three (FIGS. 12A-B) and five arms (FIGS. 11A-B) are shown. However, the anchor 500 can include different numbers of arms (e.g., one, four or greater than five arms). As the superior adjacent vertebrae 10b moves against the proximal anchor 500 the radially extending portion 514 deflects relative to the tubular housing 502 to absorb or disperse the forces generated by the contact.

As mentioned above, in the illustrated embodiment, the tubular member 502 includes a locking ring 51 positioned within a recess 503 as described above. Of course, in modified embodiments, other retention structures and complementary retention structures may be used between the body 28 and the proximal anchor 500 to permit distal axial travel of the proximal anchor 500 with respect to the body 28, but resist proximal travel of the proximal anchor 500 with respect to the body 28.

Figure 14:
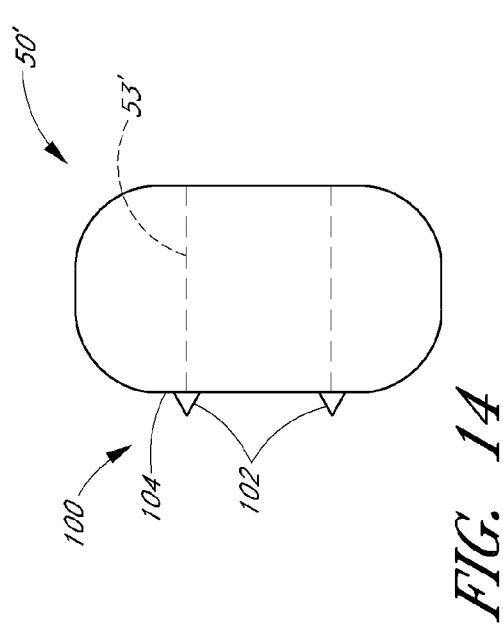
FIG. 14 is a side view of yet another embodiment of a proximal anchor.

With reference to FIG. 14, in a modified embodiment, a distal end of a proximal anchor 50' may include one or more bone engagement features 100, which in the illustrated embodiment comprises a one or more spikes 102 positioned on a contacting surface 104 of the proximal anchors. The spikes 102 provide additional gripping support especially when the proximal anchor 50' is positioned against, for example, uneven bone surfaces and/or soft tissue. In addition, the spikes 102 may limit rotation of the proximal anchor 50' with respect to the body 28 thereby preventing the proximal anchor 50' from backing off the body 28. Other structures for the bone engagement feature 100 may also be used, such as, for example, ridges, serrations, etc.

Figure 16:
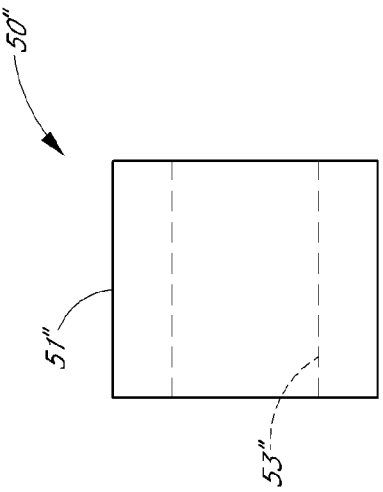
FIG. 16 is a side view of yet another embodiment of a proximal anchor.
Figure 15:
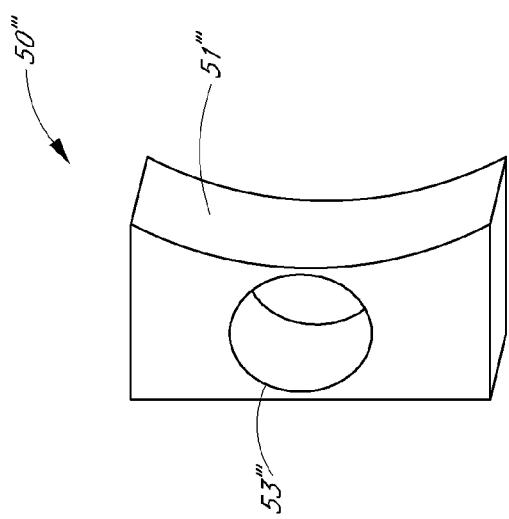
FIG. 15 is a side perspective view of yet another embodiment of a proximal anchor.

FIGS. 15 and 16 illustrate modified shapes of the proximal anchor which can be used alone or in combination with the elastic or resilient material described above. In FIG. 15, a proximal anchor 50" has a saddle shaped curved surface 51" that generally faces the inferior articular process of the superior adjacent vertebra. In this embodiment, the saddle shaped surface may limit compression and/or extension of the adjacent vertebra and limit side to side motion and/or torsion between the vertebrae. FIG. 16 illustrates an embodiment in which a proximal anchor 50''' has a rectangular shape with a flat shaped surface 51'''. In this embodiment, the flat shaped surface may limit compression and/or extension of the adjacent vertebra and limit side to side motion between the vertebrae. In the embodiments of FIGS. 15 and 16, it may be advantageous to limit or eliminate any rotation of the proximal anchor 50" and 50''' with respect to the body 28 and/or the vertebra. As such, the proximal anchor 50" and 50''' can include the retention devices 100 described above with reference to FIG. 14.

As mentioned above, in certain embodiments, clinician will also have an array of proximal anchors 50', 50", and 50''', having, for example, different configurations and/or shapes. The clinician will choose the appropriate body 28 and then assess the position of the body 28 with respect to the superior vertebrae and chose a proximal anchor from the array, which best fits the patient anatomy to achieve the desired clinical result. In such an embodiment, the proximal anchor can be advantageously coupled to body 28 after the body 28 is partially or fully inserted into the vertebrae. The clinician may also be provided with an array of devices for forming differently sized or shaped countersinks corresponding to the different proximal anchors.

As described above, in one embodiment, the proximal anchor 50 (which can also refer to any or all of 50', 50", or 50''') is configured such that it can be removed after being coupled and advance over the body 28. In this manner, if the clinician determines after advancing the proximal anchor that the proximal anchor 50 is not of the right or most appropriate configuration (e.g., size and/or shape), the clinician can remove the proximal anchor 50 and advance a different proximal anchor 50 over the body 28. In such an embodiment, the proximal anchor 50 is preferably provided with one or more engagement structures (e.g., slots, hexes, recesses, protrusions, etc.) configured to engage a rotational and/or gripping device (e.g., slots, hexes, recesses, protrusions, etc.). Thus, in some embodiments, the proximal anchor 50 can be pulled and/or rotated such that the anchor 50 is removed from the body 28.

Figure 17:
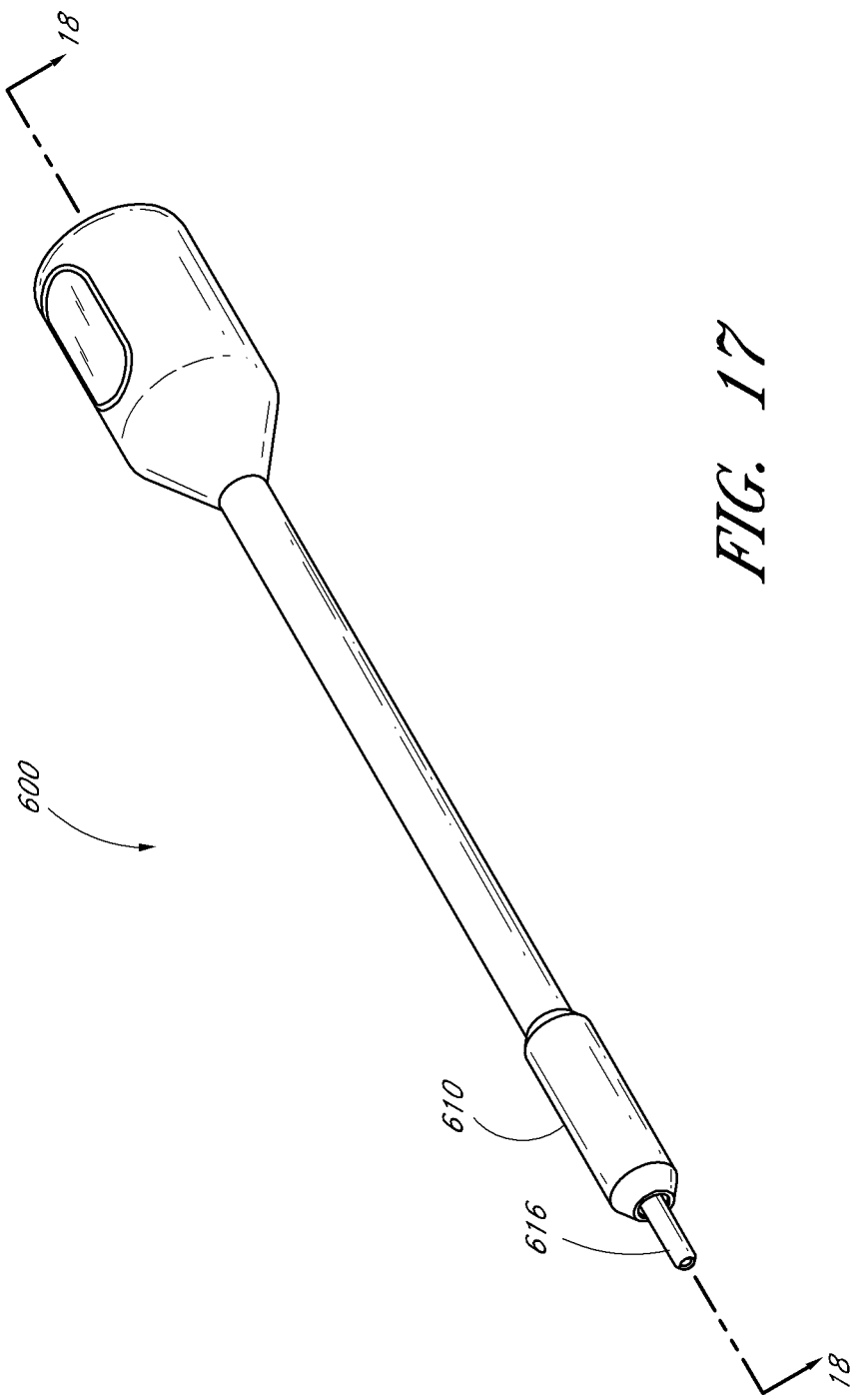
FIG. 17 is a side perspective view of an embodiment of an insertion tool configured to insert a proximal onto a body portion of a fixation device.
Figure 18:
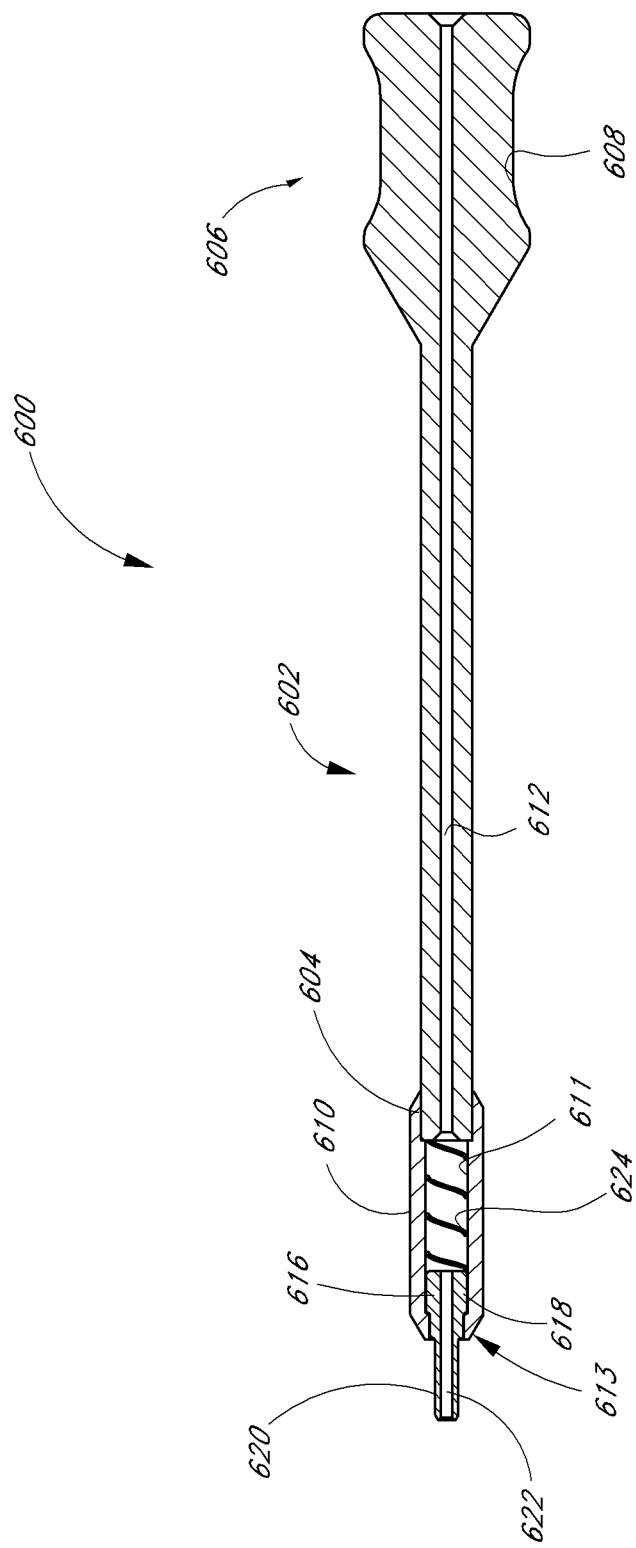
FIG. 18 is a cross-sectional side view of the insertion tool shown in FIG. 17.

FIGS. 17 and 18 illustrate an embodiment of a tool 600 that can be used to insert a proximal anchor 50 that utilizes a locking ring 51 (as described above) onto a body 28 of the device 12. In the illustrated embodiment, the tool 600 comprises an elongated body 602 having a distal end 604 and a proximal end 606. The proximal end 606 is provided with a handle 608 for manipulating the tool 600. The distal end 604 of the device is generally tubular and is coupled to or otherwise attached to a distal sleeve 610. The distal sleeve defines a chamber 611, which extends from the distal end 604 of the elongated body 602 to the distal end 613 of the sleeve 610. A guidewire lumen 612 can extend through the tool 600.

With particular reference to FIG. 18, a pin 616 is partially positioned within the chamber 611. The pin 616 includes an enlarged proximal portion 618, which is positioned in the chamber 611. The pin 616 also includes a reduced diameter portion 620, which extends outside the chamber 611. A guidewire lumen 622 can also extend through the pin 616 such that the entire tool 600 can be inserted over a guidewire. A biasing member 624 is positioned between the distal end 604 of the tubular member 602 the proximal end 618 of the pin 616. In this manner, the pin 616 is biased to the position shown in FIG. 18. Advantageously, the distal end 620 of the pin 616 has an outside diameter that is slightly larger than the inner diameter of the locking ring 51 (see e.g., FIG. 10B). Accordingly, the distal end 620 of the pin 616 can be inserted into the proximal anchor through its proximal end. In one embodiment, the locking ring 51 grasps the distal end 620 of the pin 616 to couple the proximal anchor 50 to the pin 616. In the loaded position, the proximal end of the proximal anchor 50 preferably contacts the distal end 613 of the distal sleeve 610.

In use, the tool 600 is coupled to the proximal anchor as described above. After the body 28 is inserted into the vertebrae, the tool 600 can be used to position the proximal anchor 50 over the proximal end of the body 28. The tool 600 is then advanced forward. As the tool 600 is advanced forward, the proximal anchor 50 is pushed onto the body 28 as the pin 616 retracts into the chamber 611. In this manner, the pin 616 holds the locking ring 51 in an expanded position until it engages the body 28. Once the pin 616 is fully retracted into the chamber 611, the pin 616 is decoupled from the proximal anchor 50 and the proximal anchor 50 is fully coupled to the body 28.

Figure 19:
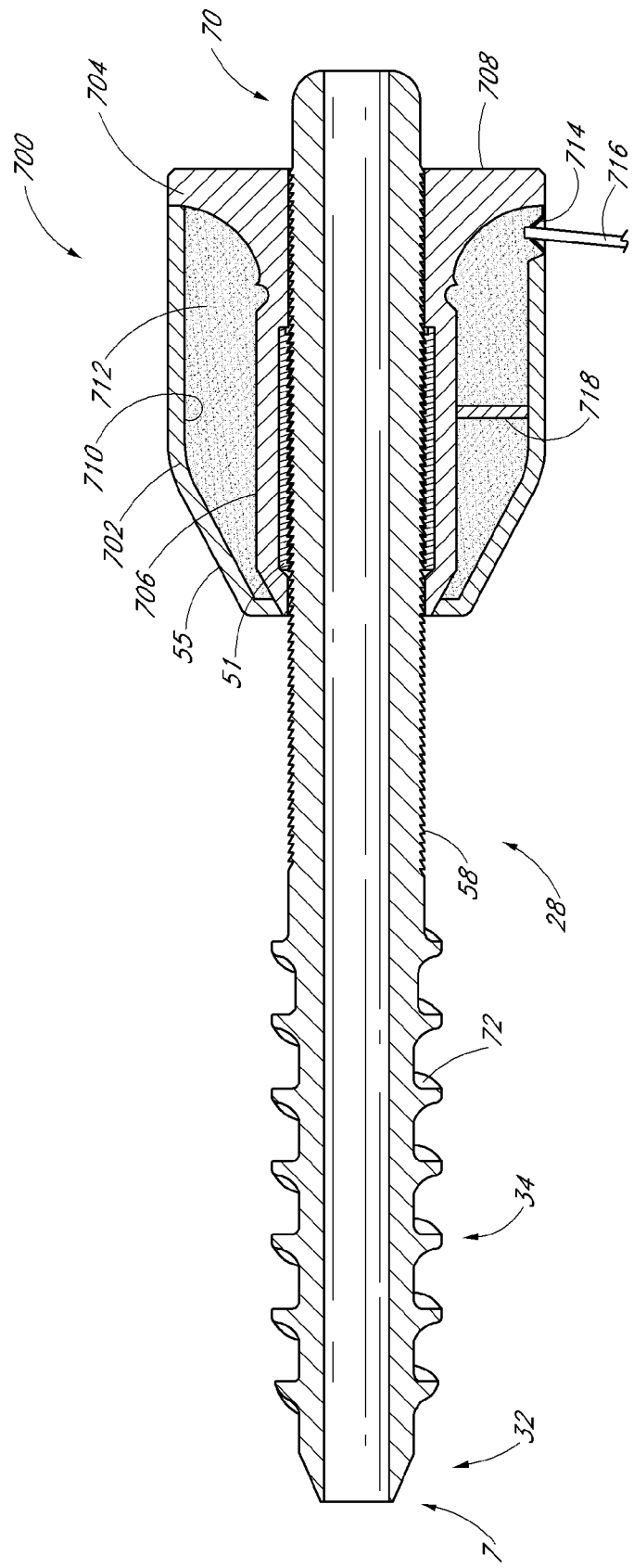
FIG. 19 is a cross-sectional side view of a modified embodiment of a stabilization device.

In another embodiment, a dimension of the proximal anchor is capable of being adjusted. For example, FIG. 19 illustrates an embodiment of a proximal anchor 700 in which the proximal anchor 700 can be radially expanded such that the relationship between the anchor 700 and the adjacent vertebrae can be adjusted by the surgeon. In this embodiment, the anchor 700 comprises a wall 702, which can be formed of an elastic material. The wall is coupled to an inner member 704 that comprises a tubular housing 706 and a proximal flange 708, which can be arranged as described above with reference to FIG. 10B. The wall 702 and the inner member 704 define a cavity 710, which can be filled with an inflation material 712, such as, for example, a gas, liquid, gel, and/or hardenable or semi-hardenable media (e.g., an polymer, epoxy or cement). One or more valves 714 (e.g., a duck bill valve) can be provided along the wall 702. An inflation lumen 716 can extend through the valve such that the cavity 710 can be inflated with the inflation material 712. After inflation, the lumen 716 is removed and the valve 714 seals the cavity 710. One or more dividing walls 718 can be provided with the cavity 710 such that the anchor 50 can be inflated in discrete or semi-discrete sections.

In one embodiment of use, the body 28 and proximal anchor 700 are inserted into position as described herein. The cavity 710 is then inflated to expand the proximal anchor 50 and increases its diameter. In this manner, the surgeon can control the degree to which the proximal anchor 50 limits the motion of the spine. For example, in one embodiment, increasing the diameter of the proximal anchor 50 would increase the distance between the two vertebrae. In some embodiments, the inflation material 712 can also be removed such that the dimensions can be decreased during the same procedure in which the device 12 is inserted into the spine. In still other embodiments, the inflation material 712 can be added or removed in a subsequent, preferably, minimally invasive second procedure such that the degree which the proximal anchor 50 limits the motion of the spine can be adjusted in the second, subsequent procedure. In one embodiment, this is done by inserting a lumen through the valve and adding and/or removing the inflation media 712.

Figure 20C:
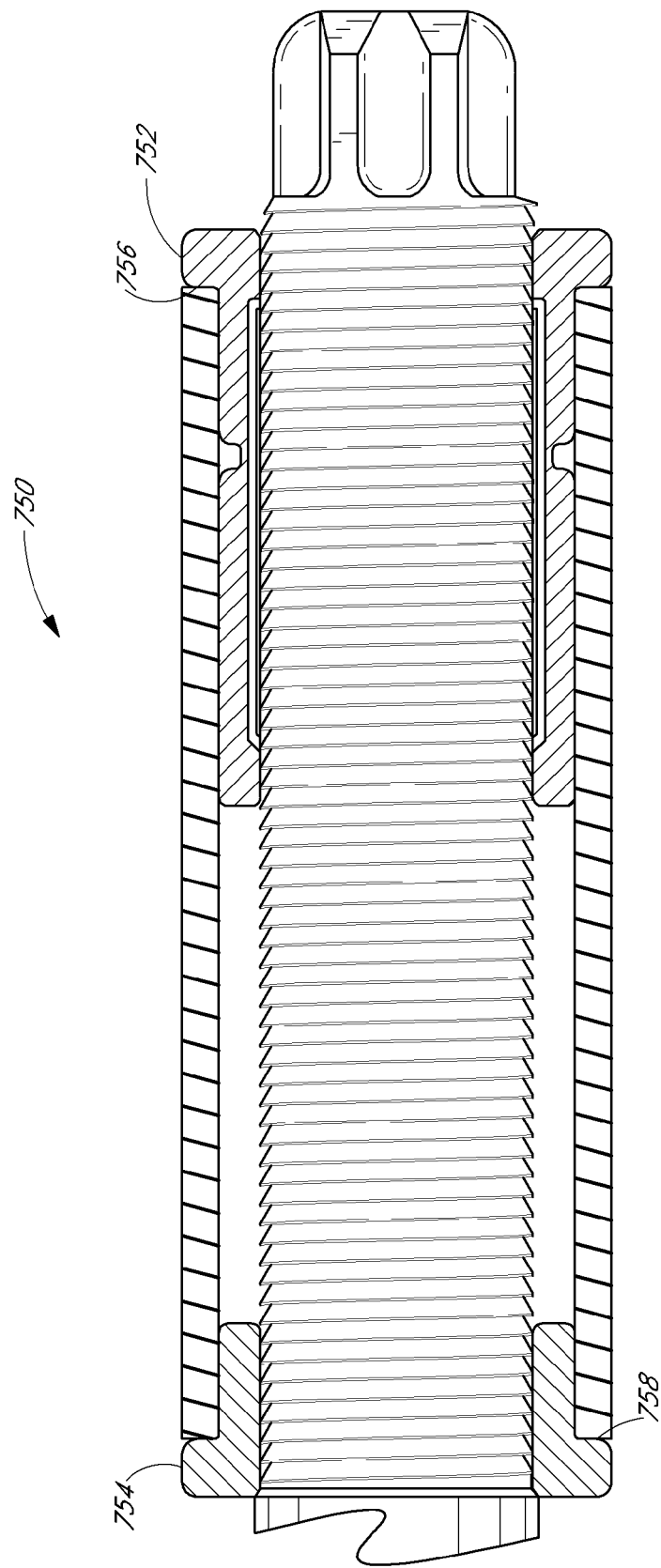
FIG. 20C is a cross-sectional side view of the stabilization device shown in FIG. 20A in an un-expanded configuration.

FIGS. 20A-D illustrates another embodiment of a proximal anchor 750 in which one or more dimensions of the anchor 750 can be adjusted. In this embodiment, the dimensions are adjusted using a mechanical mechanism. With reference to the illustrated embodiments, the anchor 750 can include a proximal member 752 and a distal member 754, which can be moveably carried by the body 28 as described below. The proximal member 752 defines a proximal stop 756 and the distal member 754 defines a distal stop 758. An expandable member 760 is positioned between the proximal and distal stops 756, 758. The expandable member 760 is configured to expand radially as the proximal and distal stops 756, 758 are moved towards each other and the expandable member 760 is compressed therebetween. In one embodiment, the expandable member 760 comprises an elastic material that when compressed expands as shown in FIGS. 20A and 20B. In another embodiment, the expandable member 760 comprises a malleable material (e.g., a metal or metal alloy) that is provided with one or more slots. In such an embodiment, the slots allow the member 760 to expand as it is compressed between the proximal and distal stops 756, 758.

Figure 20D:
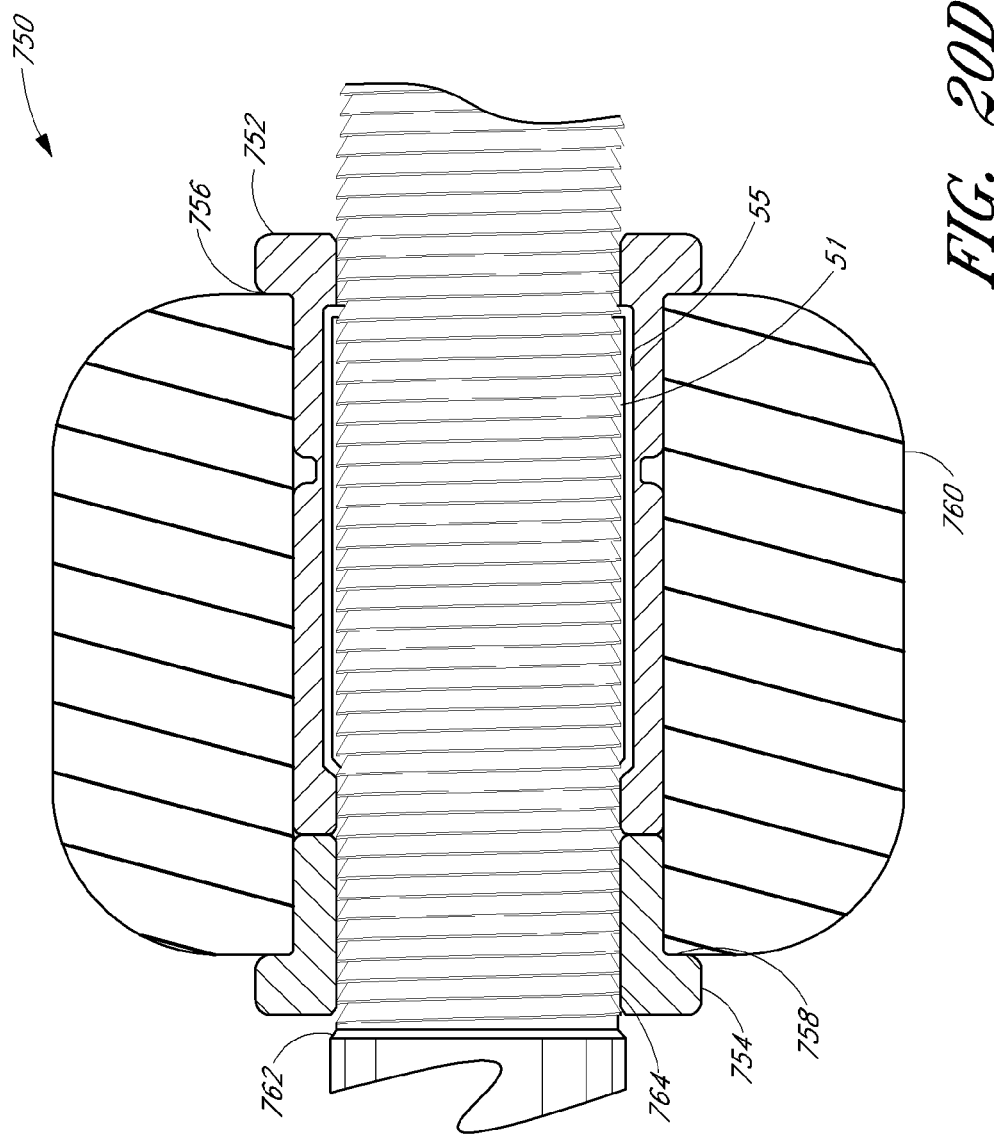
FIG. 20D is an enlarged cross-sectional side view of the stabilization device shown in FIG. 20B in an expanded configuration.

With reference to FIG. 20D, the proximal member 752 can be provided with a recess 55 and ring 51 as described above with reference to FIGS. 5 and 6. In this manner, the proximal member 752 can be advanced in the distal direction while proximal movement of the member 752 is resisted. Of course, other complementary retention structures can be used between the member 752 and the body 28 as described to permit distal movement while resisting proximal movement. The distal movement of the distal member 754 can be prevented by a distal stop 762 provided on the body 28. As shown in FIG. 20D, the distal member 754 can be provided with a smooth bore 764 such that it can be advanced over the body 28 towards the distal stop 762.

Figure 21:
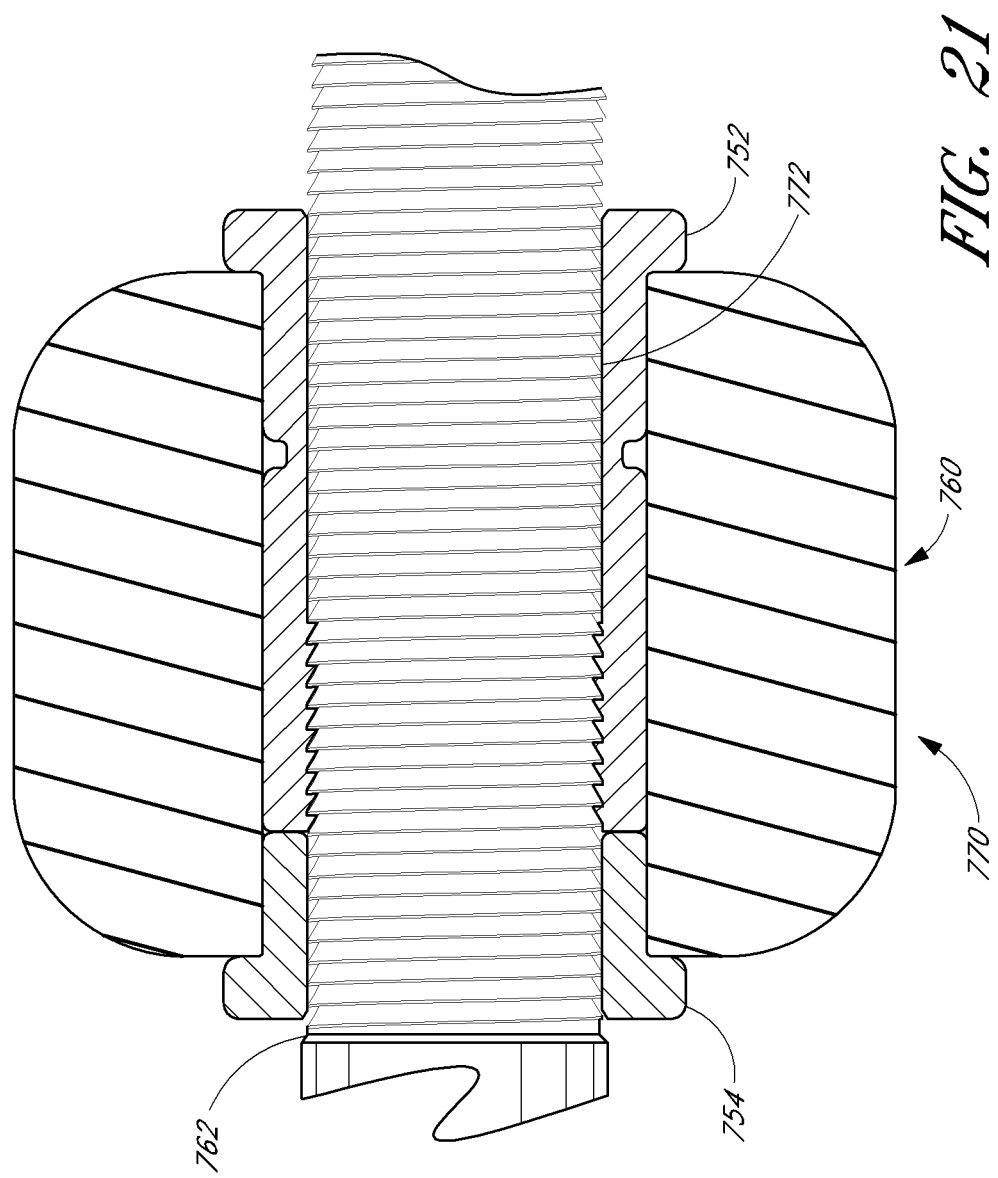
FIG. 21 is a cross-sectional side view of yet another embodiment of a stabilization device in an expanded configuration.

FIG. 21 illustrates an embodiment of a proximal anchor 770 which is similar to the previous embodiment. In this embodiment, the proximal member 752 includes threads 772 such that the proximal member 752 can be distally advanced or proximal retracted by rotation. FIG. 22 illustrates another embodiment of a proximal anchor 780. In this embodiment, the proximal member 752 is configured as described with reference FIG. 20D. However, the distal member 754 is provided with threads 782 such that the position of the distal member 754 on the body 28 can be adjusted.

The above described devices and techniques limit motion of the spine by providing an abutment or wedge surface on one vertebrae or body structure. The abutment surface contacts, abuts, and/or wedges against a portion of a second, adjacent vertebrae or body structure so as limit to at least one degree of motion/freedom between the two vertebra or body structure while permitting at least one other degree of motion. While the above described devices and techniques are generally preferred, certain features and aspects can be extended to modified embodiments for limiting motion between vertebrae. These modified embodiments will now be described.

In one embodiment, the proximal anchor 50 of the fixation device may be, coupled to, attached or integrally formed with the body 28. In this manner, movement between the proximal anchor 50 and the body 28 is not permitted. Instead, the clinician may chose a fixation device of the proper length and advance the device into the vertebrae until the proximal anchor lies flush with the vertebrae or is otherwise positioned accordingly with respect to the vertebrae. In one particular, embodiment, the proximal anchor that is coupled to, attached or integrally formed with the body 28 is configured to have an outer surface which can rotate, preferably freely, with respect to the body 28. This arrangement advantageously reduces the tendency of the device to rotate and/or move within the inferior vertebrae as the proximal anchor 50 contacts the superior vertebrae.

In another embodiment, the abutment surface may be attached to the vertebrae through the use of an adhesive, fasteners, staples, screws and the like. In still another embodiment, the abutment surface may formed on a distal end of a stabilization device that is inserted through the front side of the vertebrae.

In the embodiments described above, the device 12 is generally inserted into the spine from a posterior position such that a distal end of the device 12 is inserted into the first, inferior vertebrae and a proximal end of the device 12 contacts or wedges against the second, superior vertebrae. However, it is anticipated that certain features and aspects of the embodiments described herein can be applied to a procedure in which the device is inserted from a lateral or anterior site. In such an embodiment, the distal end or side portion of the device may contact or wedge against the second superior vertebrae. Such embodiments provide a contact or wedge surface which is supported by one body structure to limit of the motion of an adjacent body structure.

In the embodiments, described above, it is generally advantageous that the proximal anchor be radiopaque or otherwise configured such that in can be seen with visual aids used during surgery. In this manner, the surgeon can more accurately position the proximal anchor with respect to the superior and inferior vertebra.

Preferably, the clinician will have access to an array of fixation devices 12, having, for example, different diameters, axial lengths and, if applicable, angular relationships. These may be packaged one or more per package in sterile or non-sterile envelopes or peelable pouches, or in dispensing cartridges which may each hold a plurality of devices 12. The clinician will assess the dimensions and load requirements, and select a fixation device from the array, which meets the desired specifications.

The fixation devices may also be made from conventional non-absorbable, biocompatible materials including stainless steel, titanium, alloys thereof, polymers, composites and the like and equivalents thereof. In one embodiment, the distal anchor comprises a metal helix, while the body and the proximal anchor comprise a bioabsorbable material. In another embodiment, the body is made of PEEK™ polymer or similar plastic material. Alternatively, the distal anchor comprises a bioabsorbable material, and the body and proximal anchor comprise either a bioabsorbable material or a non-absorbable material. As a further alternative, each of the distal anchor and the body comprise a non-absorbable material, connected by an absorbable link. This may be accomplished by providing a concentric fit between the distal anchor and the body, with a transverse absorbable pin extending therethrough. This embodiment will enable removal of the body following dissipation of the pin, while leaving the distal anchor within the bone.

The components of embodiments of the present inventions may be sterilized by any of the well known sterilization techniques, depending on the type of material. Suitable sterilization techniques include, but not limited to heat sterilization, radiation sterilization, such as cobalt 60 irradiation or electron beams, ethylene oxide sterilization, and the like.

The specific dimensions of any of the embodiments of the bone fixation devices of the present inventions can be readily varied depending upon the intended application, as will be apparent to those of skill in the art in view of the disclosure herein. Moreover, although the present inventions have been described in terms of certain preferred embodiments, other embodiments of the inventions including variations in dimensions, configuration and materials will be apparent to those of skill in the art in view of the disclosure herein. In addition, all features discussed in connection with any one embodiment herein can be readily adapted for use in other embodiments herein. The use of different terms or reference numerals for similar features in different embodiments does not imply differences other than those which may be expressly set forth. Accordingly, the present inventions are intended to be described solely by reference to the appended claims, and not limited to the embodiments disclosed herein.

As mentioned above, the dynamic stabilization device 12 can provide adjacent level support as an adjunct to fusion therapy. In one embodiment, the fusion therapy involves the fixation device 800, which will be described in detail below. The fixation device 800 can be positioned below (or above in other embodiments) the stabilization device 12 and can be used to promote spinal fusion below the spinal level at which motion is limited by the dynamic stabilization device.

Figure 23A:
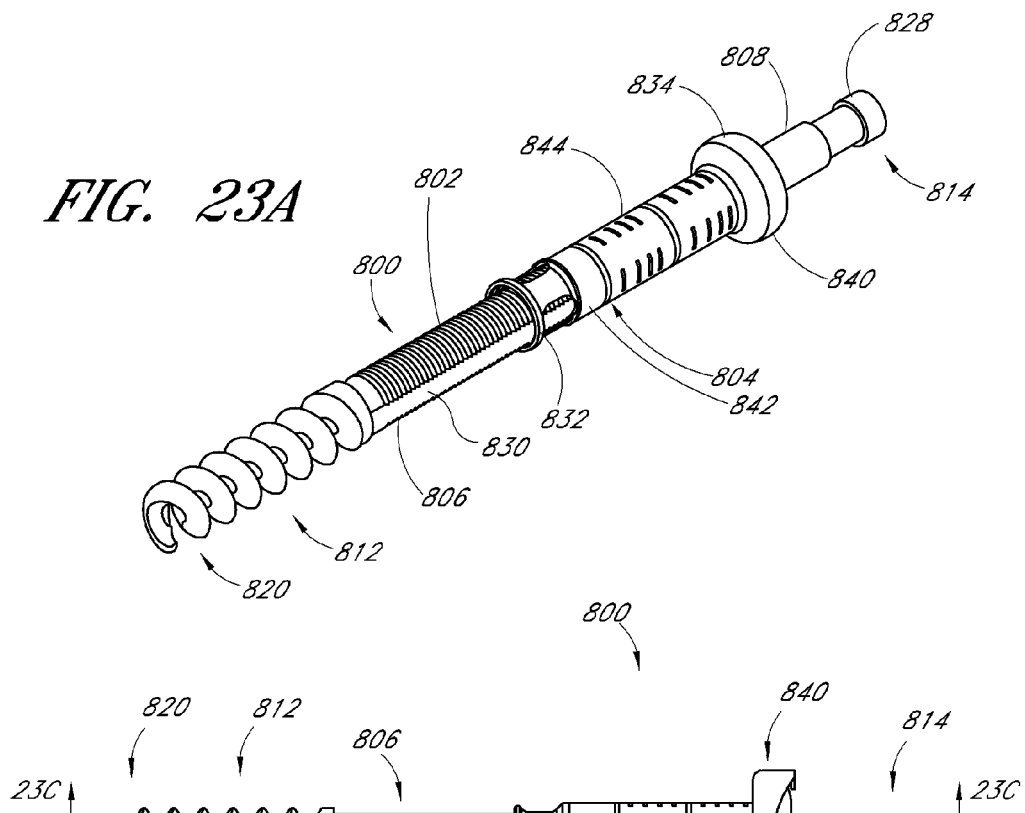
FIG. 23A is a perspective view of yet another embodiment of a fixation device.
Figure 23B:
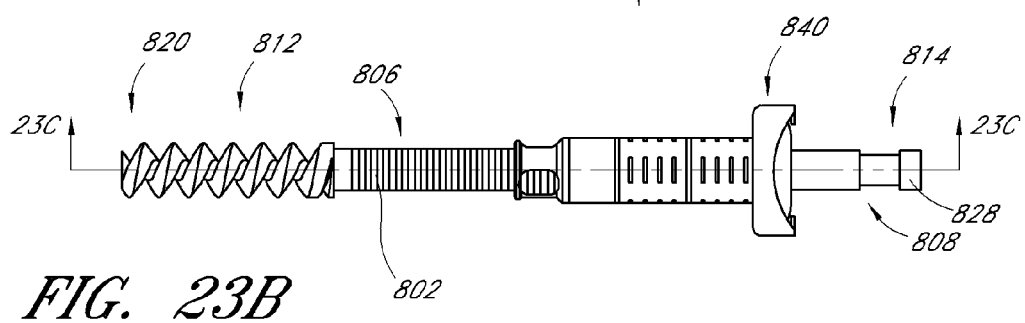
FIG. 23B is a side view of the fixation device shown in FIG. 23A.
Figure 23C:
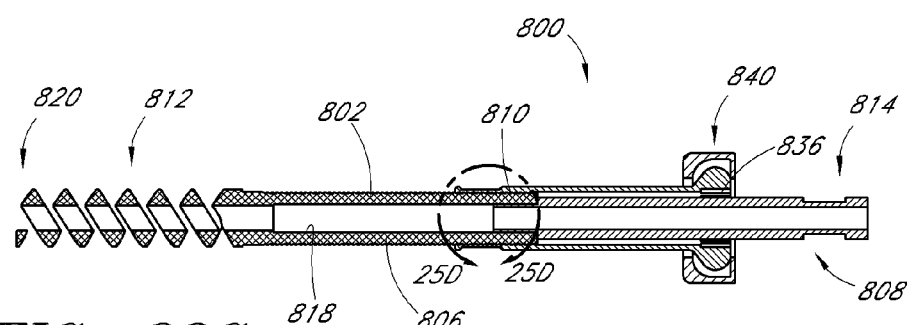
FIG. 23C is a longitudinal cross-sectional view of the fixation device shown in FIG. 23A.
Figure 23D:
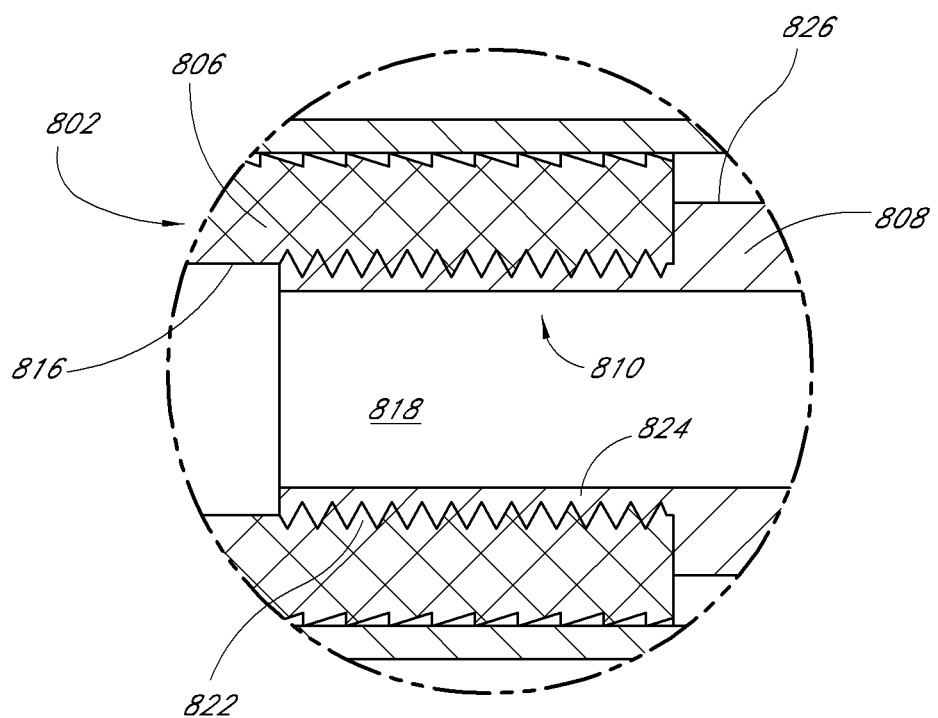
FIG. 23D is an enlarged view of a portion of the fixation device shown in FIG. 23A taken along section 23D-23D.

FIGS. 23A-D illustrate an embodiment of the bone fixation device 800 having a body 802 and a proximal anchor 804. In this embodiment, the body 802 comprises a first portion 806 and a second portion 808 that are coupled together at a junction 810 (FIG. 23D). In the illustrated embodiment, the first portion 806 carries a distal anchor 812 while the second portion 808 forms a proximal end 814 of the body 802. The first and second portions 806, 808 are preferably detachably coupled to each other at the junction 810. In the illustrated embodiment, the first and second portions 806, 808 are detachably coupled to each other via interlocking threads. Specifically, as best seen in FIG. 23D, the body 802 includes an inner surface 816, which defines a central lumen 818 that preferably extends from the proximal end 814 to a distal end 820 throughout the body 802. At the proximal end of the first portion 806, the inner surface 816 includes a first threaded portion 822. The first threaded portion 822 is configured to mate with a second threaded portion 824, which is located on the outer surface 826 of the second portion 808. The interlocking annular threads of the first and second threaded portions 822, 824 allow the first and second portions 806, 808 to be detachably coupled to each other. In one modified embodiment, the orientation of the first and second threaded portions 822, 824 can be reversed. That is, the first threaded portion 822 can be located on the outer surface of the first portion 806 and the second threaded portion 824 can be located on the inner surface 816 at the distal end of the second portion 808. Any of a variety of other releasable complementary engagement structures may also be used, to allow removal of second portion 808 following implantation, as is discussed below.

In a modified arrangement, the second portion 808 can comprise any of a variety of tensioning elements for permitting proximal tension to be placed on the distal anchor 812 while the proximal anchor 804 is advanced distally. For example, any of a variety of tubes or wires can be removably attached to the first portion 806 and extend proximally to the proximal handpiece. In one such arrangement, the first portion 806 can include a releasable connector in the form of a latching element, such as an eye or hook. The second portion 808 can include a complementary releasable connector (e.g., a complementary hook or eye) for engaging the first portion 806. In this manner, the second portion 808 can be detachably coupled to the first portion 806 such that proximal traction can be applied to the first portion 806 through the second portion 808 as will be explained below. Alternatively, the second portion 808 may be provided with an eye or hook, or transverse bar, around which or through which a suture or wire may be advanced, both ends of which are retained at the proximal end of the device. Following proximal tension on the tensioning element during the compression step, one end of the suture or wire is released, and the other end may be pulled free of the device. Alternate releasable proximal tensioning structures may be devised by those of skill in the art in view of the disclosure herein.

With particular reference to FIGS. 23A-23D, the proximal end 814 of the body 802 may be provided with a rotational coupling 828, for allowing the second portion 808 of the body 802 to be rotationally coupled to a rotation device. The proximal end 814 of the body 808 may be desirably rotated to accomplish one or two discrete functions. In one application of embodiments of the present inventions, the proximal end 814 is rotated to remove the second portion 808 of the body 802 following tensioning of the device to anchor an attachment to the bone. Rotation of the rotational coupling 828 may also be utilized to rotationally drive the distal anchor into the bone. Any of a variety of rotation devices may be utilized, such as electric drills or hand tools, which allow the clinician to manually rotate the proximal end 814 of the body 802. Thus, the rotational coupling 828 may have any of a variety of cross sectional configurations, such as one or more flats or splines.

With particular reference to FIG. 23A, the fixation device may include an antirotation lock between the first portion 806 of the body 802 and the proximal anchor 804. In the illustrated embodiment, the first portion 806 includes a pair of flat sides 830, which interact with corresponding flat structures 832 in the proximal anchor 804. One or three or more axially extending flats may also be used. As such, rotation of the proximal anchor 804 is transmitted to the first portion 806 and the distal anchor 812 of the body 802. Of course, those of skill in the art will recognize various other types of splines or other interfit structures can be used to prevent relative rotation of the proximal anchor and the first portion 806 of the body 802. For example, in one embodiment, the first portion 806 may include three flat sides, which interact with corresponding flat structures on the proximal anchor 804.

Figure 24A:
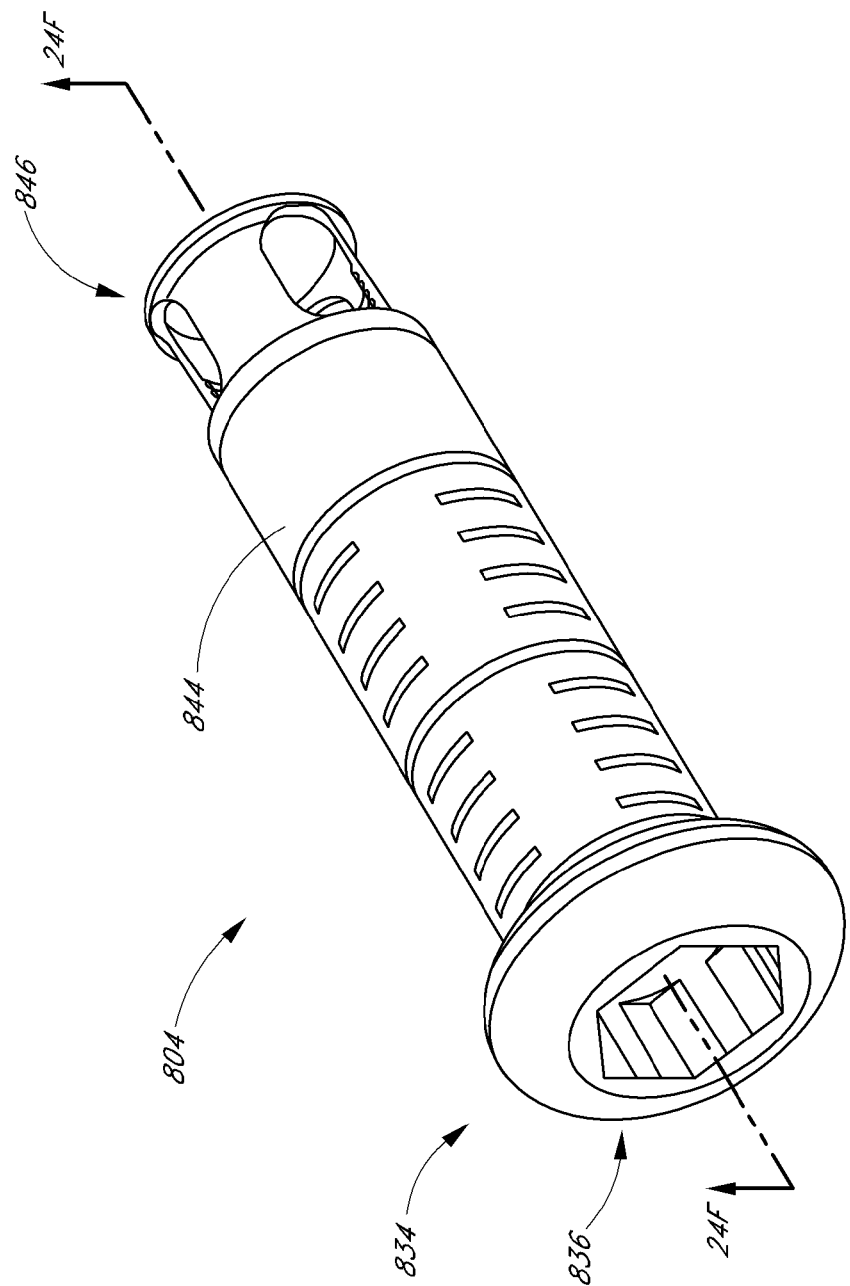
FIG. 24A is a perspective view of a proximal anchor, according to an embodiment.
Figures 24D, 24E:
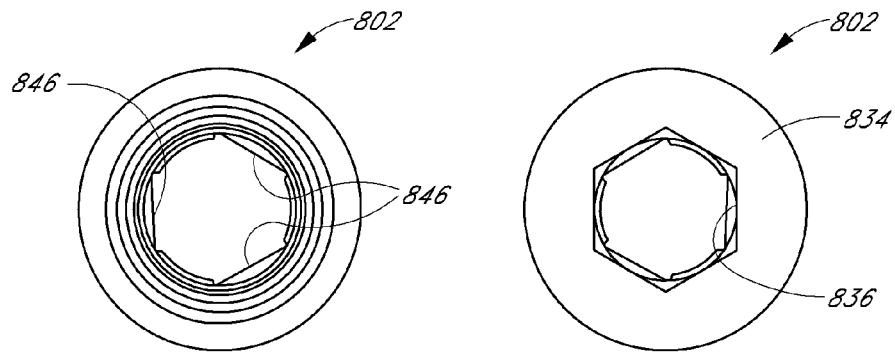
FIG. 24D is a bottom view of the proximal anchor shown in FIG. 24A.
FIG. 24E is a top view of the proximal anchor shown in FIG. 24A.
Figure 24B:
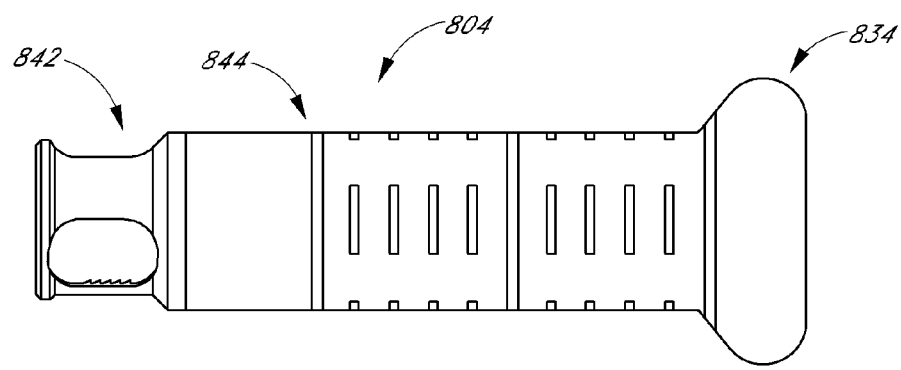
FIG. 24B is a side view of the proximal anchor shown in FIG. 24A.
Figure 24C:
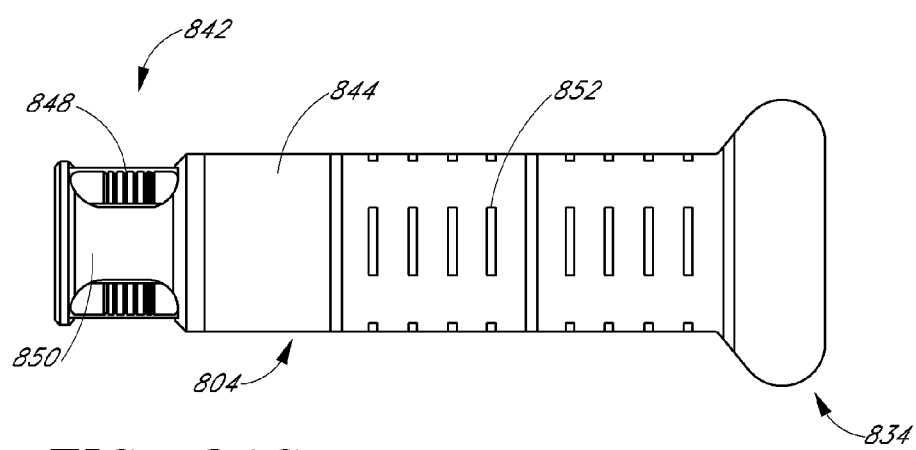
FIG. 24C is a side view of the proximal anchor shown in FIG. 24A.
Figure 24F:
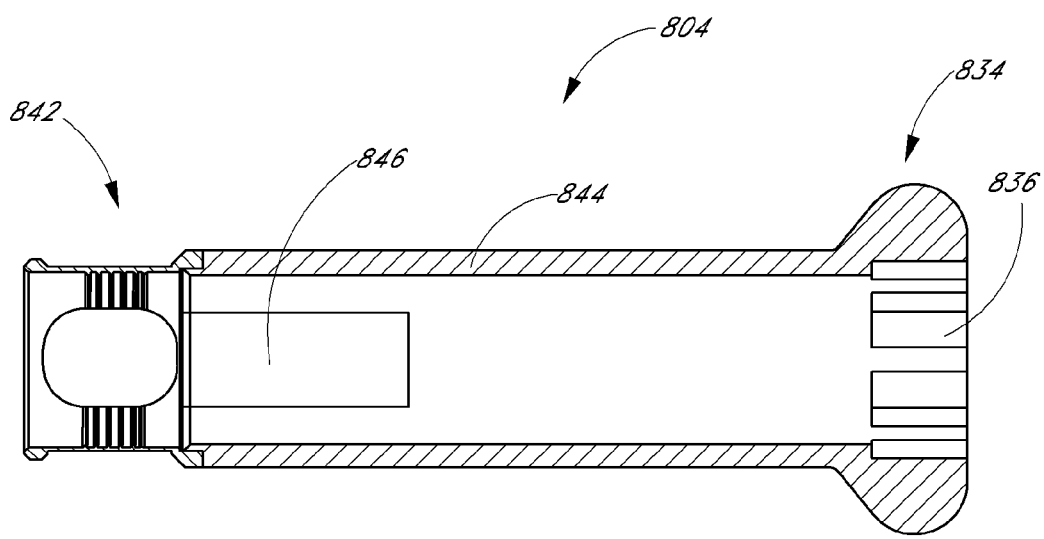
FIG. 24F is a cross-sectional view of the proximal anchor shown in FIG. 24A.

To rotate the proximal anchor 804, a flange 834 is preferably provided with a gripping structure to permit an insertion tool to rotate the flange 834. Any of a variety of gripping structures may be provided, such as one or more slots, flats, bores or the like. In one embodiment, the flange 834 is provided with a polygonal, and, in particular, a pentagonal or hexagonal recess 836. See FIG. 24A.

In FIGS. 23B and 23C, the proximal anchor 804 is shown in combination with a washer 840 that can be configured to interact with a head of the proximal anchor. The washer 840 can include a base and a side wall. The base and side wall can define a curved, semi-spherical or radiused surface that interacts with the corresponding curved, semi-spherical or radiused surface of the head. The surface surrounds an aperture formed in the base. This arrangement can allow the housing and/or body to extend through and pivot with respect to the washer. A detailed description of the washer 840 can be found in U.S. Pat. No. 6,951,561 issued on Oct. 4, 2005 entitled "PROXIMAL ANCHORS FOR BONE FIXATION SYSTEM," the entirety of the contents of which are incorporated herein by reference.

FIGS. 24A-F illustrate in more detail the proximal anchor 804 of FIGS. 23A-C. This embodiment can include a tubular housing 842. A detailed description of the tubular housing 842 can be found in U.S. Pat. No. 6,951,561 referred to above. In the illustrated embodiment, the tubular housing 842 can be attached to, coupled to, or integrally formed (partially or wholly) with a secondary tubular housing 844, which includes one or more anti-rotational features 846 (e.g., flat sides) for engaging corresponding anti-rotational features formed on the pin, which can be similar to the first portion 806 (e.g., see description above). The flange or collar 834 is attached, coupled or integrally formed with the proximal end of the secondary tubular housing. Teeth or flanges 848 on bridges 850 may also be configured such that the proximal anchor may be distally advanced and/or removed with rotation. The illustrated embodiment also advantageously includes visual indicia 852 (e.g., marks, grooves, ridges etc.) on the tubular housing 842 for indicating the depth of the proximal anchor 804 within the bone.

In one embodiment of use, the fixation device 800 of FIGS. 23A-C can have an axial length and outside diameter suitable for a hole drilled in the bone. The distal end 820 of the fixation device 800 is advanced distally into the hole until the distal anchor 812 reaches the distal end of the hole. The proximal anchor 804 may be carried by the fixation device 800 prior to advancing the body 802 into the hole, or may be attached following placement of the body 802 within the hole. Once the body 802 and proximal anchor 804 are in place, the clinician may use any of a variety of driving devices, such as electric drills or hand tools to rotate the proximal anchor 804 and thus cancellous bone anchor 812 into the head of the femur. In modified embodiments, the fixation device is configured to be self-drilling or self tapping such that a hole does not have to be formed before insertion into the bone.

Once the anchor 812 is in the desired location, proximal traction is applied to the proximal end 814 of body 802, such as by conventional hemostats, pliers or a calibrated loading device, while distal force is applied to the proximal anchor 804. In this manner, the proximal anchor 804 is advanced distally until the anchor 804 fits snugly against the outer surface of the bone. Appropriate tensioning of the fixation device 800 is accomplished by tactile feedback or through the use of a calibration device for applying a predetermined load on the implantation device. One advantage of the structure of certain embodiments is the ability to adjust compression independently of the setting of the distal anchor 812.

Following appropriate tensioning of the proximal anchor 804, the second portion 808 of the body 802 is preferably detached from the first portion 806 and removed. In the illustrated embodiment, this involves rotating the second portion 808 with respect to the first portion via the coupling 828. Following removal of the second portion 808 of each body 802, the access site may be closed and dressed in accordance with conventional wound closure techniques.

An advantage of certain embodiments of the fixation devices disclosed above is that the proximal anchor provides the device with a working range such that one device may accommodate varying distances between the distal anchor and the proximal anchor. In certain applications, this allows the technician to focus on the proper positioning of the distal anchor with the knowledge that the proximal anchor lies within the working range of the device. With the distal anchor positioned at the desired location, the proximal anchor may then be advanced along the body to compress the fracture and/or provide stability between bones. In a similar manner, the working range provides the technician with flexibility to adjust the depth of the proximal anchor. For example, in some circumstances, the bone may include voids, cysts, osteoporotic bone that impairs the stability of the distal anchor in the bone. Accordingly, in some circumstances, the technician may advance the distal anchor and then desire to retract the distal anchor such that it is better positioned in the bone. In another circumstance, the technician may inadvertently advance the distal tip through the bone into a joint space or other undesired area (e.g., spinal canal). In such circumstances, the working range of the device allows the technician to reverse and retract the anchor and recompress. Such adjustments are facilitated by the working range of the proximal anchor on the body.

Preferably, the clinician will have access to an array of fixation devices (e.g., fixation device 800) having, for example, different diameters, axial lengths and angular relationships. These may be packaged one per package in sterile envelopes or peelable pouches, or in dispensing cartridges which may each hold a plurality of devices 800. Upon encountering a use for which the use of a fixation device is deemed appropriate, the clinician will assess the dimensions and load requirements, and select a fixation device from the array which meets the desired specifications.

The fixation devices described above may be used in any of a wide variety of anatomical settings beside the spine as has been discussed. For example, lateral and medial malleolar fractures can be readily fixed using the device according to certain embodiments. For example, the fixation devices 800 can be used with the distal fibula and tibia. The fibula terminates distally in the lateral malleolus, and the tibia terminates distally in the medial malleolus. A fixation device 800 can extend through the lateral malleolus across the lateral malleolar fracture and into the fibula. The fixation device 800 can include a distal anchor for fixation within the fibula, an elongate body and a proximal anchor as has been discussed.

As mentioned above, the devices describe herein may also be used for spinal fixation. In embodiments optimized for spinal fixation in an adult human population, the body 800 can generally be within the range of from about 20-90 mm in length and within the range of from about 3.0-8.5 mm in maximum diameter. The length of the helical anchor, discussed above, may be about 8-80 millimeters. Of course, it is understood that these dimensions are illustrative and that they may be varied as required for a particular patient or procedure.

In spinal fixation applications, the fixation device 800 may be used as a trans-facet screw. That is, the fixation device extends through a facet of a first vertebra and into the facet of a second, typically inferior, vertebra, which vertebrae are referred to above as intermediate and inferior vertebral bodies. This procedure is typically (but not necessarily) performed with bilateral symmetry. Thus, even in the absence of a stabilizing bar tying pedicle screws to adjacent vertebrae or to the sacrum, and in the absence of translaminar screws that can extend through the spinous process, the fixation devices can be used to stabilize two vertebrae, such as L3 and L4 to each other pending the healing of a fusion. In one embodiment, the body 802 of fixation device 800 can have a length of approximately 10 mm-30 mm and the diameter of the body 802 can be approximately 3 mm to 5.5 mm.

The fixation device 800 may also be used as a trans-laminar facet screw. In this embodiment of use, the fixation device extends through the spinous process and facet of a first vertebra and into the facet of a second, typically inferior, vertebra. As with the previous embodiment, this procedure is typically (but not necessarily) performed with bilateral symmetry. In one embodiment, the body 802 of fixation device 800 can have a length of approximately 50 mm-90 mm and the diameter of the body is approximately 4 mm to 5.5 mm.

The fixation device may also be used is used as a facet-pedical screw (e.g., as used in the Boucher technique). In such an embodiment, the fixation device extends through the facet of a first vertebra and into the pedicle a second, typically inferior, vertebra. As with the previous embodiment, this procedure is typically (but not necessarily) performed with bilateral symmetry. In such an embodiment, the fixation device 800 and the body 802 can be approximately 20-40 millimeters in length and 3.0-5.5 millimeters in diameter.

FIGS. 25A-D illustrate another embodiment of a proximal anchor 860. In this embodiment, the proximal anchor 860 includes a recess 862 configured to receive a split ring 864. As will be explained in detail below, the proximal anchor 860 can include an anti-rotation feature to limit or prevent rotation of the ring 864 within the proximal anchor 860. In light of the disclosure herein, those of skill in the art will recognize various different configurations for limiting the rotation of the ring 864. However, a particularly advantageous arrangement will be described below with reference to the illustrated embodiment.

Figure 25A:
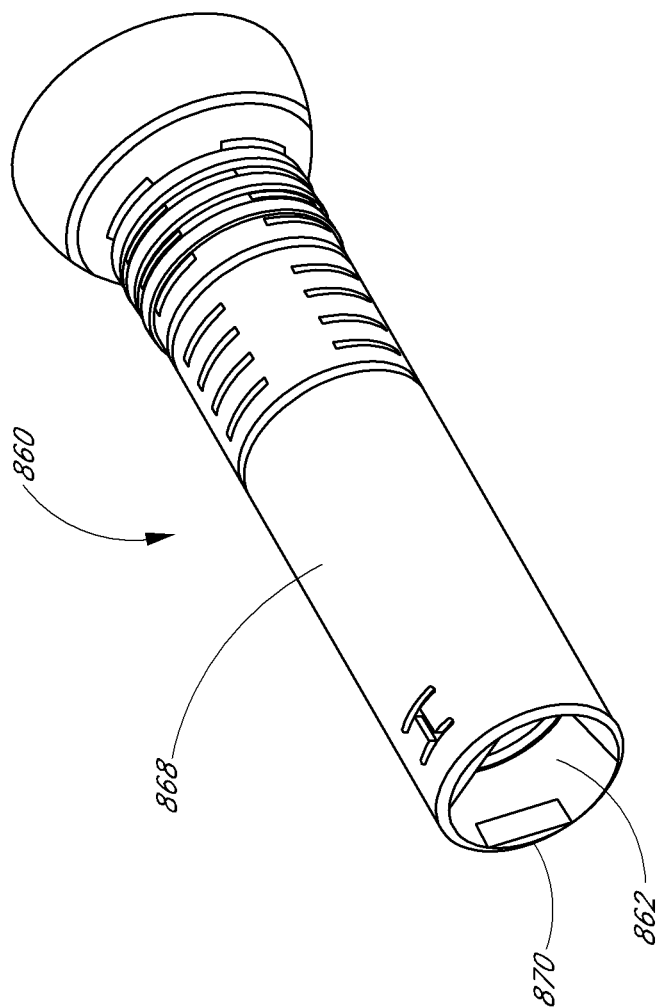
FIG. 25A is a perspective view of another embodiment of a proximal anchor.
Figure 25C:
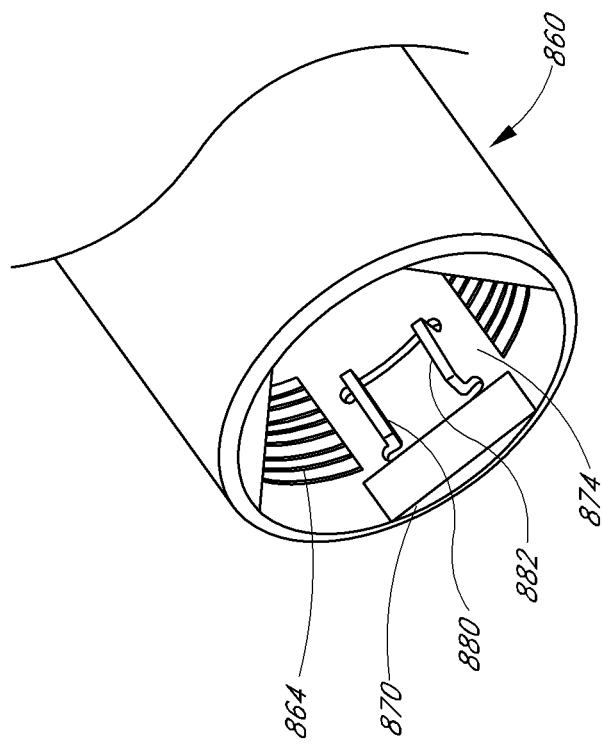
FIGS. 25B and 25C are enlarged views of a portion of a proximal anchor, according to an embodiment.
Figure 25B:
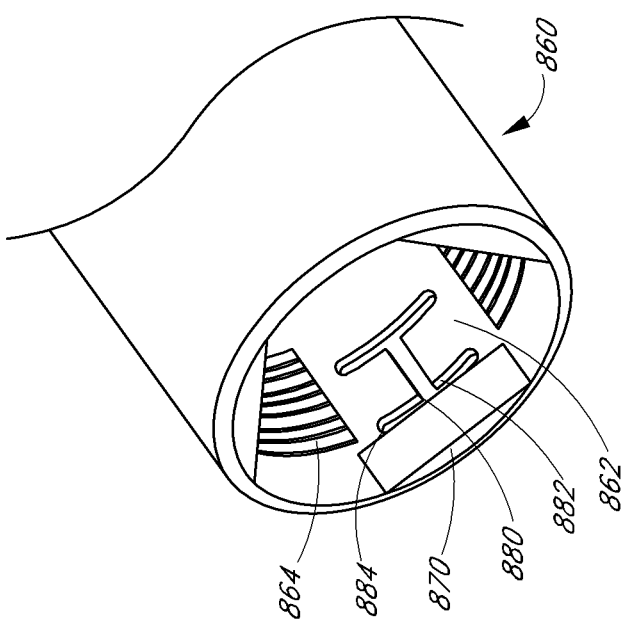
Figure 25D:
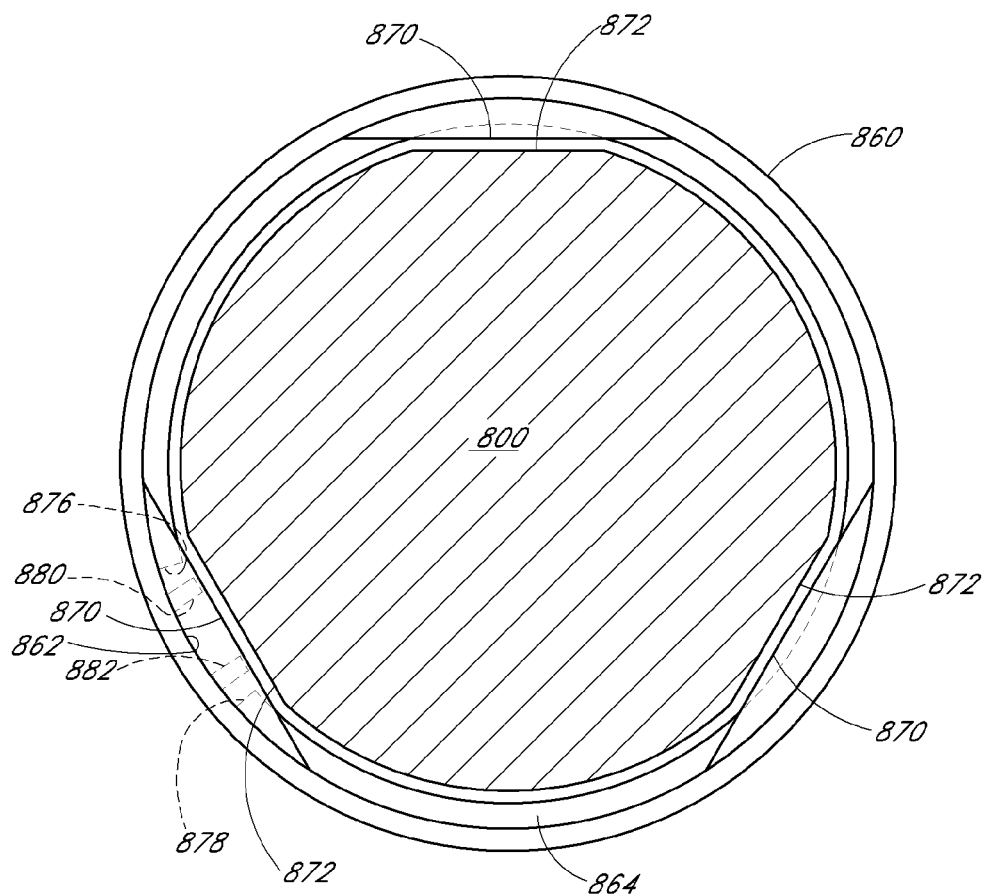
FIG. 25D is a front view of the proximal anchor shown in FIG. 25A.

In the illustrated embodiment, the proximal anchor 860 has a tubular housing 868 that can engage with a body 802 or a first portion 806 of the body 802, as described above. With reference to FIGS. 25B and 25D, the tubular housing 868 comprises one or more anti-rotational features 870 in the form of a plurality of flat sides that are configured to mate corresponding anti-rotational features 872 or flat sides of the body 802 of the fixation device 800. As shown in FIG. 25D, in the illustrated embodiment, the body 802 has three flat sides 872. Disposed between the flat sides 872 are the portions of the body 802 which include the complementary locking structures such as threads or ratchet like structures as described above. The complementary locking structures interact with the ring 864 as described above to resist proximal movement of the anchor 860 under normal use conditions while permitting distal movement of the anchor 860 over the body 802.

As mentioned above, the ring 864 is positioned within the recess 862. In the illustrated embodiment, the recess 862 and ring 864 are positioned near to and proximal of the anti-rotational features 870. However, the ring 864 can be located at any suitable position along the tubular housing 868 such that the ring 864 can interact with the retention features of the body 802.

During operation, the ring 864 may rotate to a position such that the gap 874 between the ends 876, 878 of the ring 864 lies above the complementary retention structures on the body 802. When the ring 865 is in this position, there is a reduced contact area between the split ring 864 the complementary retention structures thereby reducing the locking strength between the proximal anchor 860 and the body 802. In the illustrated embodiment, for example, the locking strength may be reduced by about ⅓ when the gap 874 over the complementary retention structures between flat sides 872. As such, it is advantageous to position the gap 874 on the flat sides 872 of the body 802 that do not include complementary retention structures.

To achieve this goal, the illustrated embodiment includes a pair of tabs 880, 882 that extend radially inward from the interior of the proximal anchor 800. The tabs 880, 882 are configured to limit or prevent rotational movement of the ring 864 relative to the housing 804 of the anchor 800. In this manner, the gap 874 of the ring 864 may be positioned over the flattened sides 872 of the body 802.

In the illustrated embodiment, the tabs 880, 882 have a generally rectangular shape and have a generally uniform thickness. However, it is contemplated that the tabs 880, 882 can be square, curved, or any other suitable shape for engaging with the ring 864 as described herein.

In the illustrated embodiment, the tabs 880, 882 are formed by making an H-shaped cut 884 in the tubular housing 860 and bending the tabs 880, 882 inwardly as shown in FIG. 25D. As shown in FIG. 25D, the tabs 880, 882 (illustrated in phantom) are interposed between the edges 876, 878 of the ring 864. The edges 876, 878 of the ring 864 can contact the tabs to limit the rotational movement of the ring 864. Those skilled in the art will recognize that there are many suitable manners for forming the tabs 880, 882. In addition, in other embodiments, the tabs 880, 882 may be replaced by a one or more elements or protrusions attached to or formed on the interior of the proximal anchor 860.

For the embodiments discussed herein, the pin, together with the distal anchor, and other components, can be manufactured in accordance with any of a variety of techniques which are well known in the art, using any of a variety of medical-grade construction materials. For example, the pin body and other components can be injection-molded from a variety of medical-grade polymers including high or other density polyethylene, nylon and polypropylene. The distal anchor can be separately formed from the pin body and secured thereto in a post-molding operation, using any of a variety of securing techniques such as solvent bonding, thermal bonding, adhesives, interference fits, pivotable pin and aperture relationships, and others known in the art. Preferably, however, the distal anchor is integrally molded with the pin body, if the desired material has appropriate physical properties.

Retention structures can also be integrally molded with the pin body. Alternatively, retention structures can be machined or pressed into the pin body in a post-molding operation, or secured using other techniques depending upon the particular design. Further, as recited in U.S. Pat. No. 6,951,561 referred to above, a variety of polymers, such as bioabsorbable polymers, can be used to fabricate components of the embodiments disclosed herein.

Figure 26:
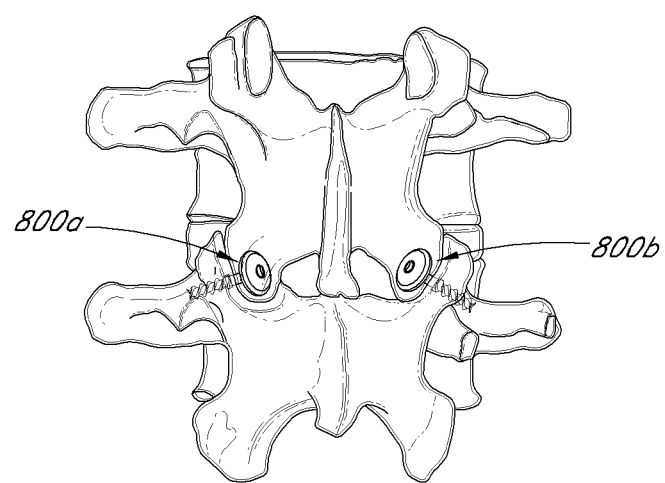
FIG. 26 is a posterior view of a portion of the lumbar spine with the fixation device shown in FIG. 23A being used as a trans-facet screw, according to an embodiment.

As shown in FIG. 26, the fixation devices 800a, 800b may be used to provide stability without additional hardware. In this example, the fixation devices 800a, 800b is used similarly to a trans-facet screw. That is, the fixation devices 800a, 800b extend through a facet of a first vertebra and into the facet of a second, typically inferior, vertebrae. As in the illustrated embodiment, this procedure is typically (but not necessarily) performed with bilateral symmetry. Thus, even in the absence of a stabilizing bar tying pedicle screws to adjacent vertebrae or to the sacrum, and in the absence of translaminar screws that can extend through the spinous process, the fixation devices 800a, 800b can be used to stabilize two vertebrae, such as L3 and L4 to each other pending the healing of a fusion. In one embodiment, the body of fixation devices 800a, 800b can have a length of approximately 10 mm-30 mm and the diameter of the body is approximately 3 mm to 5.5 mm.

In the embodiment of FIG. 26, the flange of the proximal anchor is typically supported directly against the outer surface of a vertebra. Because the outer surface is typically non-planar and/or the insertion angle of the fixation device is not perpendicular to the outer surface, an angularly fixed flange may contact only a portion of the outer surface. That is, the contact surface of the flange may not sit flush on the outer surface of the vertebra. This may cause the vertebra to crack due to high stress concentrations. This can result in poor fusion rates.

As such, in these applications, angularly adjustable flanges can be particularly advantageous because the flange can rotate with respect to the body and thereby the bone contacting surface may be positioned more closely to the outer surface of the vertebra. This can result in more bone contacting surface being utilized and the stress supported by the fixation device is spread out over a larger area of the vertebra. These angularly adjustable flanges may also be used with the spinal cages and rods. In such embodiments, the angle of the body fixation device may be not be perpendicular to the contact surface of the fixation rod or plate. In such situations, the angularly adjustable flange allows the flange to rotate and sit flush against the fixation rod and plate.

In the above embodiments, it may be advantageous to drill a counter bore into the first vertebra for receiving a portion of the proximal anchor. In such embodiments, the counter bore will typically have a diameter that is slightly larger than the outer diameter of the proximal anchor so that the proximal anchor may sit at least partially below the outer surface of the vertebra.

In certain regions of the spine, the dimension transverse to a facet joint and through the adjacent facets is relatively small. In these circumstances, the fixation may desirably include a through bore, opening through the distal cortex of the distal facet. The fixation device described above may be utilized either in a blind hole application, which the distal anchor is buried within the bone, or a through bore application is which the distal helix extends into and potentially through the distal cortex. However, a through bore fixation device may also be used.

The fixation devices 800 are preferably installed using a percutaneous or minimally invasive approach in which the procedure is done through one or more percutaneous small openings in a manner similar to that described above with respect to the stabilization devices 12. As mentioned above, the fixation device 800 can be positioned below (or above in other embodiments) the stabilization device 12, which can be used to promote spinal fusion below the spinal level at which motion is limited by the dynamic stabilization device 12. In such an embodiment, the dynamic stabilization device can provide adjacent level support as an adjunct to fusion therapy. An advantage of this system and technique is that both the stabilization device 12 and the fixation device 800 can be inserted into the spine utilizing a minimally invasive approach in which the procedure is done through one or more percutaneous small openings. In other embodiments, the fixation devices 800 can be replaced and/or supplemented with other fixation devices of the type known in the art such as, for example, pedicle screws and rod constructs, cages, etc.

Figure 27:
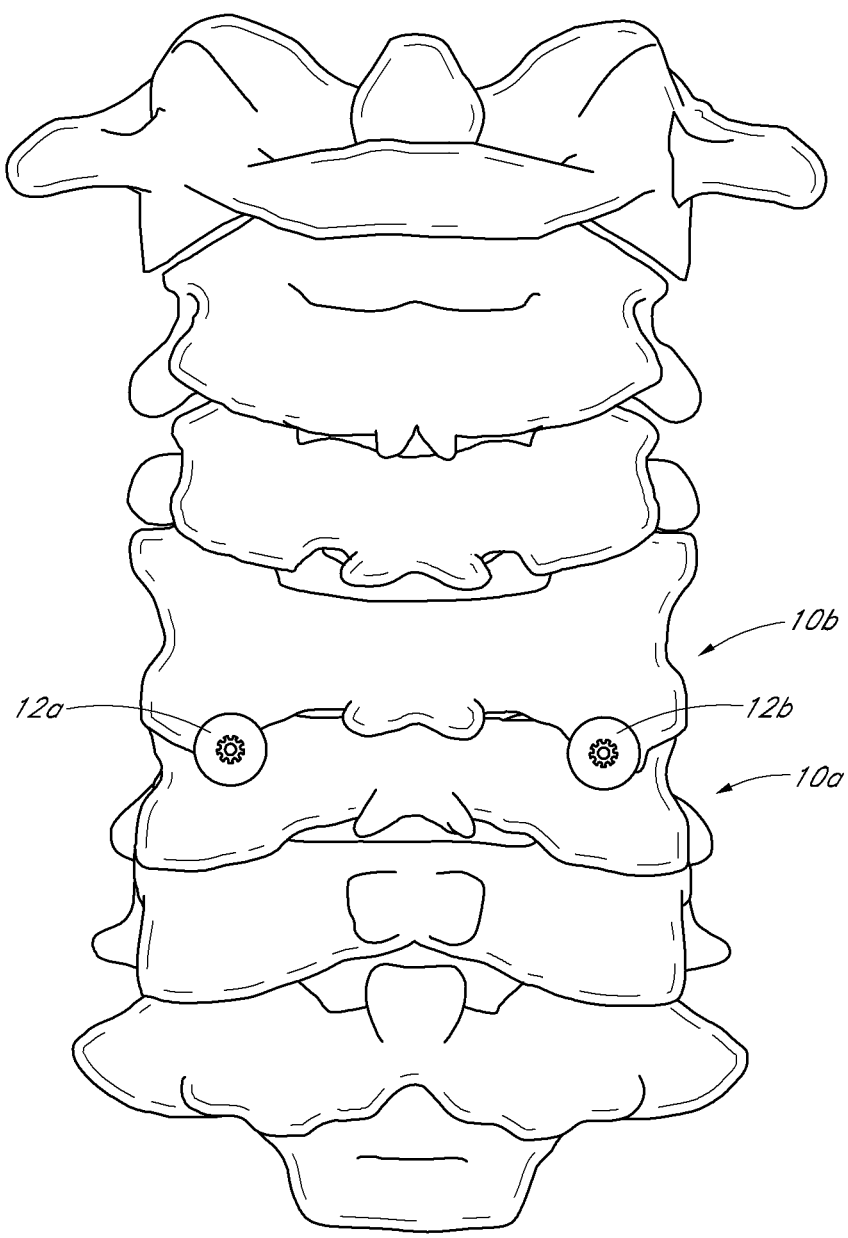
FIG. 27 is a posterior view of a portion of a vertebra having two devices similar to that shown in FIG. 23A implanted substantially bilaterally therein, according to an embodiment.
Figure 28:
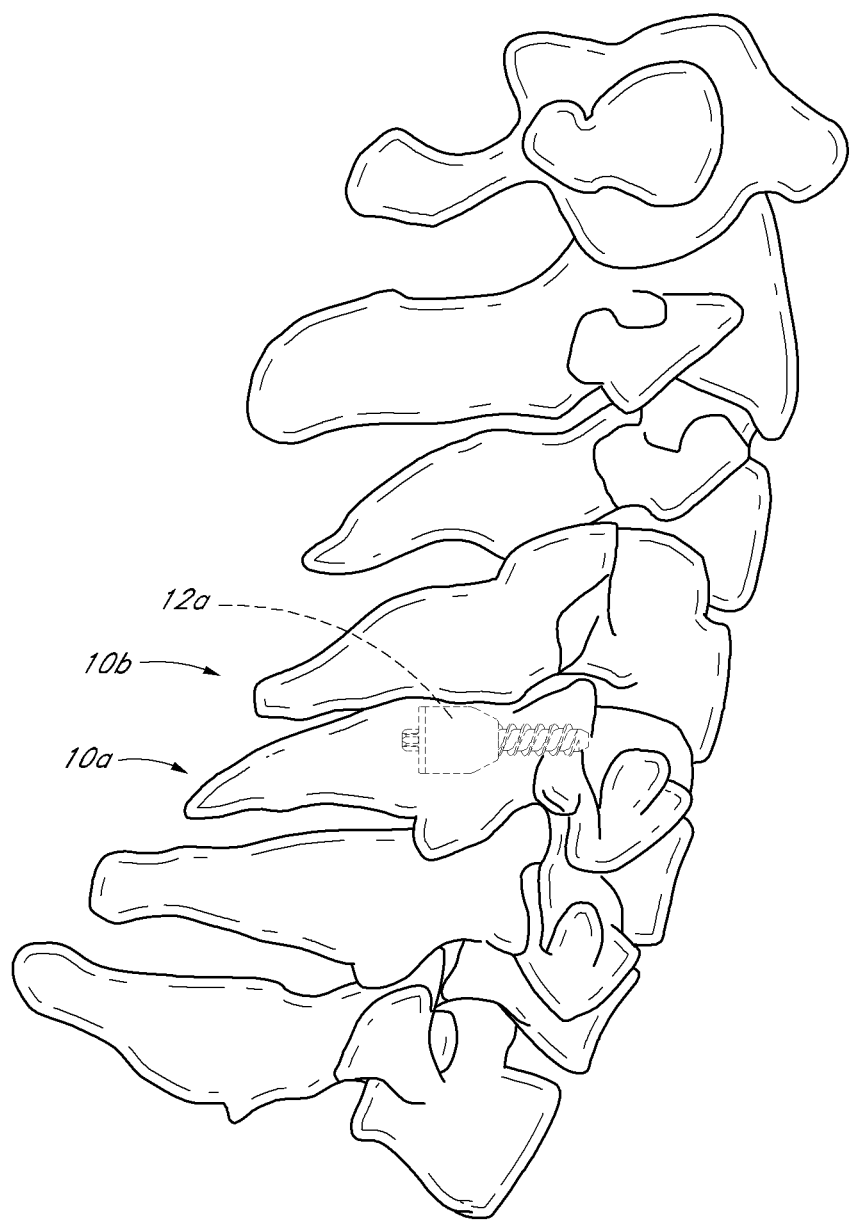

FIGS. 27-28 are rear and side elevational views of the cervical spine in accordance with another embodiment. The methods and devices disclosed herein can be used in various areas along the spinal column and can be combined with other methods and devices. For example, FIGS. 27-28 illustrate that at least one of the dynamic stabilization device 12 and the fixation device 800 can be used in the cervical vertebrae area of the spine. As shown however, the dynamic stabilization device 12 is illustrated. In embodiments wherein the dynamic stabilization device 12 is used in the cervical spine, for example, it is contemplated that the configuration of the dynamic stabilization device 12 has a length from about 5 mm to about 25 mm when configured for the cervical spine. The dynamic stabilization device 12 can therefore be specifically configured for uses in various parts of the spine.

In addition, the components disclosed herein may be provided with any of a variety of structural modifications to accomplish various objectives, such as osteoincorporation, or more rapid or uniform absorption into the body. For example, osteoincorporation may be enhanced by providing a micropitted or otherwise textured surface on the components. Alternatively, capillary pathways may be provided throughout the pin and collar, such as by manufacturing the components from an open cell foam material, which produces tortuous pathways through the device. This construction increases the surface area of the device which is exposed to body fluids, thereby generally increasing the absorption rate. Capillary pathways may alternatively be provided by laser drilling or other technique, which will be understood by those of skill in the art in view of the disclosure herein. In general, the extent to which the component can be permeated by capillary pathways or open cell foam passageways may be determined by balancing the desired structural integrity of the device with the desired reabsorption time, taking into account the particular strength and absorption characteristics of the desired polymer.

The component of the embodiments disclosed herein may be sterilized by any of the well known sterilization techniques, depending on the type of material. Suitable sterilization techniques include heat sterilization, radiation sterilization, such as cobalt 60 irradiation or electron beams, ethylene oxide sterilization, and the like.

The specific dimensions of any of the components and bone fixation devices can be readily varied depending upon the intended application, as will be apparent to those of skill in the art in view of the disclosure herein. Moreover, the components and devices have been described in terms of certain preferred embodiments, other embodiments including variations in the number of parts, dimensions, configuration and materials will be apparent to those of skill in the art in view of the disclosure herein. In addition, all features discussed in connection with any one embodiment herein can be readily adapted for use in other embodiments herein to form various combinations and sub-combinations. The use of different terms or reference numerals for similar features in different embodiments does not imply differences other than those which may be expressly set forth. Accordingly, the present inventions are intended to be described solely by reference to the appended claims, and not limited to the preferred embodiments disclosed herein.

What is claimed is:

1. A method of limiting at least one degree of movement between a superior vertebral body, an intermediate vertebral body, and an inferior vertebral body of a patient, the intermediate vertebral body being disposed between the superior and inferior vertebral bodies entirely from posterior access sites, comprising:

advancing a distal end of a stabilization device into an intermediate vertebral body from a posterior access site;

positioning, from a posterior access site, a proximal portion of the stabilization device such that the proximal portion limits movement between the superior vertebral body and the intermediate vertebral body while providing at least some degree of movement between the superior vertebral body and the intermediate vertebral body; and advancing, from a posterior access site, a distal end of a fixation device into the intermediate vertebral body and into the inferior vertebral body for stabilizing the intermediate vertebral body and the inferior vertebral body to allow fusion between the intermediate vertebral body and the inferior vertebral body.

2. The method of claim 1, further comprising maintaining the patient in a face down position during the step of advancing a distal end of a stabilization device into the intermediate vertebral body.

3. The method of claim 1, wherein the steps of advancing a distal end of a stabilization device into a pedicle of the intermediate vertebral body and positioning a proximal portion of the stabilization device are accomplished through a minimally invasive surgical approach.

4. The method of claim 1, wherein advancing a distal end of a stabilization device the intermediate vertebral body further comprises advancing the stabilization device over a guidewire.

5. The method of claim 1, wherein advancing a distal end of a stabilization device into the intermediate vertebral body further comprises advancing the stabilization device through an expanded tissue tract.

6. The method of claim 1, wherein the superior vertebral body is located caudal to the inferior vertebral body.

* * * * *